(12) United States Patent
Bonadio et al.

(10) Patent No.: US 9,757,110 B2
(45) Date of Patent: Sep. 12, 2017

(54) INSTRUMENT ACCESS DEVICE

(71) Applicant: Atropos Limited, County Wicklow (IE)

(72) Inventors: Frank Bonadio, County Wicklow (IE); John Butler, County Mayo (IE); Trevor Vaugh, County Offaly (IE)

(73) Assignee: Atropos Limited, County Wicklow (IE)

( * ) Notice: Subject to any disclaimer, the term of this patent is extended or adjusted under 35 U.S.C. 154(b) by 165 days.

(21) Appl. No.: 14/471,838

(22) Filed: Aug. 28, 2014

(65) Prior Publication Data

US 2015/0148611 A1     May 28, 2015

Related U.S. Application Data

(63) Continuation of application No. 13/175,822, filed on Jul. 1, 2011, now Pat. No. 8,888,693, which is a
(Continued)

(30) Foreign Application Priority Data

Dec. 1, 1998 (IE) .......................................... 980997
Dec. 1, 1998 (IE) .......................................... 980999
(Continued)

(51) Int. Cl.
*A61B 17/34*     (2006.01)
*A61B 17/02*     (2006.01)
(Continued)

(52) U.S. Cl.
CPC ...... *A61B 17/0218* (2013.01); *A61B 17/0293* (2013.01); *A61B 17/3421* (2013.01);
(Continued)

(58) Field of Classification Search
CPC ........................ A61B 17/3423; A61B 17/3431
See application file for complete search history.

(56) References Cited

U.S. PATENT DOCUMENTS 1,157,202 A    10/1915    McLeland
1,598,284 A    8/1926    Kinney
(Continued)

FOREIGN PATENT DOCUMENTS

DE    37 39 532    12/1988
DE    37 37 121    5/1989
(Continued)

OTHER PUBLICATIONS

Kagaya, "Laparoscopic cholecystectomy via two ports, using the "Twin-Port" system", J. Hepatobiliary Pancreat Surg (2001) 8:76-80.
(Continued)

*Primary Examiner* — David Bates
(74) *Attorney, Agent, or Firm* — Bookoff McAndrews, PLLC

(57) ABSTRACT

An instrument access device (500) comprises a distal O-ring (11) for insertion into a wound interior, a proximal member for location externally of a wound opening and a sleeve (12) extending in two layers between the distal O-ring (11) and the proximal member. The proximal member comprises an inner proximal ring member (25) and an outer proximal ring member (24) between which the sleeve (12) is led. A seal housing (300) is mounted to the inner proximal ring member (25). A gelatinous elastomeric seal (302) with a pinhole opening (303) therethrough is received in the housing (300). An instrument may be extended through the seal (302) to access the wound interior through the retracted wound opening in a sealed manner.

20 Claims, 54 Drawing Sheets

Related U.S. Application Data continuation of application No. 11/246,909, filed on Oct. 11, 2005, now Pat. No. 7,998,068, which is a continuation-in-part of application No. 10/736,234, filed on Dec. 16, 2003, now abandoned, said application No. 11/246,909 is a continuation-in-part of application No. 10/678,653, filed on Oct. 6, 2003, now Pat. No. 7,559,893, which is a continuation-in-part of application No. 10/133,979, filed on Apr. 29, 2002, now Pat. No. 6,846,287, which is a continuation of application No. 09/801,826, filed on Mar. 9, 2001, now abandoned, which is a continuation of application No. PCT/IE99/00122, filed on Dec. 1, 1999, said application No. 10/678,653 is a continuation-in-part of application No. 10/374,523, filed on Feb. 27, 2003, now Pat. No. 7,445,597, which is a continuation of application No. 09/849,341, filed on May 7, 2001, now Pat. No. 6,582,364, which is a continuation of application No. 09/688,138, filed on Oct. 16, 2000, now Pat. No. 6,254,534, said application No. 11/246,909 is a continuation-in-part of application No. 10/665,395, filed on Sep. 22, 2003, now Pat. No. 7,867,164, which is a continuation-in-part of application No. 10/374,523, filed on Feb. 27, 2003, now Pat. No. 7,445,597, which is a continuation of application No. 09/849,341, filed on May 7, 2001, now Pat. No. 6,582,364, which is a continuation of application No. 09/688,138, filed on Oct. 16, 2000, now Pat. No. 6,254,534, said application No. 11/246,909 is a continuation-in-part of application No. 10/374,523, filed on Feb. 27, 2003, now Pat. No. 7,445,597, which is a continuation of application No. 09/849,341, filed on May 7, 2001, now Pat. No. 6,582,364, which is a continuation of application No. 09/688,138, filed on Oct. 16, 2000, now Pat. No. 6,254,534, said application No. 11/246,909 is a continuation-in-part of application No. 10/133,979, filed on Apr. 29, 2002, now Pat. No. 6,846,287, which is a continuation of application No. 09/801,826, filed on Mar. 9, 2001, now abandoned, which is a continuation of application No. PCT/IE99/00122, filed on Dec. 1, 1999, said application No. 11/246,909 is a continuation-in-part of application No. 10/902,440, filed on Jul. 30, 2004, now abandoned, which is a continuation-in-part of application No. 10/736,234, filed on Dec. 16, 2003, now abandoned, said application No. 10/902,440 is a continuation-in-part of application No. 10/678,653, filed on Oct. 6, 2003, now Pat. No. 7,559,893, which is a continuation-in-part of application No. 10/133,979, filed on Apr. 29, 2002, now Pat. No. 6,846,287, which is a continuation of application No. 09/801,826, filed on Mar. 9, 2001, now abandoned, which is a continuation of application No. PCT/IE99/00122, filed on Dec. 1, 1999, said application No. 10/678,653 is a continuation-in-part of application No. 10/374,523, filed on Feb. 27, 2003, now Pat. No. 7,445,597, which is a continuation of application No. 09/849,341, filed on May 7, 2001, now Pat. No. 6,582,364, which is a continuation of application No. 09/688,138, filed on Oct. 16, 2000, now Pat. No. 6,254,534, said application No. 10/902,440 is a continuation-in-part of application No. 10/374,523, filed on Feb. 27, 2003, now Pat. No. 7,445,597, which is a continuation of application No. 09/849,341, filed on May 7, 2001, now Pat. No. 6,582,364, which is a continuation of application No. 09/688,138, filed on Oct. 16, 2000, now Pat. No. 6,254,534, said application No. 10/902,440 is a continuation-in-part of application No. 10/374,523, filed on Feb. 27, 2003, now Pat. No. 7,445,597, which is a continuation of application No. 09/849,341, filed on May 7, 2001, now Pat. No. 6,582,364, which is a continuation of application No. 09/688,138, filed on Oct. 16, 2000, now Pat. No. 6,254,534, said application No. 10/902,440 is a continuation-in-part of application No. 10/315,233, filed on Dec. 10, 2002, now abandoned, which is a continuation of application No. 09/804,552, filed on Mar. 13, 2001, now Pat. No. 6,578,577, which is a continuation of application No. PCT/IE99/00123, filed on Dec. 1, 1999, said application No. 10/902,440 is a continuation-in-part of application No. 10/133,979, filed on Apr. 29, 2002, now Pat. No. 6,846,287, which is a continuation of application No. 09/801,826, filed on Mar. 9, 2001, now abandoned, which is a continuation of application No. PCT/IE99/00122, filed on Dec. 1, 1999.

(60) Provisional application No. 60/433,603, filed on Dec. 16, 2002, provisional application No. 60/453,200, filed on Mar. 11, 2003, provisional application No. 60/415,780, filed on Oct. 4, 2002, provisional application No. 60/428,215, filed on Nov. 22, 2002, provisional application No. 60/490,909, filed on Jul. 30, 2003, provisional application No. 60/617,094, filed on Oct. 12, 2004, provisional application No. 60/699,370, filed on Jul. 15, 2005, provisional application No. 60/490,909, filed on Jul. 30, 2003, provisional application No. 60/617,094, filed on Oct. 12, 2004.

(30) Foreign Application Priority Data

| | | |
|---|---|---|
| Feb. 15, 1999 | (IE) | 990107 |
| Feb. 15, 1999 | (IE) | 990108 |
| Feb. 15, 1999 | (IE) | 990109 |
| Feb. 15, 1999 | (IE) | 990110 |
| Feb. 15, 1999 | (IE) | 990111 |
| Feb. 15, 1999 | (IE) | 990112 |
| May 24, 1999 | (IE) | 990416 |
| Oct. 14, 1999 | (IE) | 990861 |
| Dec. 1, 1999 | (WO) | PCT/IE99/00122 |
| Dec. 1, 1999 | (WO) | PCT/IE99/00123 |
| Dec. 16, 1999 | (IE) | 991053 |
| Feb. 18, 2000 | (EP) | 00650010 |
| Sep. 19, 2002 | (IE) | 2002/0754 |
| Oct. 11, 2004 | (IE) | 2004/0686 |

(51) Int. Cl.

| | |
|---|---|
| *A61M 13/00* | (2006.01) |
| *A61B 1/32* | (2006.01) |
| *A61B 17/00* | (2006.01) |
| *A61B 90/40* | (2016.01) |

(52) U.S. Cl.
CPC ...... *A61B 17/3423* (2013.01); *A61B 17/3431* (2013.01); *A61B 17/3474* (2013.01); *A61B 17/3498* (2013.01); *A61M 13/003* (2013.01); *A61B 1/32* (2013.01); *A61B 17/3462* (2013.01); *A61B 90/40* (2016.02); *A61B 2017/00477* (2013.01); *A61B 2017/0225* (2013.01); *A61B 2017/347* (2013.01); *A61B 2017/3429* (2013.01); *A61B 2017/3435* (2013.01); *A61B 2017/3443* (2013.01); *A61B 2017/3482* (2013.01); *A61B 2017/3492* (2013.01)

(56) References Cited

U.S. PATENT DOCUMENTS

| | | |
|---|---|---|
| 1,810,466 A | 6/1931 | Deutsch |
| 2,219,564 A | 10/1940 | Reyniers |
| 2,305,289 A | 12/1942 | Coburg |
| 2,695,608 A | 11/1954 | Gibbon |
| 2,835,253 A | 5/1958 | Borgeson |
| 2,853,075 A | 10/1958 | Hoffman |
| 3,039,468 A | 6/1962 | Price |
| 3,111,943 A | 11/1963 | Orndorff |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,592,198 A | 7/1971 | Evans |
| 3,656,485 A | 4/1972 | Robertson |
| 3,685,786 A | 8/1972 | Woodson |
| 3,717,151 A | 2/1973 | Collett |
| 3,729,006 A | 4/1973 | Wilder et al. |
| 3,782,370 A | 1/1974 | McDonald |
| 3,797,478 A | 3/1974 | Walsh et al. |
| 3,807,393 A | 4/1974 | McDonald |
| 3,828,764 A | 8/1974 | Jones |
| 3,841,332 A | 10/1974 | Treacle |
| 3,853,126 A | 12/1974 | Schulte |
| 3,853,127 A | 12/1974 | Spademan |
| 3,856,021 A | 12/1974 | McIntosh |
| 3,907,389 A | 9/1975 | Cox et al. |
| 3,915,171 A | 10/1975 | Shermeta |
| 3,965,890 A | 6/1976 | Gauthier |
| 3,996,623 A | 12/1976 | Kaster |
| 3,998,217 A | 12/1976 | Trumbull et al. |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,083,370 A | 4/1978 | Taylor |
| 4,096,853 A | 6/1978 | Weigand |
| 4,130,113 A | 12/1978 | Graham |
| 4,177,814 A | 12/1979 | Knepshield |
| 4,188,945 A | 2/1980 | Wenander |
| 4,217,664 A | 8/1980 | Faso |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lehrman |
| 4,367,728 A | 1/1983 | Mutke |
| 4,399,816 A | 8/1983 | Spangler |
| 4,411,659 A | 10/1983 | Jensen et al. |
| 4,421,296 A | 12/1983 | Stephens |
| 4,424,833 A | 1/1984 | Spector |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,485,490 A | 12/1984 | Akers et al. |
| 4,488,877 A | 12/1984 | Klein |
| 4,543,088 A | 9/1985 | Bootman |
| 4,550,713 A | 11/1985 | Hyman |
| 4,553,537 A | 11/1985 | Rosenberg |
| 4,601,710 A | 7/1986 | Moll |
| 4,610,665 A | 9/1986 | Matsumuto |
| 4,626,245 A | 12/1986 | Weinstein |
| 4,634,424 A | 1/1987 | O'Boyle |
| 4,649,904 A | 3/1987 | Krauter |
| 4,654,030 A | 3/1987 | Moll et al. |
| 4,673,393 A | 6/1987 | Suzuki et al. |
| 4,673,394 A | 6/1987 | Fenton |
| 4,755,170 A | 7/1988 | Golden |
| 4,776,843 A | 10/1988 | Martinez et al. |
| 4,777,943 A | 10/1988 | Chvapil |
| 4,784,646 A | 11/1988 | Feingold |
| 4,798,594 A | 1/1989 | Hillstead |
| 4,809,679 A | 3/1989 | Shimonaka |
| 4,863,438 A | 9/1989 | Gauderer |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,002,557 A | 3/1991 | Hasson |
| 5,015,228 A | 5/1991 | Columbus et al. |
| 5,019,101 A | 5/1991 | Purkait |
| 5,026,366 A | 6/1991 | Leckrone |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima |
| 5,125,897 A | 6/1992 | Quinn et al. |
| 5,129,885 A | 7/1992 | Green et al. |
| 5,141,498 A | 8/1992 | Christian |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,178,162 A | 1/1993 | Bose |
| 5,188,595 A | 2/1993 | Jacobi |
| 5,192,301 A | 3/1993 | Kamiya et al. |
| 5,197,955 A | 3/1993 | Stephens et al. |
| 5,207,656 A | 5/1993 | Kranys |
| 5,209,737 A | 5/1993 | Richartt |
| 5,211,370 A | 5/1993 | Powers |
| 5,211,633 A | 5/1993 | Strouder |
| 5,213,114 A | 5/1993 | Bailey, Jr. |
| 5,234,455 A | 8/1993 | Mulhollan |
| 5,242,409 A | 9/1993 | Buelna |
| 5,248,304 A | 9/1993 | Vigdorchik et al. |
| 5,261,883 A | 11/1993 | Hood et al. |
| 5,263,922 A | 11/1993 | Sova et al. |
| 5,269,763 A | 12/1993 | Boehmer |
| 5,269,772 A | 12/1993 | Wilk |
| D343,236 S | 1/1994 | Quigley et al. |
| 5,279,575 A | 1/1994 | Sugarbaker |
| D346,022 S | 4/1994 | Quigley et al. |
| 5,299,582 A | 4/1994 | Potts |
| 5,300,036 A | 4/1994 | Mueller |

(56) References Cited

U.S. PATENT DOCUMENTS

| | | |
|---|---|---|
| 5,308,336 A | 5/1994 | Hart et al. |
| 5,309,896 A | 5/1994 | Moll et al. |
| 5,316,541 A | 5/1994 | Fischer |
| 5,320,611 A | 6/1994 | Bonutti |
| 5,330,437 A | 7/1994 | Durman |
| 5,330,497 A | 7/1994 | Freitas |
| 5,334,143 A | 8/1994 | Carroll |
| 5,336,192 A | 8/1994 | Palestrant |
| 5,342,315 A | 8/1994 | Rowe et al. |
| 5,342,385 A | 8/1994 | Norelli et al. |
| 5,350,364 A | 9/1994 | Stephens et al. |
| 5,364,345 A | 11/1994 | Lowery et al. |
| 5,366,478 A | 11/1994 | Brinkerhoff et al. |
| 5,368,545 A | 11/1994 | Schaller et al. |
| 5,383,861 A | 1/1995 | Hempel |
| 5,385,553 A | 1/1995 | Hart et al. |
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers |
| 5,407,433 A | 4/1995 | Loomas |
| 5,423,848 A | 6/1995 | Washizuka et al. |
| 5,429,609 A | 7/1995 | Yoon |
| 5,431,676 A | 7/1995 | Durbal |
| 5,443,452 A | 8/1995 | Hart et al. |
| 5,456,284 A | 10/1995 | Ryan |
| 5,476,475 A | 12/1995 | Gadberry |
| 5,480,410 A | 1/1996 | Cuschieri et al. |
| 5,496,280 A | 3/1996 | Vandenbroeck |
| 5,503,112 A | 4/1996 | Luhman |
| 5,514,109 A | 5/1996 | Mollenauer et al. |
| 5,514,133 A | 5/1996 | Golub et al. |
| 5,520,632 A | 5/1996 | Leveen |
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,545,179 A | 8/1996 | Williamson, IV |
| 5,562,632 A | 10/1996 | Davila |
| 5,562,688 A | 10/1996 | Riza |
| 5,577,993 A | 11/1996 | Zhu et al. |
| 5,582,577 A | 12/1996 | Lund et al. |
| 5,584,850 A | 12/1996 | Hart et al. |
| 5,601,579 A | 2/1997 | Semertzides |
| 5,620,415 A | 4/1997 | Lucey |
| 5,632,979 A | 5/1997 | Goldberg |
| 5,634,911 A | 6/1997 | Hermann et al. |
| 5,634,936 A | 6/1997 | Linden |
| 5,634,937 A | 6/1997 | Mollenauer et al. |
| 5,636,645 A | 6/1997 | Ou |
| 5,640,977 A | 6/1997 | Leahy et al. |
| 5,649,550 A | 7/1997 | Crook |
| 5,653,705 A | 8/1997 | de la Torre et al. |
| 5,657,963 A | 8/1997 | Hinchliffe |
| 5,658,272 A | 8/1997 | Hasson |
| 5,658,306 A | 8/1997 | Kieturakis |
| 5,672,168 A | 9/1997 | de la Torre et al. |
| 5,685,854 A | 11/1997 | Green |
| 5,707,703 A | 1/1998 | Rothrum et al. |
| 5,709,664 A | 1/1998 | Vandenbroeck |
| 5,720,730 A | 2/1998 | Blake, III |
| 5,738,628 A | 4/1998 | Sierocuk et al. |
| 5,741,234 A | 4/1998 | Aboul-Hosn |
| 5,741,298 A | 4/1998 | MacLeod |
| 5,743,884 A | 4/1998 | Hasson et al. |
| 5,749,882 A | 5/1998 | Hart et al. |
| 5,755,660 A | 5/1998 | Tyagi |
| 5,769,783 A | 6/1998 | Fowler |
| 5,769,794 A | 6/1998 | Conlan et al. |
| 5,782,812 A | 7/1998 | Hart et al. |
| 5,795,290 A | 8/1998 | Bridges |
| 5,803,919 A | 9/1998 | Hart et al. |
| 5,803,921 A | 9/1998 | Bonadio |
| 5,807,350 A | 9/1998 | Diaz |
| 5,810,721 A | 9/1998 | Mueller et al. |
| 5,813,409 A | 9/1998 | Leahy et al. |
| 5,814,026 A | 9/1998 | Yoon |
| 5,817,062 A | 10/1998 | Flom |
| 5,820,555 A | 10/1998 | Mueller |
| 5,832,925 A | 11/1998 | Rothrum |
| 5,848,992 A | 12/1998 | Hart et al. |
| 5,853,395 A | 12/1998 | Crook et al. |
| 5,865,728 A | 2/1999 | Moll et al. |
| 5,871,474 A | 2/1999 | Hermann et al. |
| 5,882,344 A | 3/1999 | Strouder |
| 5,899,208 A | 5/1999 | Bonadio |
| 5,904,703 A | 5/1999 | Gilson |
| 5,906,577 A | 5/1999 | Beane et al. |
| 5,916,232 A | 6/1999 | Hart |
| 5,947,922 A | 9/1999 | MacLeod |
| 5,951,467 A | 9/1999 | Picha et al. |
| 5,957,913 A | 9/1999 | de la Torre et al. |
| 5,964,781 A | 10/1999 | Mollenauer et al. |
| 5,993,485 A | 11/1999 | Beckers |
| 5,994,450 A | 11/1999 | Pearce |
| 5,997,515 A | 12/1999 | de la Torre et al. |
| 6,024,736 A | 2/2000 | de la Torre et al. |
| 6,025,067 A | 2/2000 | Fay |
| 6,033,426 A * | 3/2000 | Kaji .......... A61B 17/3423 600/207 |
| 6,033,428 A | 3/2000 | Sardella |
| 6,036,685 A | 3/2000 | Mueller |
| 6,042,573 A | 3/2000 | Lucey |
| 6,048,309 A | 4/2000 | Flom et al. |
| 6,059,816 A | 5/2000 | Moenning |
| 6,077,288 A * | 6/2000 | Shimomura ....... A61B 17/3423 604/167.01 |
| 6,099,506 A | 8/2000 | Macoviak et al. |
| 6,110,154 A | 8/2000 | Shimomura et al. |
| 6,123,689 A | 9/2000 | To |
| 6,142,935 A | 11/2000 | Flom et al. |
| 6,142,936 A | 11/2000 | Beane et al. |
| 6,149,642 A | 11/2000 | Gerhart et al. |
| 6,150,608 A | 11/2000 | Wambeke |
| 6,159,182 A | 12/2000 | Davis |
| 6,162,172 A | 12/2000 | Cosgrove et al. |
| 6,162,196 A | 12/2000 | Hart et al. |
| 6,162,206 A | 12/2000 | Bindokas |
| 6,163,949 A | 12/2000 | Neuenschwander |
| 6,164,279 A | 12/2000 | Tweedle |
| 6,171,282 B1 | 1/2001 | Ragsdale |
| 6,183,486 B1 | 2/2001 | Snow et al. |
| 6,238,373 B1 | 5/2001 | de la Torre et al. |
| 6,254,533 B1 | 7/2001 | Fadem et al. |
| 6,254,534 B1 | 7/2001 | Butler et al. |
| 6,258,065 B1 | 7/2001 | Dennis |
| 6,315,770 B1 | 11/2001 | de la Torre et al. |
| 6,319,246 B1 | 11/2001 | de la Torre et al. |
| 6,322,541 B2 | 11/2001 | West |
| 6,328,730 B1 | 12/2001 | Harkrider, Jr. |
| 6,346,074 B1 | 2/2002 | Roth |
| 6,382,211 B1 | 5/2002 | Crook |
| 6,420,475 B1 | 7/2002 | Chen |
| 6,440,063 B1 | 8/2002 | Beane |
| 6,450,983 B1 | 9/2002 | Rambo |
| 6,454,783 B1 | 9/2002 | Piskun |
| 6,464,686 B1 | 10/2002 | O'Hara et al. |
| 6,485,435 B1 | 11/2002 | Bakal |
| 6,485,467 B1 | 11/2002 | Crook et al. |
| 6,488,620 B1 | 12/2002 | Segermark et al. |
| 6,533,734 B1 | 3/2003 | Corley, III et al. |
| 6,551,270 B1 | 4/2003 | Bimbo et al. |
| 6,554,793 B1 | 4/2003 | Pauker |
| 6,569,119 B1 | 5/2003 | Haberland et al. |
| 6,578,577 B2 | 6/2003 | Bonadio et al. |
| 6,582,364 B2 | 6/2003 | Butler et al. |
| 6,589,167 B1 | 7/2003 | Shimonmura |
| 6,589,211 B1 | 7/2003 | MacLeod |
| 6,607,504 B2 | 8/2003 | Haarala |
| 6,613,952 B2 | 9/2003 | Rambo |
| 6,623,426 B2 | 9/2003 | Bonadio et al. |
| 6,706,050 B1 | 3/2004 | Giannadakis |
| 6,714,298 B2 | 3/2004 | Ryer |
| 6,723,044 B2 | 4/2004 | Pulford |

(56) References Cited

U.S. PATENT DOCUMENTS

| | | |
|---|---|---|
| 6,793,621 B2 | 9/2004 | Butler et al. |
| 6,796,940 B2 | 9/2004 | Bonadio et al. |
| 6,797,765 B2 | 9/2004 | Pearce |
| 6,814,078 B2 | 11/2004 | Crook |
| 6,814,700 B1 | 11/2004 | Mueller et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,866,861 B1 | 3/2005 | Luhman |
| 6,884,253 B1 | 4/2005 | McFarlane |
| 6,902,541 B2 | 6/2005 | McNally et al. |
| 6,908,430 B2 | 6/2005 | Caldwell |
| 6,916,331 B2 | 7/2005 | Mollenauer et al. |
| 6,936,037 B2 | 8/2005 | Bubb |
| 6,939,296 B2 | 9/2005 | Ewers |
| 6,945,932 B1 | 9/2005 | Caldwell et al. |
| 6,958,037 B2 | 10/2005 | Ewers |
| 6,979,324 B2 | 12/2005 | Bybordi |
| 7,008,377 B2 | 3/2006 | Beane |
| 7,052,454 B2 | 5/2006 | Taylor |
| 7,081,089 B2 | 7/2006 | Bonadio et al. |
| 7,083,626 B2 | 8/2006 | Hart et al. |
| 7,112,185 B2 | 9/2006 | Hart et al. |
| 7,118,528 B1 | 10/2006 | Piskun |
| 7,153,319 B1 | 12/2006 | Haberland et al. |
| 7,195,590 B2 | 3/2007 | Butler et al. |
| 7,297,106 B2 * | 11/2007 | Yamada ............. A61B 17/0293 600/208 |
| 7,300,399 B2 | 11/2007 | Bonadio et al. |
| 7,344,547 B2 | 3/2008 | Piskun |
| 7,445,597 B2 | 11/2008 | Butler et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,749,415 B2 | 7/2010 | Brustad et al. |
| 7,867,164 B2 | 1/2011 | Butler et al. |
| 7,998,068 B2 | 8/2011 | Bonadio et al. |
| 8,012,088 B2 | 9/2011 | Butler et al. |
| 8,021,296 B2 | 9/2011 | Bonadio et al. |
| 8,157,817 B2 | 4/2012 | Bonadio et al. |
| 8,187,178 B2 | 5/2012 | Bonadio et al. |
| 8,317,691 B2 | 11/2012 | Bonadio et al. |
| 8,375,955 B2 | 2/2013 | Desai et al. |
| 8,475,490 B2 * | 7/2013 | Hess ........................ A61B 1/32 606/201 |
| 2001/0037053 A1 | 11/2001 | Bonadio et al. |
| 2001/0039430 A1 | 11/2001 | Dubrul et al. |
| 2001/0047188 A1 | 11/2001 | Bonadio et al. |
| 2002/0002324 A1 | 1/2002 | McManus |
| 2002/0010389 A1 | 1/2002 | Butler et al. |
| 2002/0038077 A1 | 3/2002 | de la Torre et al. |
| 2002/0072762 A1 | 6/2002 | Bonadio et al. |
| 2002/0111536 A1 | 8/2002 | Cuschieri et al. |
| 2003/0028179 A1 | 2/2003 | Piskun |
| 2003/0078478 A1 | 4/2003 | Bonadio et al. |
| 2003/0139756 A1 | 7/2003 | Brustad |
| 2003/0187376 A1 | 10/2003 | Rambo |
| 2003/0192553 A1 | 10/2003 | Rambo |
| 2003/0225392 A1 | 12/2003 | McMichael |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049100 A1 | 3/2004 | Butler |
| 2004/0068232 A1 | 4/2004 | Hart et al. |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor |
| 2004/0143158 A1 | 7/2004 | Hart et al. |
| 2004/0154624 A1 | 8/2004 | Bonadio et al. |
| 2004/0215063 A1 | 10/2004 | Bonadio et al. |
| 2004/0230161 A1 | 11/2004 | Zeiner |
| 2004/0249248 A1 | 12/2004 | Bonadio et al. |
| 2004/0260244 A1 | 12/2004 | Piechowicz et al. |
| 2005/0020884 A1 | 1/2005 | Hart et al. |
| 2005/0033246 A1 | 2/2005 | Ahlberg |
| 2005/0059865 A1 | 3/2005 | Kahle |
| 2005/0065475 A1 | 3/2005 | Hart et al. |
| 2005/0065543 A1 | 3/2005 | Kahle |
| 2005/0090713 A1 | 4/2005 | Gozales |
| 2005/0090716 A1 | 4/2005 | Bonadio et al. |
| 2005/0090717 A1 | 4/2005 | Bonadio et al. |
| 2005/0131349 A1 | 6/2005 | Albrecht |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0222582 A1 | 10/2005 | Wenchell |
| 2005/0240082 A1 | 10/2005 | Bonadio et al. |
| 2005/0241647 A1 | 11/2005 | Nguyen |
| 2005/0267419 A1 | 12/2005 | Smith |
| 2005/0277946 A1 | 12/2005 | Greenhalgh |
| 2005/0288558 A1 | 12/2005 | Ewers |
| 2005/0288634 A1 | 12/2005 | O'Herron |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker |
| 2006/0047284 A1 | 3/2006 | Gresham |
| 2006/0047293 A1 | 3/2006 | Haberland et al. |
| 2006/0106402 A1 | 5/2006 | McLucas |
| 2006/0149306 A1 | 7/2006 | Hart et al. |
| 2006/0161050 A1 | 7/2006 | Butler et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0258899 A1 | 11/2006 | Gill et al. |
| 2006/0264706 A1 | 11/2006 | Piskun |
| 2007/0004968 A1 | 1/2007 | Bonadio et al. |
| 2007/0049966 A1 | 3/2007 | Bonadio et al. |
| 2007/0093695 A1 | 4/2007 | Bonadio et al. |
| 2007/0118175 A1 | 5/2007 | Butler et al. |
| 2007/0185387 A1 | 8/2007 | Albrecht et al. |
| 2007/0203398 A1 | 8/2007 | Bonadio et al. |
| 2007/0255219 A1 | 11/2007 | Vaugh et al. |
| 2007/0299387 A1 | 12/2007 | Williams et al. |
| 2008/0027476 A1 | 1/2008 | Piskun |
| 2008/0097162 A1 | 4/2008 | Bonadio et al. |
| 2008/0097163 A1 | 4/2008 | Butler et al. |
| 2008/0255519 A1 | 10/2008 | Piskun et al. |
| 2008/0281161 A1 | 11/2008 | Albrecht et al. |
| 2008/0281162 A1 | 11/2008 | Albrecht et al. |
| 2009/0012477 A1 | 1/2009 | Norton et al. |
| 2009/0036745 A1 | 2/2009 | Bonadio et al. |
| 2009/0069837 A1 | 3/2009 | Bonadio et al. |
| 2009/0149714 A1 | 6/2009 | Bonadio |
| 2009/0187079 A1 | 7/2009 | Albrecht et al. |
| 2009/0292176 A1 | 11/2009 | Bonadio et al. |
| 2009/0326330 A1 | 12/2009 | Bonadio et al. |
| 2010/0063362 A1 | 3/2010 | Bonadio et al. |
| 2010/0063364 A1 | 3/2010 | Bonadio et al. |
| 2010/0081880 A1 | 4/2010 | Widenhouse et al. |
| 2010/0113886 A1 | 5/2010 | Piskun et al. |
| 2010/0204548 A1 | 8/2010 | Bonadio et al. |
| 2010/0217087 A1 | 8/2010 | Bonadio et al. |

FOREIGN PATENT DOCUMENTS

| | | |
|---|---|---|
| DE | 296 00 939 | 6/1998 |
| EP | 0113520 | 7/1984 |
| EP | 0142262 | 5/1985 |
| EP | 0537768 | 4/1993 |
| EP | 0950376 | 10/1999 |
| EP | 1118657 | 7/2001 |
| EP | 1312318 | 5/2003 |
| FR | 1456623 | 9/1966 |

(56) References Cited

FOREIGN PATENT DOCUMENTS

| | | |
|---|---|---|
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1496696 | 12/1977 |
| GB | 2071502 | 9/1981 |
| GB | 2255019 | 10/1992 |
| GB | 2275420 | 8/1994 |
| JP | 10-108868 | 4/1998 |
| JP | 11-290327 | 10/1999 |
| JP | 2001-61850 | 3/2001 |
| JP | 2002-28163 | 1/2002 |
| JP | 2004-509659 | 4/2004 |
| JP | 2004-195037 | 7/2004 |
| SU | 1342485 | 1/1997 |
| WO | WO 86/06272 | 11/1986 |
| WO | WO 92/11880 | 7/1992 |
| WO | WO 92/21292 | 12/1992 |
| WO | WO 93/05740 | 4/1993 |
| WO | WO 95/05207 | 2/1995 |
| WO | WO 95/07056 | 3/1995 |
| WO | WO 95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/32514 | 9/1997 |
| WO | WO 97/32515 | 9/1997 |
| WO | WO 98/35614 | 8/1998 |
| WO | WO 98/48724 | 11/1998 |
| WO | WO 99/03416 | 1/1999 |
| WO | WO 99/25268 | 5/1999 |
| WO | WO 99/29250 | 6/1999 |
| WO | WO 00/32116 | 6/2000 |
| WO | WO 00/32117 | 6/2000 |
| WO | WO 00/32119 | 6/2000 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |
| WO | WO 01/26558 | 4/2001 |
| WO | WO 01/91652 | 12/2001 |
| WO | WO 01/91653 | 12/2001 |
| WO | WO 02/17800 A2 | 3/2002 |
| WO | WO 02/34108 A2 | 5/2002 |
| WO | WO 03/026512 A1 | 4/2003 |
| WO | WO 03/034908 A3 | 5/2003 |
| WO | WO 03/061480 A1 | 7/2003 |
| WO | WO 03/103548 A1 | 12/2003 |
| WO | WO 2004/026153 A1 | 4/2004 |
| WO | WO 2004/030547 A1 | 4/2004 |
| WO | WO 2005/009257 A2 | 2/2005 |
| WO | WO 2005/034766 A2 | 4/2005 |
| WO | WO 2005/089661 | 9/2005 |
| WO | WO 2006/040748 A1 | 4/2006 |
| WO | WO 2006/059318 | 8/2006 |

OTHER PUBLICATIONS

Extended European Search Report mailed Nov. 15, 2010 in prior U.S. Appl. No. 11/246,909.

International Search Report and Written Opinion in PCT/IE2005/000113 mailed on Feb. 23, 2006.

* cited by examiner

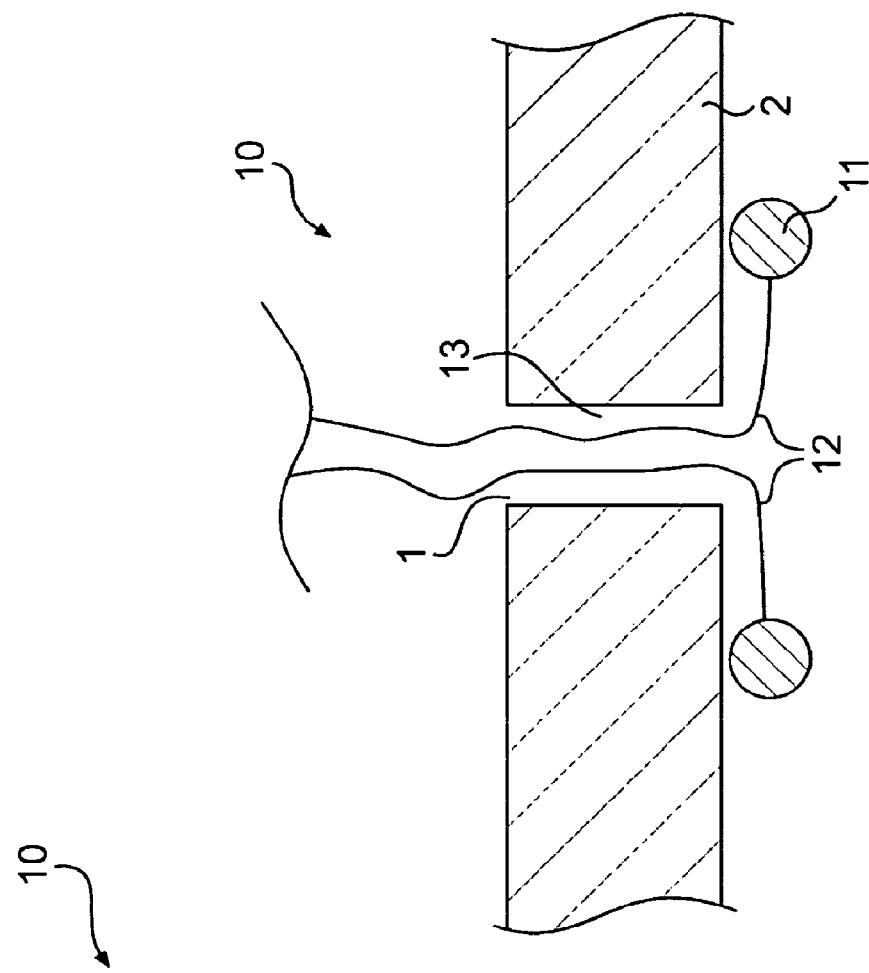
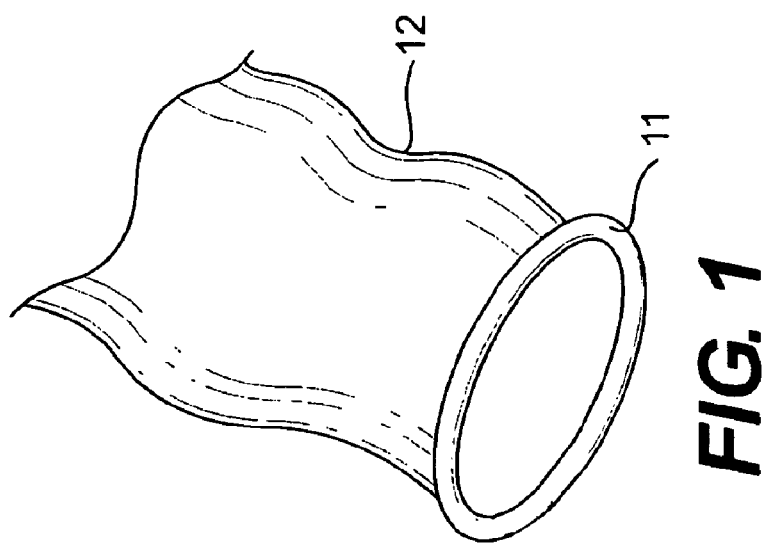

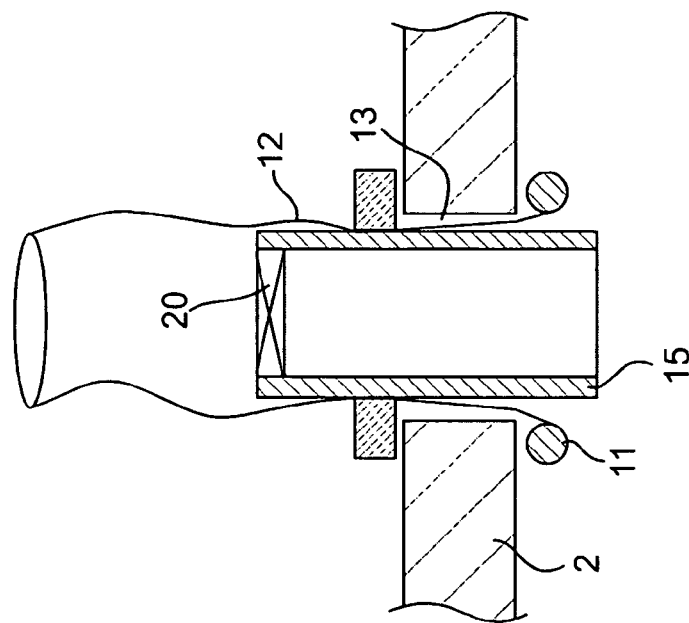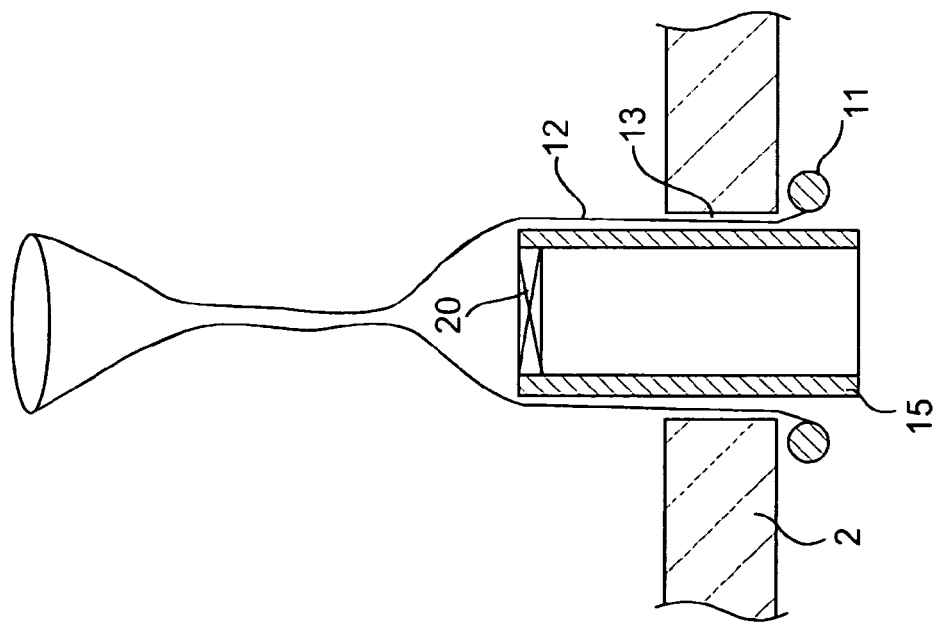

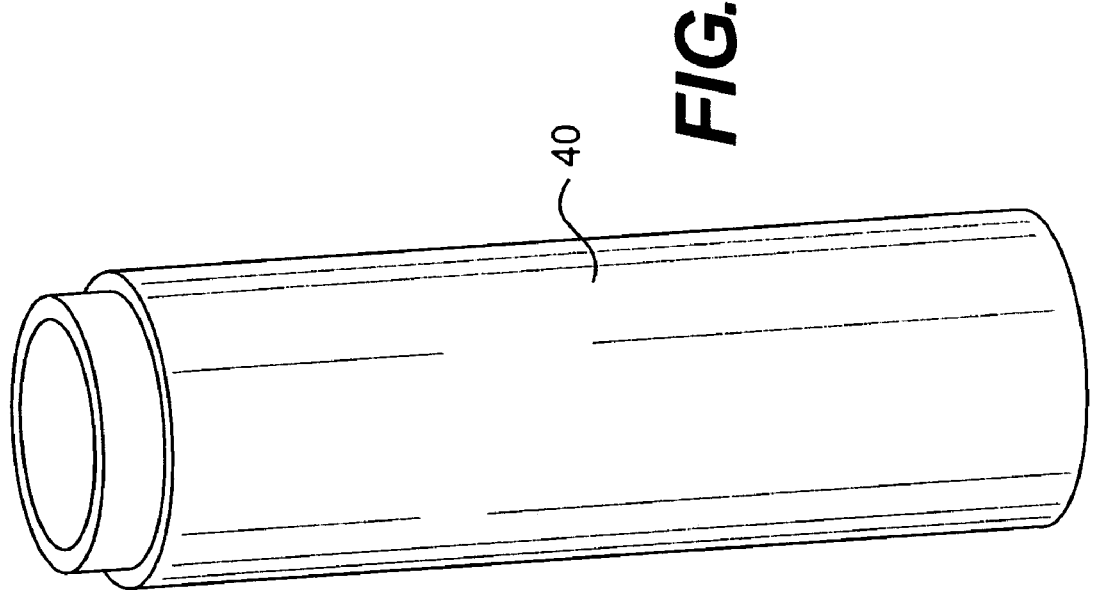

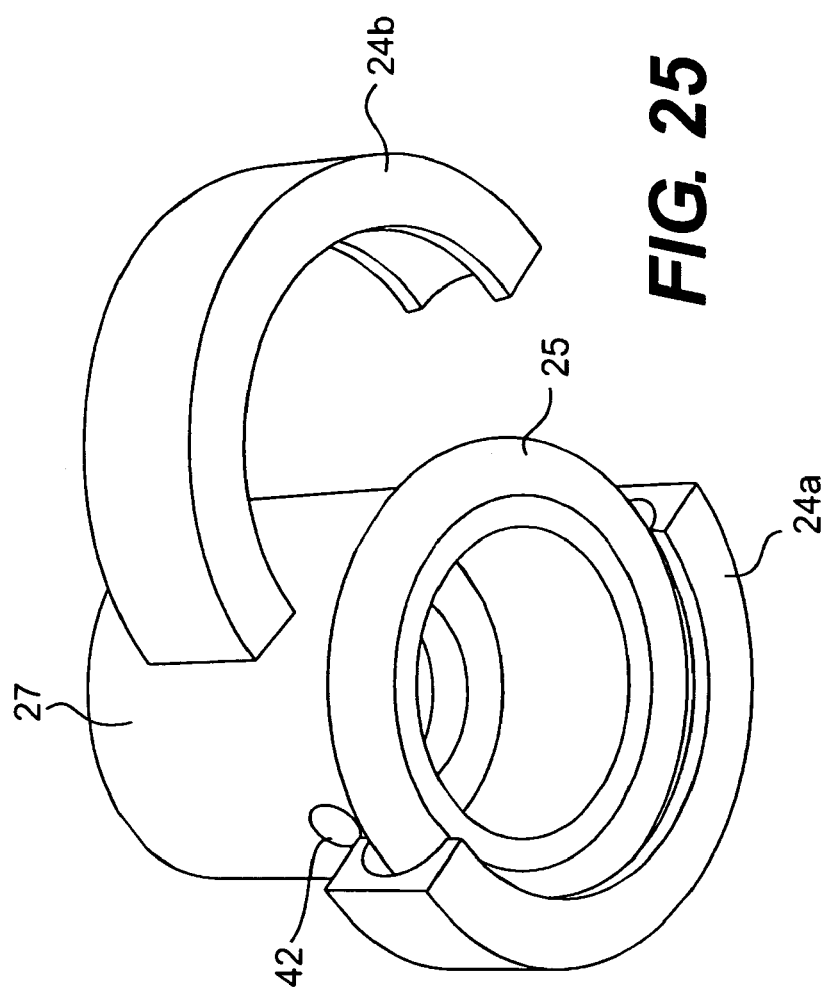

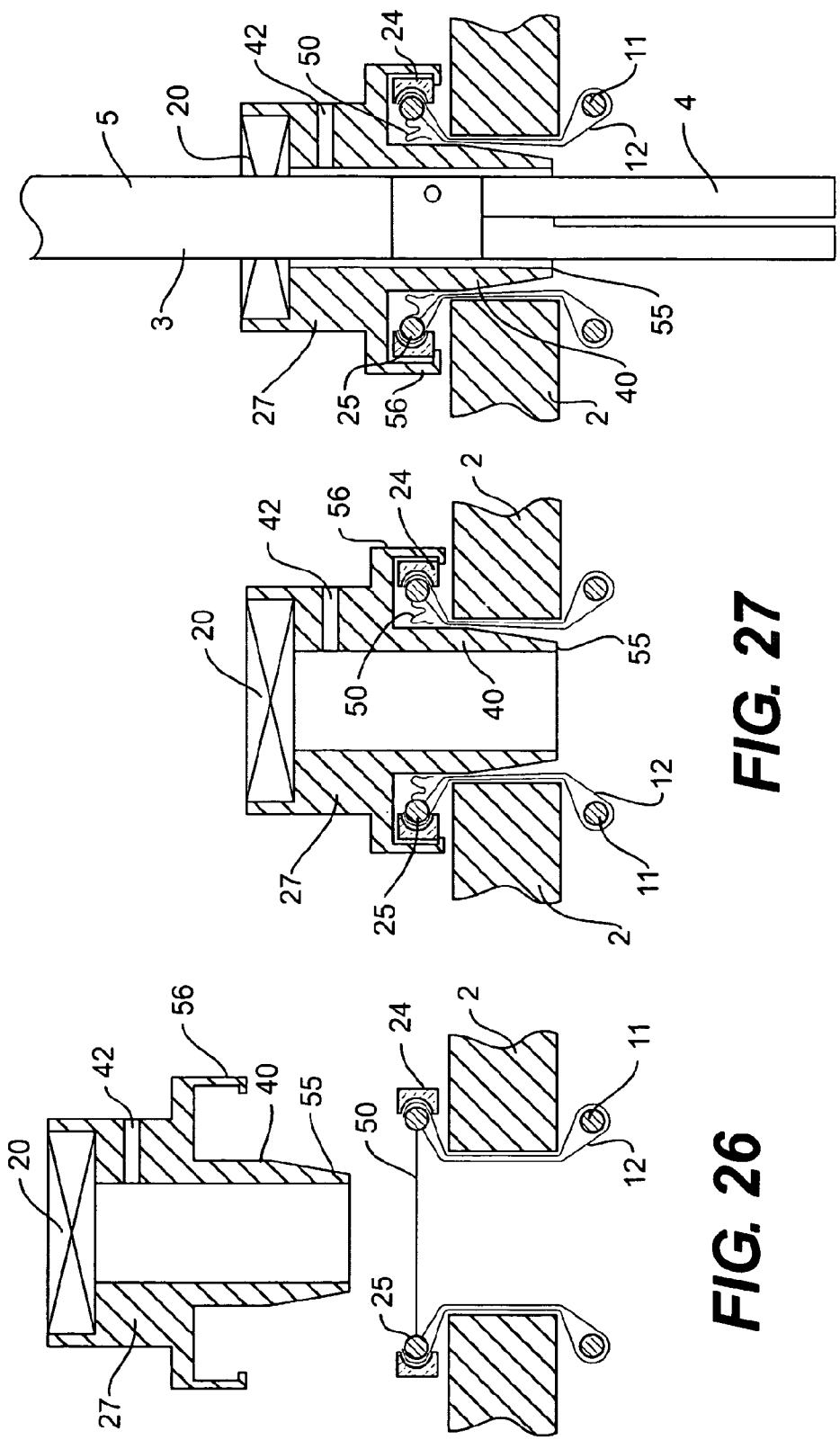

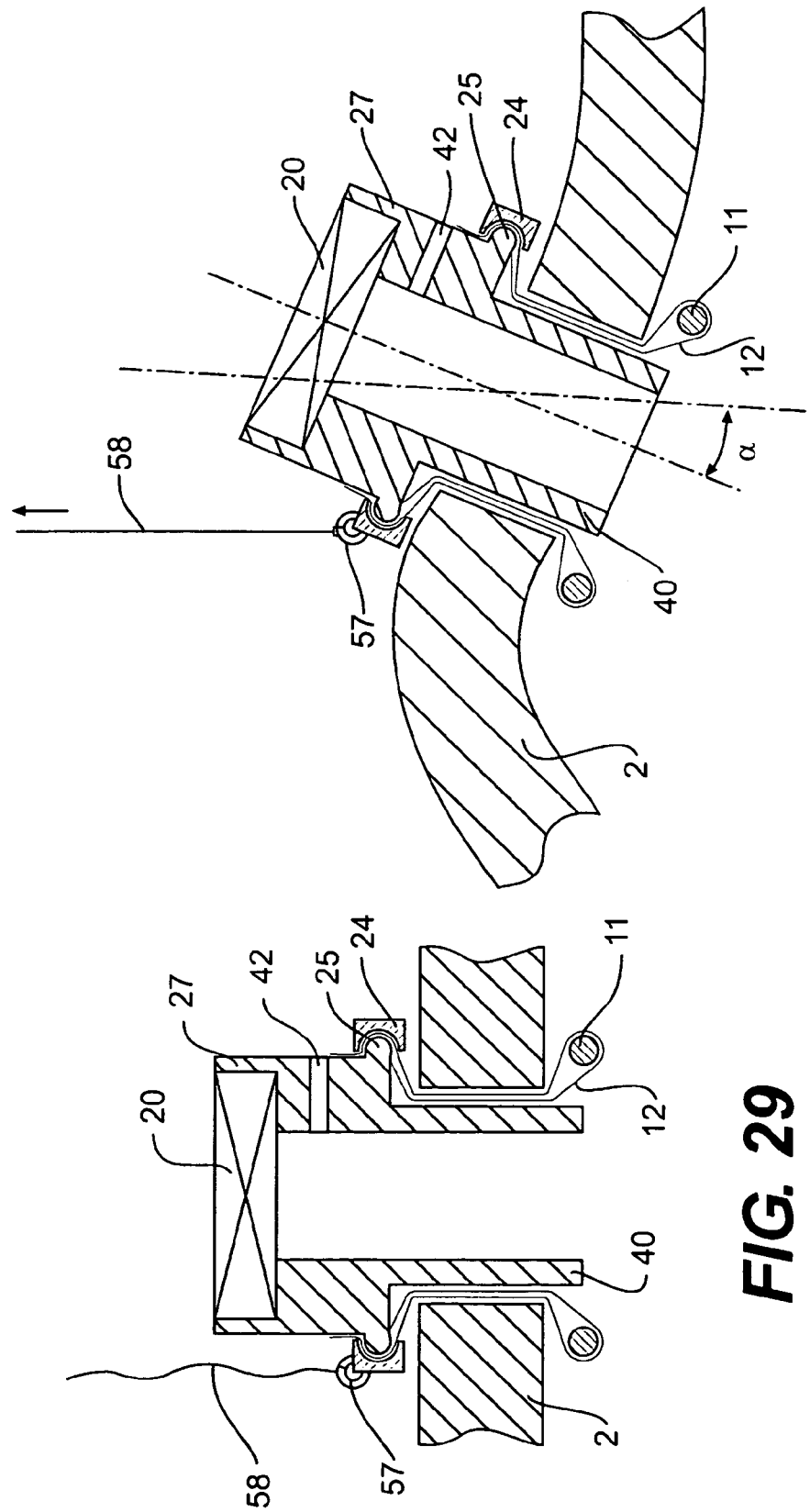

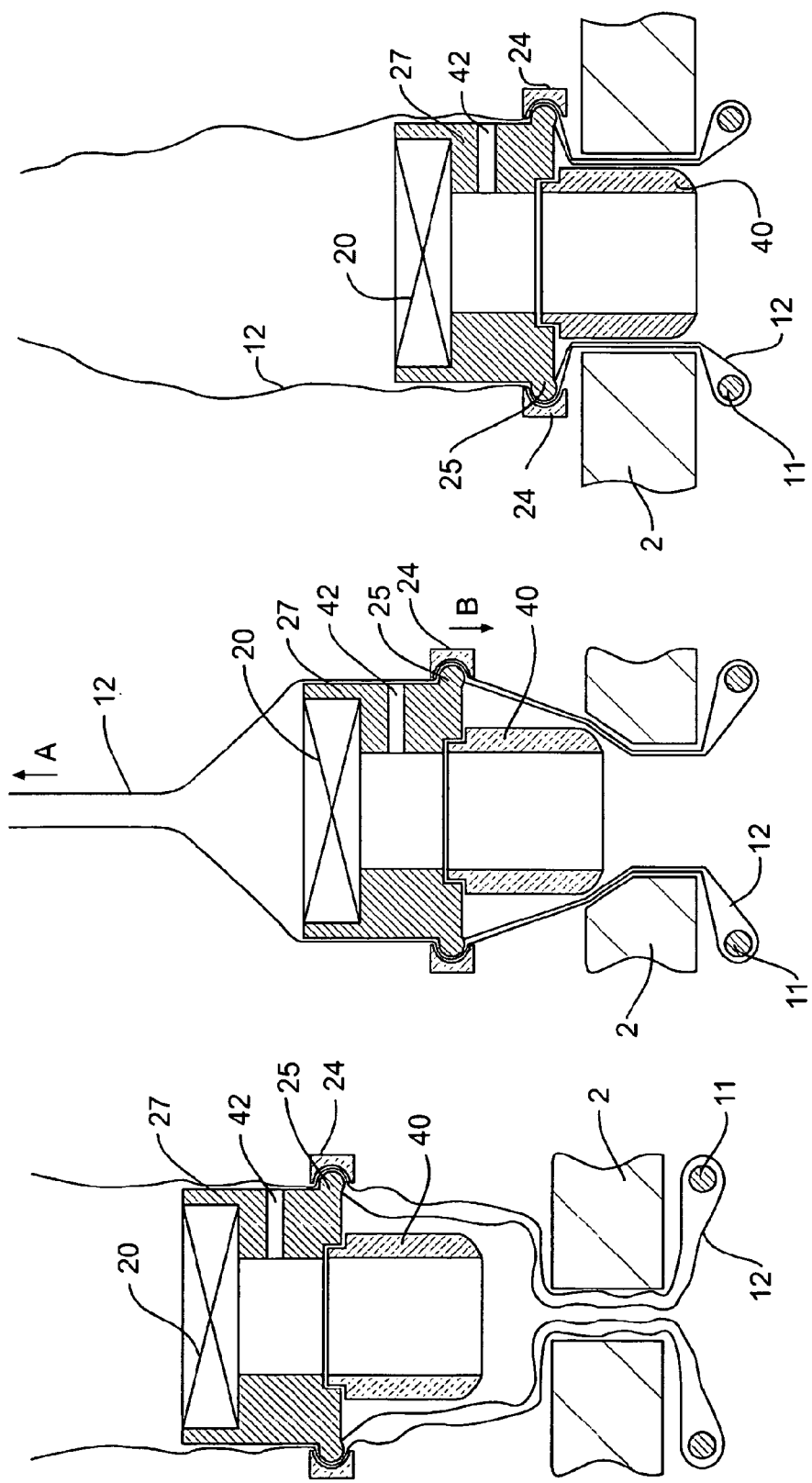

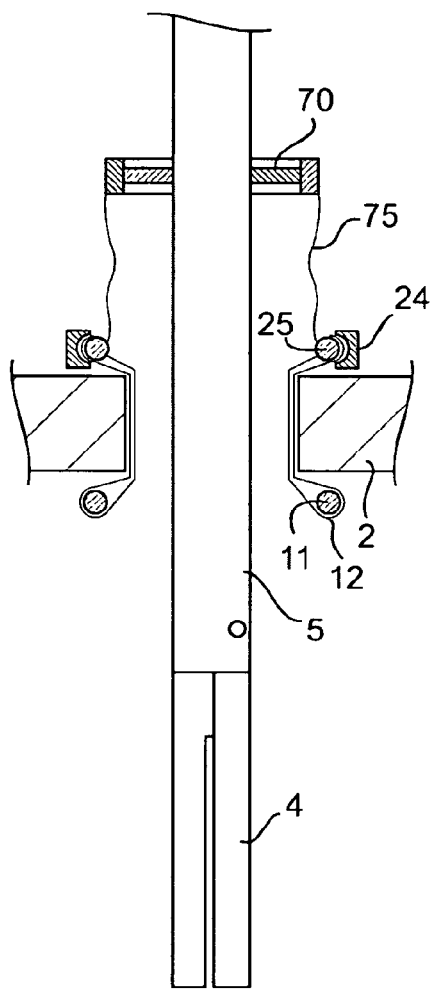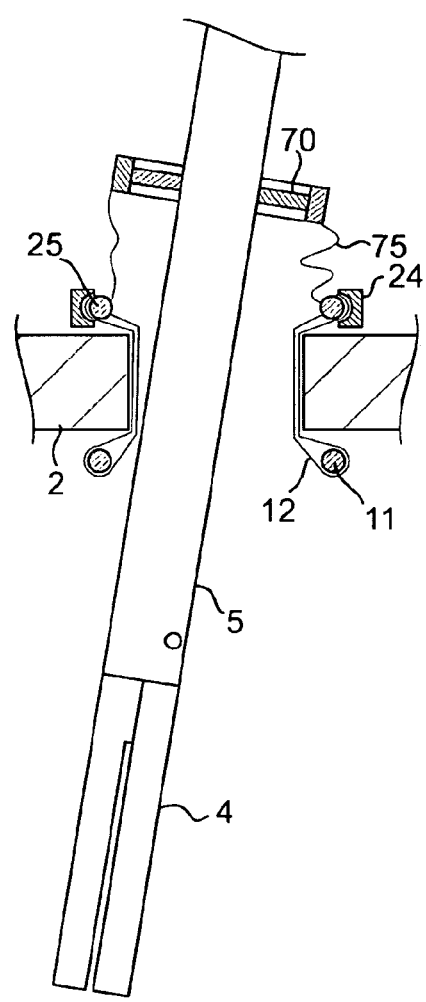
FIG. 41
FIG. 42

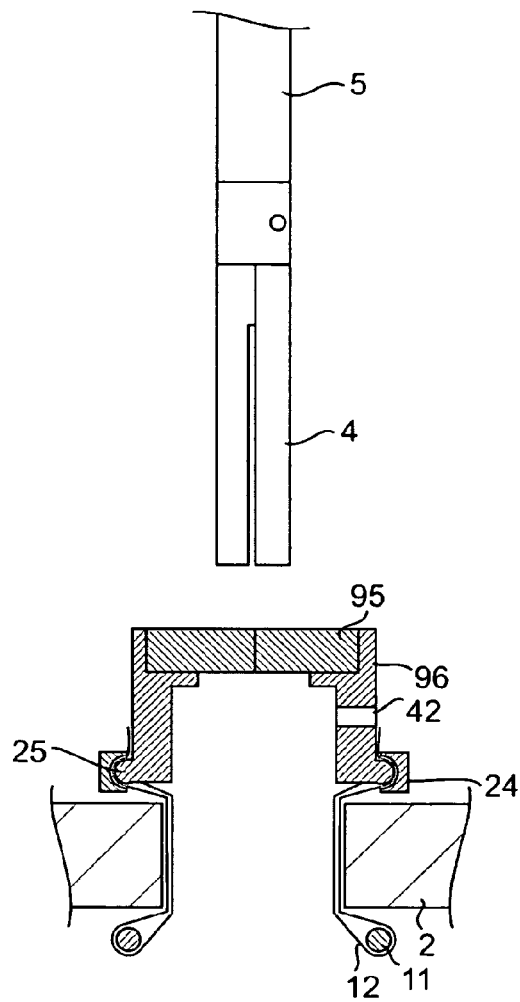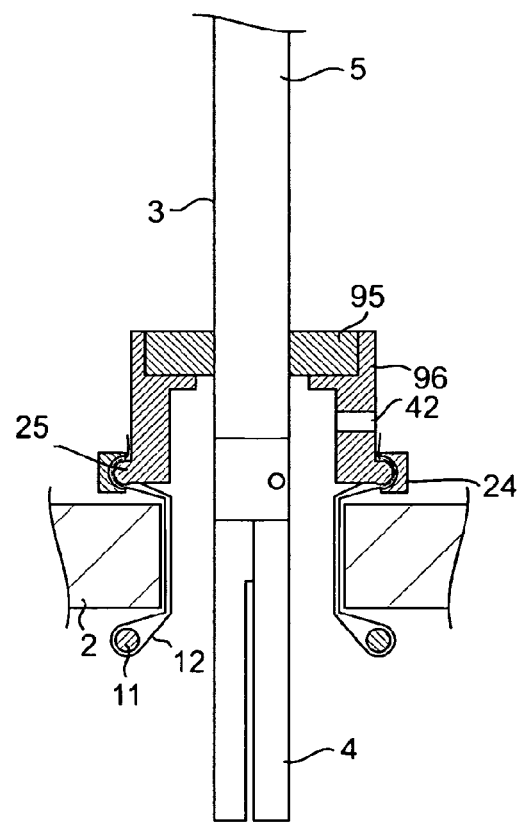
FIG. 57
FIG. 58

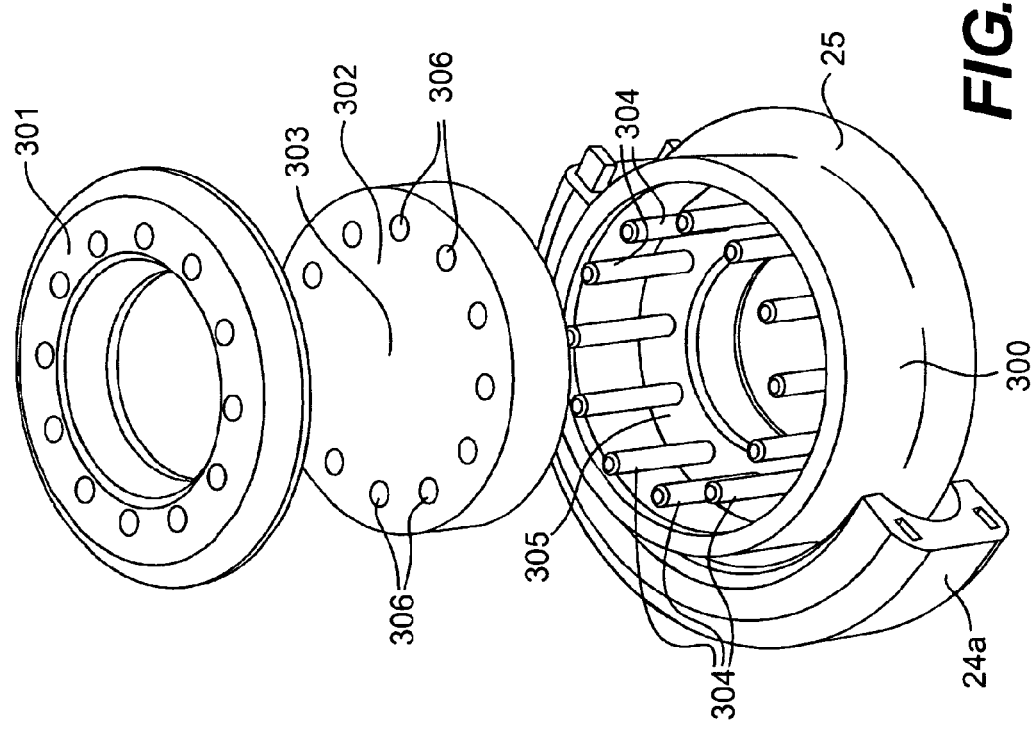

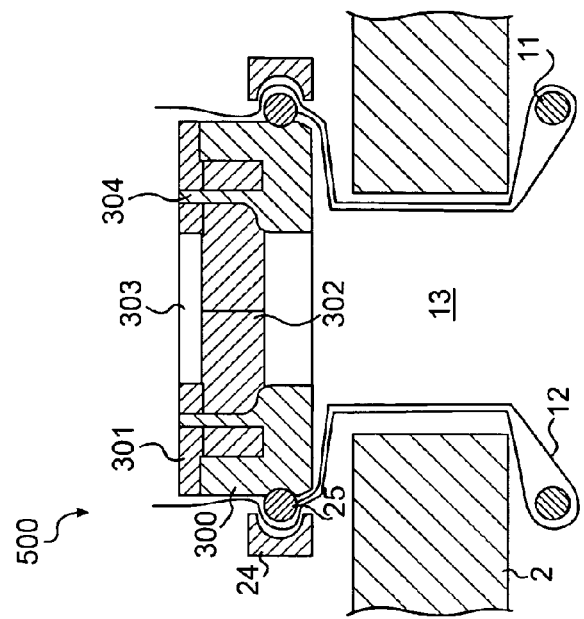
FIG. 58(c)(iii)
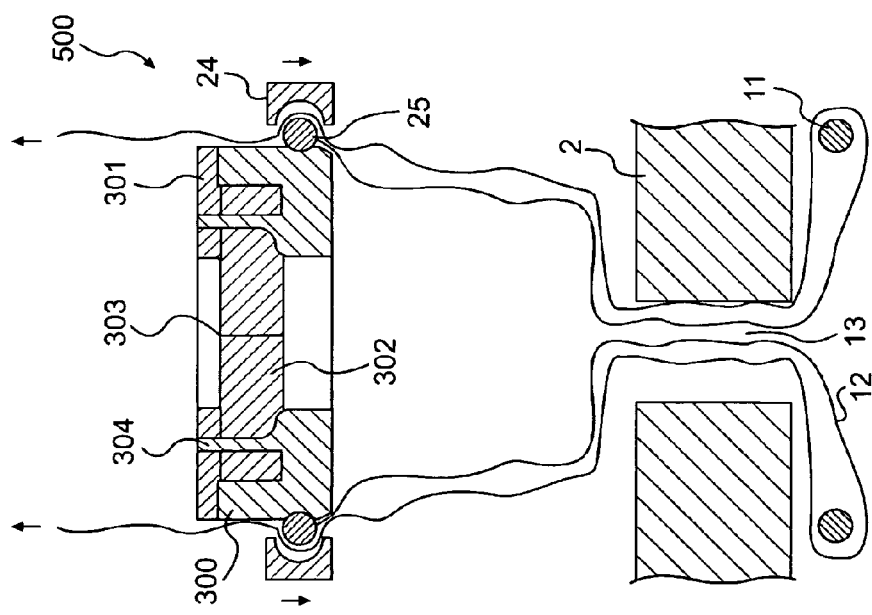
FIG. 58(c)(ii)

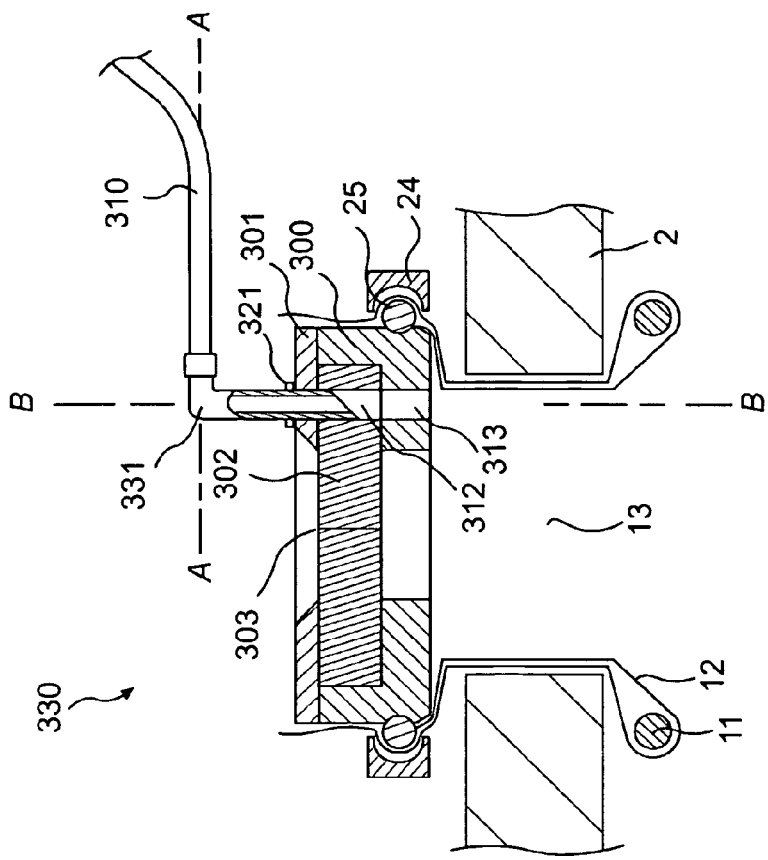
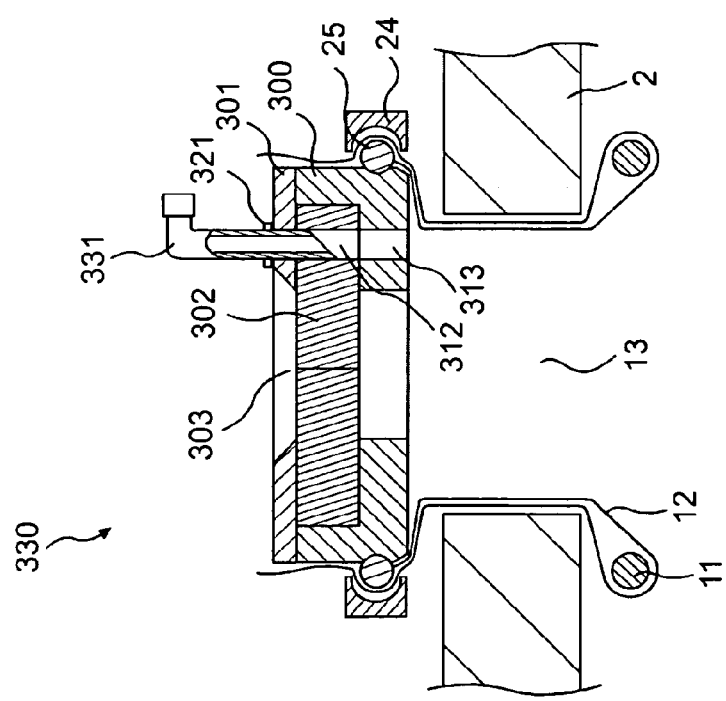
FIG. 58(i)
FIG. 58(h)

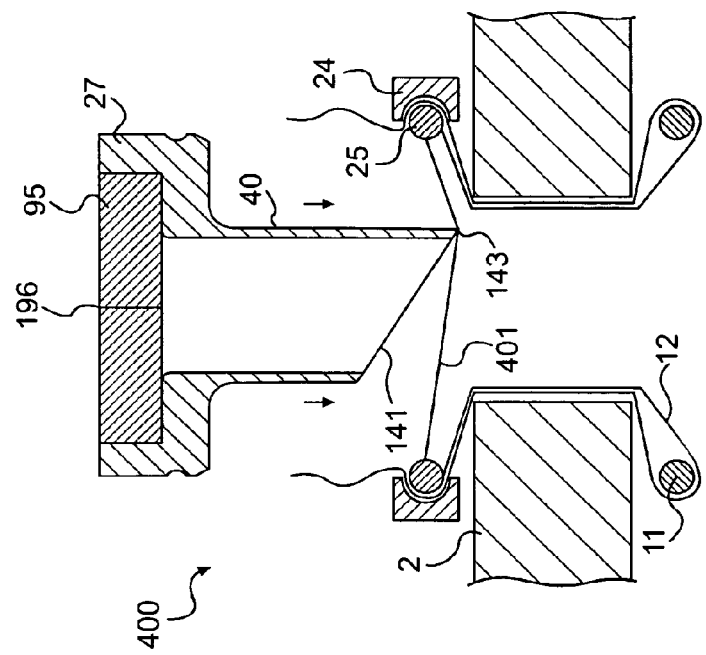
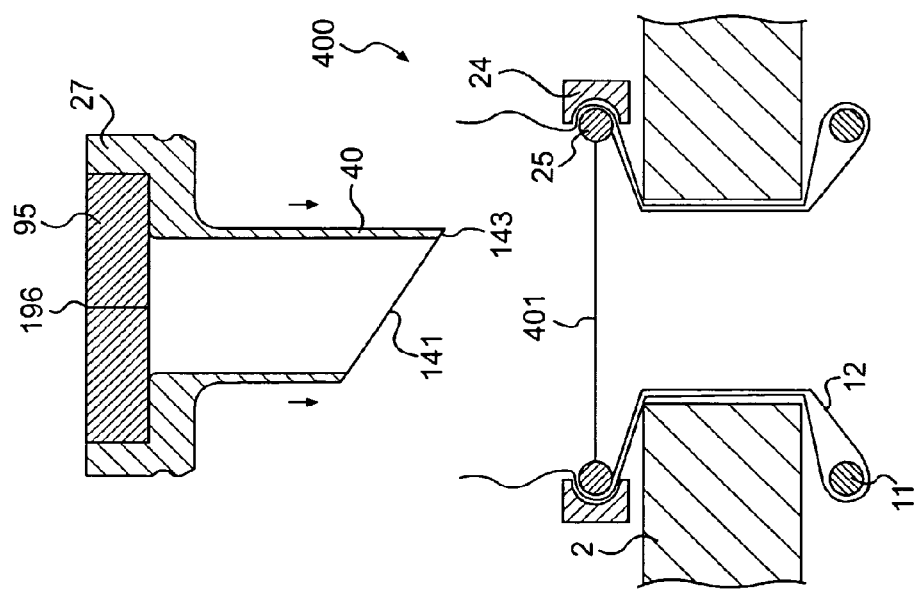
FIG. 70(c)
FIG. 70(d)

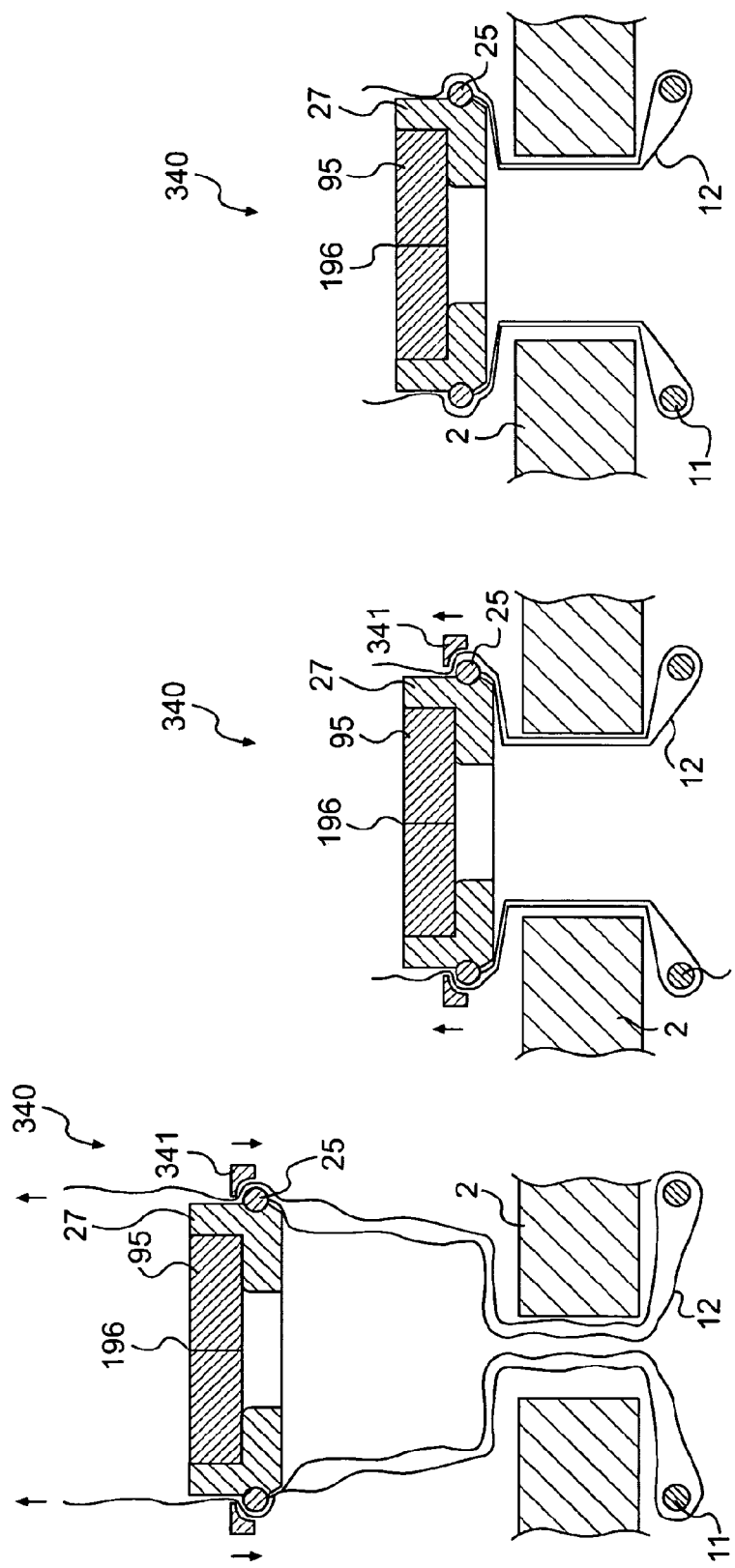

INSTRUMENT ACCESS DEVICE

This application is a Continuation of application Ser. No. 13/175,822, filed on Jul. 1, 2011, now U.S. Pat. No. 8,888,693, which is a Continuation of application Ser. No. 11/246,909, filed on Oct. 11, 2005, now U.S. Pat. No. 7,998,068.

Application Ser. No. 11/246,909, filed on Oct. 11, 2005, is a Continuation-In-Part of U.S. application Ser. No. 10/736,234, filed on Dec. 16, 2003, which claims the benefit of U.S. Provisional Application No. 60/433,603, filed on Dec. 16, 2002, and 60/453,200, filed on Mar. 11, 2003.

Application Ser. No. 11/246,909, filed on Oct. 11, 2005, is also a Continuation-In-Part of U.S. application Ser. No. 10/678,653, filed on Oct. 6, 2003, now U.S. Pat. No. 7,559,893, which is a Continuation-In-Part of Ser. No. 10/133,979, filed on Apr. 29, 2002, now U.S. Pat. No. 6,846,287, which is a Continuation of U.S. application Ser. No. 09/801,826, filed on Mar. 9, 2001, which is a Continuation of PCT/IE99/00122, filed on Dec. 1, 1999. Application Ser. No. 10/678,653, filed on Oct. 6, 2003, is also a Continuation-In-Part of U.S. application Ser. No. 10/374,523, filed on Feb. 27, 2003, now U.S. Pat. No. 7,445,597, which is a Continuation of U.S. application Ser. No. 09/849,341, filed on May 7, 2001, now U.S. Pat. No. 6,582,364, which is a Continuation of U.S. application Ser. No. 09/688,138, filed on Oct. 16, 2000, now U.S. Pat. No. 6,254,534. Application Ser. No. 10/678,653, filed on Oct. 6, 2003, claims the benefit of U.S. Provisional Application No. 60/415,780, filed on Oct. 4, 2002, U.S. Provisional Application No. 60/428,215, filed on Nov. 22, 2002, and U.S. Provisional Application No. 60/490,909, filed on Jul. 30, 2003.

Application Ser. No. 11/246,909, filed on Oct. 11, 2005, is also a Continuation-In-Part of U.S. application Ser. No. 10/665,395, filed on Sep. 22, 2003, now U.S. Pat. No. 7,867,164, which is a Continuation-In-Part of U.S. application Ser. No. 10/374,523, filed on Feb. 27, 2003, now U.S. Pat. No. 7,445,597, which is a Continuation of U.S. application Ser. No. 09/849,341, filed on May 7, 2001, now U.S. Pat. No. 6,582,364, which is a Continuation of U.S. application Ser. No. 09/688,138, filed on Oct. 16, 2000, now U.S. Pat. No. 6,254,534, and claims the benefit of U.S. Provisional Application No. 60/490,909, filed on Jul. 30, 2003.

Application Ser. No. 11/246,909, filed on Oct. 11, 2005, is also a Continuation-In-Part of U.S. application Ser. No. 10/374,523, filed on Feb. 27, 2003, now U.S. Pat. No. 7,445,597, which is a Continuation of U.S. application Ser. No. 09/849,341, filed on May 7, 2001, now U.S. Pat. No. 6,582,364, which is a Continuation of U.S. application Ser. No. 09/688,138, filed on Oct. 16, 2000, now U.S. Pat. No. 6,254,534.

Application Ser. No. 11/246,909, filed on Oct. 11, 2005, is also a Continuation-In-Part of U.S. application Ser. No. 10/133,979, filed on Apr. 29, 2002, now U.S. Pat. No. 6,846,287, which is a Continuation of U.S. application Ser. No. 09/801,826, filed on Mar. 9, 2001, which is a Continuation of PCT/IE99/00122, filed on Dec. 1, 1999.

Application Ser. No. 11/246,909, filed on Oct. 11, 2005, now U.S. Pat. No. 7,998,068, is also a Continuation-In-Part of U.S. application Ser. No. 10/902,440, filed on Jul. 30, 2004, which is a Continuation-In-Part of U.S. application Ser. No. 10/736,234, filed on Dec. 16, 2003, which claims the benefit of U.S. Provisional Application Nos. 60/433,603, filed on Dec. 16, 2002, and 60/453,200, filed on Mar. 11, 2003. Application Ser. No. 10/902,440, filed on Jul. 30, 2004 is also a Continuation-In-Part of U.S. application Ser. No. 10/678,653, filed on Oct. 6, 2003, now U.S. Pat. No. 7,559,893, which is a Continuation-In-Part of Ser. No. 10/133,979, filed on Apr. 29, 2002, now U.S. Pat. No. 6,846,287, which is a Continuation of U.S. application Ser. No. 09/801,826, filed on Mar. 9, 2001, which is a Continuation of PCT/IE99/00122, filed on Dec. 1, 1999. Application Ser. No. 10/678,653, filed on Oct. 6, 2003, also is a Continuation-In-Part of U.S. application Ser. No. 10/374,523, filed on Feb. 27, 2003, now U.S. Pat. No. 7,445,597, which is a Continuation of U.S. application Ser. No. 09/849,341, filed on May 7, 2001, now U.S. Pat. No. 6,582,364, which is a Continuation of U.S. application Ser. No. 09/688,138, filed on Oct. 16, 2000, now U.S. Pat. No. 6,254,534. Application Ser. No. 10/678,653, filed on Oct. 6, 2003 claims the benefit of U.S. Provisional Application No. 60/415,780, filed on Oct. 4, 2002, U.S. Provisional Application No. 60/428,215, filed on Nov. 22, 2002, and U.S. Provisional Application No. 60/490,909, filed on Jul. 30, 2003. Application Ser. No. 10/902,440, filed on Jul. 30, 2004, is also a Continuation-In-Part of U.S. application Ser. No. 10/665,395, filed on Sep. 22, 2003, now U.S. Pat. No. 7,867,164, which is a Continuation-In-Part of U.S. application Ser. No. 10/374,523, filed on Feb. 27, 2003, now U.S. Pat. No. 7,445,597, which is a Continuation of U.S. application Ser. No. 09/849,341, filed on May 7, 2001, now U.S. Pat. No. 6,582,364, which is a Continuation of U.S. application Ser. No. 09/688,138, filed on Oct. 16, 2000, now U.S. Pat. No. 6,254,534, and claims the benefit of U.S. Provisional Application No. 60/490,909, filed on Jul. 30, 2003. Application Ser. No. 10/902,440, filed on Jul. 30, 2004 is also a Continuation-In-Part of U.S. application Ser. No. 10/374,523, filed on Feb. 27, 2003, now U.S. Pat. No. 7,445,597, which is a Continuation of U.S. application Ser. No. 09/849,341, filed on May 7, 2001, now U.S. Pat. No. 6,582,364, which is a Continuation of U.S. application Ser. No. 09/688,138, filed on Oct. 16, 2000, now U.S. Pat. No. 6,254,534. Application Ser. No. 10/902,440, filed on Jul. 30, 2004 is also a Continuation-In-Part of U.S. application Ser. No. 10/315,233, filed on Dec. 10, 2002, which is a Continuation of U.S. application Ser. No. 09/804,552, filed on Mar. 13, 2001, now U.S. Pat. No. 6,578,577, which is a Continuation of PCT/IE99/00123, filed on Dec. 1, 1999. Application Ser. No. 10/902,440, filed on Jul. 30, 2004 is also a Continuation-In-Part of U.S. application Ser. No. 10/133,979, filed on Apr. 29, 2002, now U.S. Pat. No. 6,846,287, which is a Continuation of U.S. application Ser. No. 09/801,826, filed on Mar. 9, 2001, which is a Continuation of PCT/IE99/00122, filed on Dec. 1, 1999. Application Ser. No. 10/902,440, filed on Jul. 30, 2004 also claims the benefit of U.S. Provisional Application No. 60/490,909, filed on Jul. 30, 2003.

Application Ser. No. 11/246,909, filed on Oct. 11, 2005, now U.S. Pat. No. 7,998,068, also claims the benefit of U.S. Provisional Application No. 60/617,094, filed on Oct. 12, 2004, and U.S. Provisional Application No. 60/699,370 filed on Jul. 15, 2005.

Application Ser. No. 11/246,909, filed on Oct. 11, 2005, now U.S. Pat. No. 7,998,068, also claims the benefit of Ireland Application Nos. 990107, 990108, 990109, 990110, 990111, and 990112, filed on Feb. 15, 1999; Ireland Application No. 990416, filed on May 24, 1999; Ireland Application Nos. 980997 and 980999, filed on Dec. 1, 1998; Ireland Application No. 991053, filed on Dec. 16, 1999; Ireland Application No. 990861, filed on Oct. 14, 1999; Ireland Application No. 2002/0754, filed on Sep. 19, 2002; Ireland Application No. 2004/0686, filed on Oct. 11, 2004; International Application Nos. PCT/IE/99/00122 and PCT/

IE/99/00123, filed on Dec. 1, 1999; and European Application No. 00650010, filed on Feb. 18, 2000.

The contents of all of these applications and patents are herein incorporated by reference in their entirety.

INTRODUCTION

Accessing the abdominal cavity while preserving the abdominal wall as much as possible is the aim of any surgical or exploratory procedure. Retraction devices have been used to this end. A retractor can help to expose an operative site and minimise the incision required to carry out the operation.

Minimally invasive surgery is an evolving surgical method that similarly attempts to reduce the size of incisions required, in many cases dramatically. By using a so-called "keyhole" or cannula, the surgeon can gain access with instruments into the abdominal cavity to carry out an operation through a very small series of holes in the abdominal wall. Unlike in the case of "open surgery", primary retraction then must be accomplished by lifting the abdominal wall away from the abdominal viscera. This is most often accomplished with the use of gas in a technique known as insufflation.

The use of a cannula to gain access as a means to see inside the abdomen or introduce surgical instruments has existed since the late 19$^{th}$ century. A cannula comprises a rigid tube, which is inserted through the abdominal wall and is held in place by the tension of the abdominal wall itself around the inserted cannula. The tube must accommodate various thicknesses of abdominal wall and extend significantly both inside and outside the abdomen to avoid slipping out of the incision, and thereby causing gas pressure to escape.

The basic construction of a cannula, however, presents significant limitations in carrying out a surgical procedure. Some of these limitations are as follows.
1. A cannula is held in place, and thus prevents the escape of gas, by tissue tension. This tension can vary depending on the way the cannula is introduced or weaken during the operation under normal surgical manipulation.
2. A cannula extends significantly into the abdominal cavity taking up precious space and interfering with other instruments.
3. A cannula restricts the movement of instruments as they are rigid structures.
4. A rigid cannula presents significant limitations on the design of the instrument which must be passed through the cannula.
5. A cannula takes up a significant space outside of the abdomen, shortening the effective length, and therefore reach, of the surgical instrument.

This invention is directed towards providing an instrument access device which will address at least some of these problems.

STATEMENTS OF INVENTION

According to the invention there is provided an instrument access device comprising:—
   a distal anchoring member for insertion into a wound interior;
   an elongate member extending proximally from the distal anchoring member to retract laterally the sides of a wound opening; and
   an instrument working channel through which an instrument may extend to access the wound interior.

In one embodiment of the invention the device comprises a proximal member for location externally of a wound opening. The proximal member may comprise a ring member. The proximal member may comprise a proximal inner element and a proximal outer element. The elongate member may be led between the proximal inner element and the proximal outer element. The proximal inner element and/or the proximal outer element may comprise a ring element. The proximal outer element may be mounted to the proximal inner element. The proximal outer element may be demountable from the proximal inner element.

In one case the proximal outer element comprises an engagement surface for resting upon the proximal inner element to mount the proximal outer element to the proximal inner element. The engagement surface may comprise a curved surface. The engagement surface may extend in cross-section for substantially a quarter-revolution. The engagement surface may be configured to engage a proximal side of the proximal inner element.

In another case the device comprises a clamp for clamping the instrument working channel in position. The clamp may be configured to clamp the elongate member to the instrument working channel. The clamp may comprise a proximal clamp. The clamp may be defined by the proximal outer element and the proximal inner element. The proximal outer element may comprise a proximal outer ring. The proximal inner element may comprise a proximal inner ring. The proximal inner element may be defined by a portion of the instrument working channel.

In another embodiment the device comprises at least one instrument seal or valve. The seal or valve may comprise a gelatinous elastomeric material. The seal or valve may comprise at least one opening extending therethrough through which an instrument may be extended. The opening may be biased towards a closed configuration. The opening may comprise a pinhole opening.

In one case the seal or valve is piercable to create at least one opening extending therethrough through which an instrument may be extended. The seal or valve may be piercable by an instrument to create an opening extending therethrough.

In another case the seal or valve comprises an insufflation lumen extending therethrough. The longitudinal axis of the insufflation lumen may be substantially parallel to the longitudinal axis of the device.

In another embodiment the device comprises a housing for an instrument seal or valve. The housing may comprise a reception space for receiving an instrument seal or valve. The reception space may have an inlet through which an instrument seal or valve may be located in the reception space. The inlet may face proximally.

In one case the housing comprises a retainer to retain an instrument seal or valve in the reception space. The retainer may comprise a cap for at least partially closing the inlet. The retainer may comprise an opening to facilitate access to an instrument seal or valve in the reception space. The retainer may be substantially annular in shape.

In another case the housing comprises a locator to assist in locating a seal or valve in the reception space. The locator may comprise at least one male member for co-operative association with at least one corresponding female member.

In one embodiment the housing comprises an insufflation lumen extending therethrough. The longitudinal axis of the insufflation lumen may be substantially parallel to the longitudinal axis of the device. The housing insufflation lumen may be aligned with an insufflation lumen of an instrument seal or valve. The device may comprise an insufflation seal or valve for the insufflation lumen. The insufflation seal or valve may be provided at a proximal end of the insufflation lumen. The insufflation seal or valve may be pierceable by an insufflation tube.

In one case the access device comprises an intermediate connector to connect the insufflation lumen in communication with an insufflation tube. The intermediate connector may be configured to connect an insufflation tube in communication with the insufflation lumen with the longitudinal axis of the insufflation tube at a distal end of the insufflation tube inclined relative to the longitudinal axis of the insufflation lumen. The intermediate connector may be configured to connect an insufflation tube in communication with the insufflation lumen with the longitudinal axis of the insufflation tube at a distal end of the insufflation tube substantially perpendicular to the longitudinal axis of the insufflation lumen.

In a further case the housing is mounted to the proximal member. The housing may be mounted to the proximal inner element. The housing may extend distally of the proximal inner element. The housing may be located radially inwardly of the proximal inner element. The housing may be demountable from the proximal inner element.

In one case the device comprises a seal across the proximal inner element. The seal may be pierceable by the housing and/or by the instrument working channel upon mounting of the housing to the proximal inner element.

In a further embodiment the housing is formed integrally with the proximal inner element.

The housing may define the proximal inner element.

In one case the device comprises a sleeve extending from the proximal inner element to the housing. The sleeve may be formed integrally with the elongate member.

In one embodiment the housing at least in part defines the instrument working channel. The instrument working channel may be mounted to the housing. The instrument working channel may be demountable from the housing. In one case the instrument working channel is formed integrally with the housing.

In one embodiment the instrument working channel is defined by a tubular member. The tubular member may be substantially rigid over at least part of its length. The tubular member may define a lumen extending therethrough through which an instrument may be extended. The tubular member may have a distal opening at a distal end of the tubular member. The distal opening may be inclined relative to the longitudinal axis of the tubular member. The plane of the distal opening may be inclined relative to the longitudinal axis of the tubular member. The tubular member may have a low-profile leading end. The leading end may be tapered. The leading end may be tapered to a point. The distal end of the tubular member may be skived.

In another embodiment the instrument working channel is mounted to the proximal member. The instrument working channel may be mounted for controlled movement relative to the proximal member. The device may comprise a sleeve extending between the instrument working channel and the proximal member to mount the instrument working channel to the proximal member.

In one case the elongate member comprises a sleeve. At least a portion of the sleeve may comprise two material layers. The sleeve may be wrapped around the distal anchoring member. The sleeve may be slidably movable relative to the distal anchoring member. The sleeve may comprise a single material layer. An end of the sleeve may be fixed to the distal anchoring member.

In a further case the elongate member extends from the distal anchoring member to at least the proximal member. The elongate member may be slidably movable over at least a portion of the proximal member. The elongate member may be slidably movable over the proximal inner element. An end of the elongate member may be fixed to the proximal member. An end of the elongate member may be fixed to the housing. The elongate member may be fixed to the proximal member at one end, the elongate member may extend from the proximal member to the distal anchoring member to define an inner material layer, and the elongate member may extend from the distal ring anchoring member to the proximal member to define an outer material layer.

In one case the distal anchoring member comprises a distal ring. The distal ring may be formed from an elastomeric material.

The device may comprise at least one proximal handle for manipulating the device, in situ.

In another aspect of the invention there is provided an instrument access device comprising: —
    a distal ring;
    a proximal ring;
    a sleeve having a portion between the distal ring and the proximal ring that includes two material layers; and
    an instrument seal or valve mounted to the proximal ring.

In one embodiment the sleeve is fixed to the proximal ring at one end, the sleeve extends from the proximal ring to the distal ring to define an inner material layer, and the sleeve extends from the distal ring to the proximal ring to define an outer material layer. The sleeve may be slidingly received over a portion of the proximal ring.

In one case the proximal ring comprises an inner proximal ring member and an outer proximal ring member between which the sleeve is led.

The instrument also provides in another aspect an instrument access device comprising: —
    a distal ring;
    a proximal ring;
    a sleeve having a portion between the distal ring and the proximal ring; and
    an instrument seal or valve comprising a gelatinous elastomeric material for receiving an instrument.

The gelatinous elastomeric material may have a pinhole to receive an instrument.

In a further aspect, the invention provides an instrument access device comprising:—
    a distal anchoring member for insertion into a wound interior;
    a proximal member for location externally of a wound opening;
    a sleeve extending in two layers at least between the distal anchoring member and the proximal member; and
    an instrument seal or valve comprising a gelatinous elastomeric material for receiving an instrument.

The invention also provides in another aspect an instrument access device comprising:—
    a distal anchoring member for insertion into a wound interior;
    a proximal member for location externally of a wound opening;
    an elongate member extending at least between the distal anchoring member and the proximal member;
    the proximal member comprising a proximal inner element and a proximal outer element between which the elongate member is led; and
    an instrument seal or valve mounted to the proximal inner element.

According to another aspect of the invention there is provided a method of accessing a wound interior with an instrument, the method comprising the steps of:— inserting a distal anchoring member through an incision, the distal anchoring member having an elongate member attached thereto;

presenting an instrument working channel member to the incision;

pulling the elongate member upwardly relative to the instrument working channel member to at least partially insert the instrument working channel member into the incision; and inserting an instrument through the incision.

In one embodiment the elongate member lies at least in part between the instrument working channel member and the walls of the incision.

In one case the incision is a laparoscopic incision. The sides of the incision may be retracted to a diameter of less than 40 mm. The sides of the incision may be retracted to a diameter of between 3 mm and 35 mm. The sides of the incision may be retracted to a diameter of between 5 mm and 12 mm.

In another case the sides of the incision are retracted to a diameter substantially equal to a diameter of the instrument working channel member.

The sides of the incision may be at least partially retracted by insertion of the instrument working channel member into the incision. The sides of the incision may be at least partially retracted by pulling of the elongate member upwardly relative to the instrument working channel member.

In one case the instrument is a laparoscopic instrument. The instrument may have a diameter of less than 40 mm. The instrument may have a diameter of between 3 mm and 35 mm. The instrument may have a diameter of between 5 mm and 12 mm.

In one case after insertion of the instrument working channel member into the incision, the distal end of the instrument working channel member is located within the wound interior distally of the incision. In another case after insertion of the instrument working channel member into the incision, the distal end of the instrument working channel member is located within the incision proximally of the wound interior.

In one embodiment the leading end of the instrument working channel member is guided into the incision. The instrument working channel member may be configured to automatically guide the leading end into the incision.

The method may comprise the step of sealing the incision. The method may comprise the steps of insufflating the wound interior. The wound interior may be insufflated after insertion of the instrument working channel member into the incision.

In another aspect the invention provides a method of retracting a wound opening, the method comprising the steps of:— inserting a distal anchoring member through a wound opening into a wound interior;

locating a proximal member externally of the wound opening with an elongate member extending at least between the distal anchoring member and the proximal member;

locating a guide member externally of the wound opening;

moving the guide member and the proximal member relative to the elongate member to retract laterally the sides of the wound opening; and removing the guide member while the distal anchoring member, the proximal member and the elongate member remain in position retracting the wound opening.

In one case the elongate member is led between the proximal member and the guide member.

The elongate member may extend in two layers between the proximal member and the distal anchoring member.

In another case the proximal member is moved by pushing the guide member which engages the proximal member.

The invention also provides in a further aspect a method of retracting a wound opening, the method comprising the steps of:— inserting a distal anchoring member through a wound opening into a wound interior;

locating a proximal member externally of the wound opening with an elongate member extending at least between the distal anchoring member and the proximal member;

moving the proximal member relative to the elongate member to retract laterally the sides of the wound opening; and mounting a first seal or valve to the proximal member.

In one embodiment the first seal or valve is mounted to the proximal member after retraction of the wound opening. The first seal or valve may be mounted to the proximal member before retraction of the wound opening.

In one case the method comprises the step of piercing a second seal. The second seal may be pierced upon mounting of the first seal or valve to the proximal member.

In a further aspect of the invention there is provided a method of retracting a wound opening, the method comprising the steps of:— inserting a distal anchoring member through a wound opening into a wound interior;

locating a proximal member externally of the wound opening with an elongate member extending at least between the distal anchoring member and the proximal member; and by means of a single actuation step, moving the proximal member relative to the elongate member to retract laterally the sides of the wound opening.

In one embodiment the entire circumference of the proximal member is moved together relative to the entire circumference of the elongate member.

The proximal member may be pushed distally relative to the elongate member. The elongate member may be pulled proximally relative to the proximal member. The proximal member may be moved relative to the elongate member in a single direction. The proximal member may be moved relative to the elongate member in a direction substantially parallel to the longitudinal axis of the wound opening.

In one case the method comprises the step of gripping the proximal member. The proximal member may be gripped by a single hand of a user. Opposite sides of the proximal member may be gripped by a single hand of a user. The method may comprise the step of gripping the elongate member. The elongate member may be gripped by a single hand of a user. The entire circumference of the elongate member may be gripped by a single hand of a user.

BRIEF DESCRIPTION OF THE DRAWINGS

The invention will be more clearly understood from the following description of some embodiments thereof, given by way of example only, with reference to the accompanying drawings, in which:—

FIG. 1 is a perspective view of a liner part of an instrument access device of the invention;

FIG. 2 is a cross sectional, side view of the liner part of FIG. 1 inserted in an incision;

FIGS. 10 and 11 are views similar to FIGS. 4 and 5 of an alternative tubular member with a proximal valve or seal, in use;

FIG. 20 is a perspective view of one of the tubular members of FIGS. 17 to 19;

FIGS. 24 and 25 are exploded, perspective views of an outer proximal ring and housing part assembly of the access device of the invention;

FIGS. 26 to 28 are cross sectional, side views of another instrument access device of the invention, in use;

FIGS. 29 and 30 are cross sectional, side views of a further instrument access device of the invention, in use;

FIGS. 33 to 37 are cross-sectional, side views of a further instrument access device of the invention;

FIGS. 40 to 42 are cross sectional, side views of another instrument access device of the invention;

FIGS. 56 to 58 are cross sectional, side views of a further instrument access device of the invention;

FIG. 58(a)(ii) is an exploded, perspective view of a part of the device of FIG. 58(a)(i);

FIGS. 58(c)(ii) and 58(c)(iii) are cross-sectional, side views of the device of FIG. 58(a)(i), in use;

FIGS. 58(h) and 58(i) are partially cross-sectional, side views of a further instrument access device according to the invention, in use;

FIGS. 70(a) to 70(f) are cross-sectional, side views of another instrument access device according to the invention, in use;

FIGS. 71 to 73 are cross-sectional, side views of a further instrument access device according to the invention, in use.

DETAILED DESCRIPTION

Figure 5:
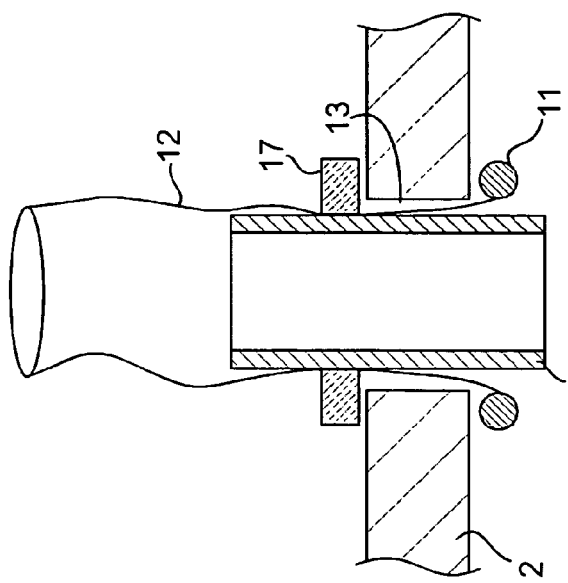
FIG. 5 is a cross-sectional, side view similar to FIG. 4 illustrating clamping or anchoring of the tubular member.
Figure 4:
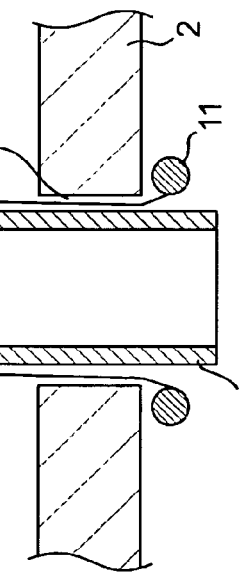
FIG. 4 is a cross sectional, side view of the access device in place in an incision.
Figure 3:
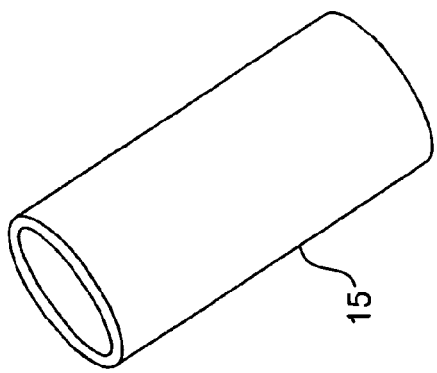
FIG. 3 is a perspective view of a tubular member defining an instrument working channel of the access device.
Figure 7:
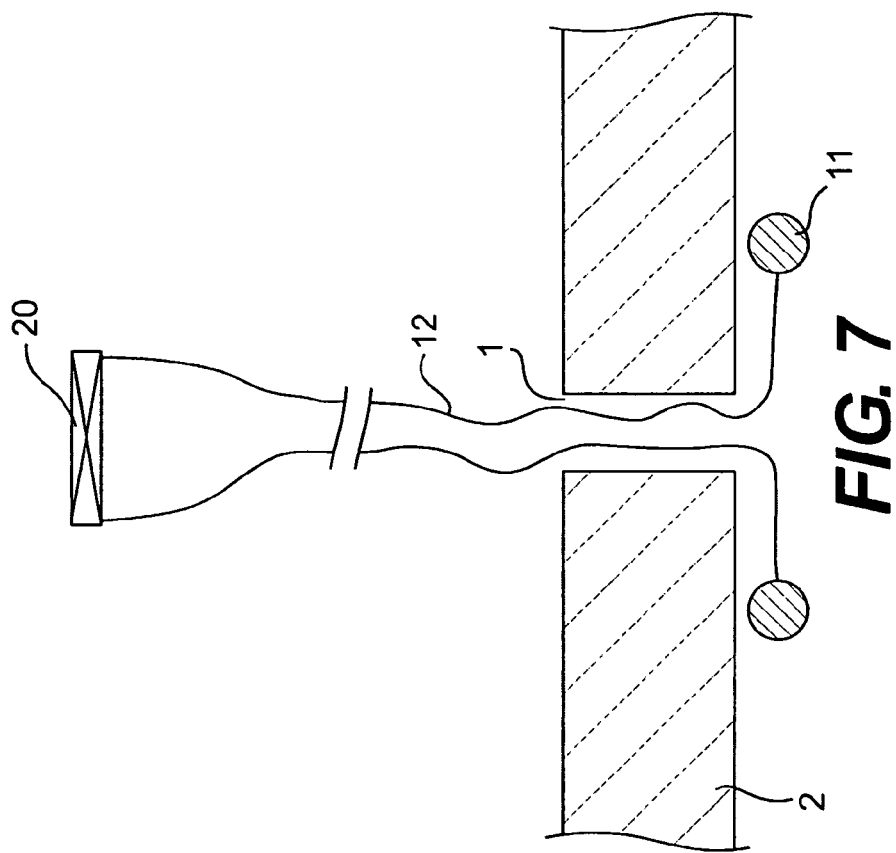
FIGS. 6 and 7 are views similar to FIGS. 1 and 2 of an alternative liner part with a proximal valve or seal.
Figure 6:
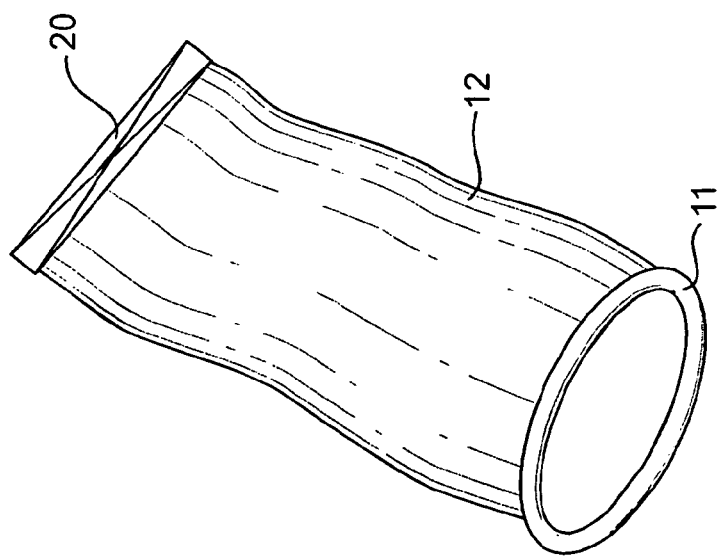
Figure 8:
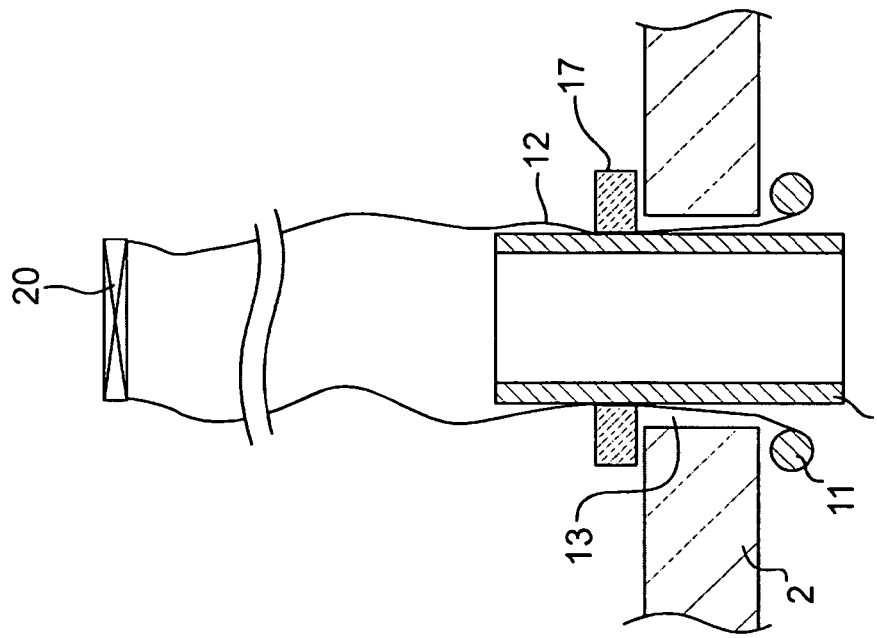
FIGS. 8 and 9 are views similar to FIGS. 4 and 5 with the liner part of FIGS. 6 and 7, in use.
Figure 9:
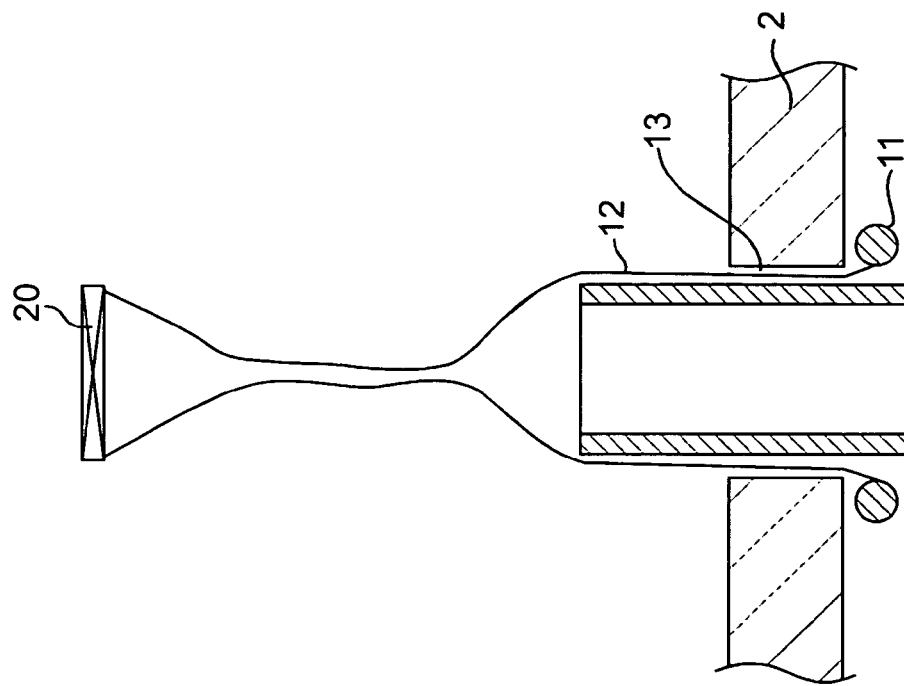

Referring to the drawings there are illustrated various instrument access devices of the invention for an incision 1, for example in an abdominal wall 2. The construction of the various components and their attributes will be explained in detail below. In some cases, the instrument access device is used as a substitute for a conventional rigid tubular cannula. The instrument access devices of the invention may be used to provide access to the abdominal cavity by an instrument 3, which in this case has an operating element 4, such as a surgical stapler, mounted at the distal end of a flexible shaft 5.

It will be noted that the devices have a very low profile, especially with respect to the inside of the incision 1. The devices are positively retained in the incision 1 against pull-out forces. Because of the low profile the shaft 5 of the instrument 3 can begin bending immediately after entering the abdominal cavity. The amount of free space required to manipulate the instrument 3 is minimised. This is in contrast to a conventional cannula, in which the rigid tube of the cannula must be extended significantly into the abdomen to ensure that it remains anchored in the abdomen, otherwise gas pressure may cause it to become dislodged. In conventional systems, because of the cannula length extending into the abdomen, the shaft 5 of the instrument 3 cannot be steered until the steerable section has exited the cannula. Thus, there are severe limitations on the use of such instruments using a conventional cannula. These problems are overcome at least in part using the instrument access devices of the invention.

Referring initially to FIGS. 1 and 2 there is illustrated a liner part 10 of the access device. The liner part 10 comprises a distal anchoring member 11 and an elongate member 12 extending proximally of the distal anchoring member 11.

In this case, the elongate member is provided in the form of a sleeve 12 of flexible, polymeric film material which lines the sides of the wound opening 13, in use. The distal anchoring member 11 in this case comprises a resilient O-ring.

An instrument working channel is in this case defined by a tubular member 15 which may be substantially rigid along at least portion of the length thereof.

In use, a relatively small incision 1 is made in an abdominal wall 2 to form the wound opening 13. A typical length for the incision 1 is in the range of from 12 mm to 30 mm. The resilient distal O-ring 11 is then manipulated into an elongate, oblong shape by squeezing the distal O-ring 11 to facilitate insertion of the distal O-ring 11 through the wound opening 13, until the distal O-ring 11 is fully located within the abdominal cavity and the sleeve 12 lines the wound opening 13. The tubular member 15 is then presented to the wound opening 13 inside the sleeve 12. The sleeve 12 is then pulled upwardly relative to the tubular member 15 to cause the tubular member 15 to enter the wound opening 13 and to cause the distal O-ring 11 to engage with the internal surface of the abdominal wall.

The tubular member 15 is clamped or anchored to the sleeve 12 by a suitable clamp such as a proximal clamp 17.

The use of the tubular member 15 provides an enhanced instrument working channel through the wound opening 13. It assists in preventing collapse of the sides of the wound opening 13. There is less friction as the instrument 3 is inserted and manipulated. Importantly, the tubular member 15 assists in providing a device that has a very low profile with the consequent advantages of maximising the surgeon's freedom of movement.

Any suitable valve or seal or combinations of valves and/or seals may be provided for an instrument. Such valve or valves are generically indicated by an X and by the reference numeral 20 in the drawings. In one arrangement (FIGS. 6 to 9) a valve 20 is provided at a proximal end of the sleeve 12. In another arrangement a valve 20 is provided at a proximal end of the tubular member 15 (FIGS. 10 and 11). Indeed valves 20 may be provided both on the sleeve 2 and on the tubular member 15.

Figure 12:
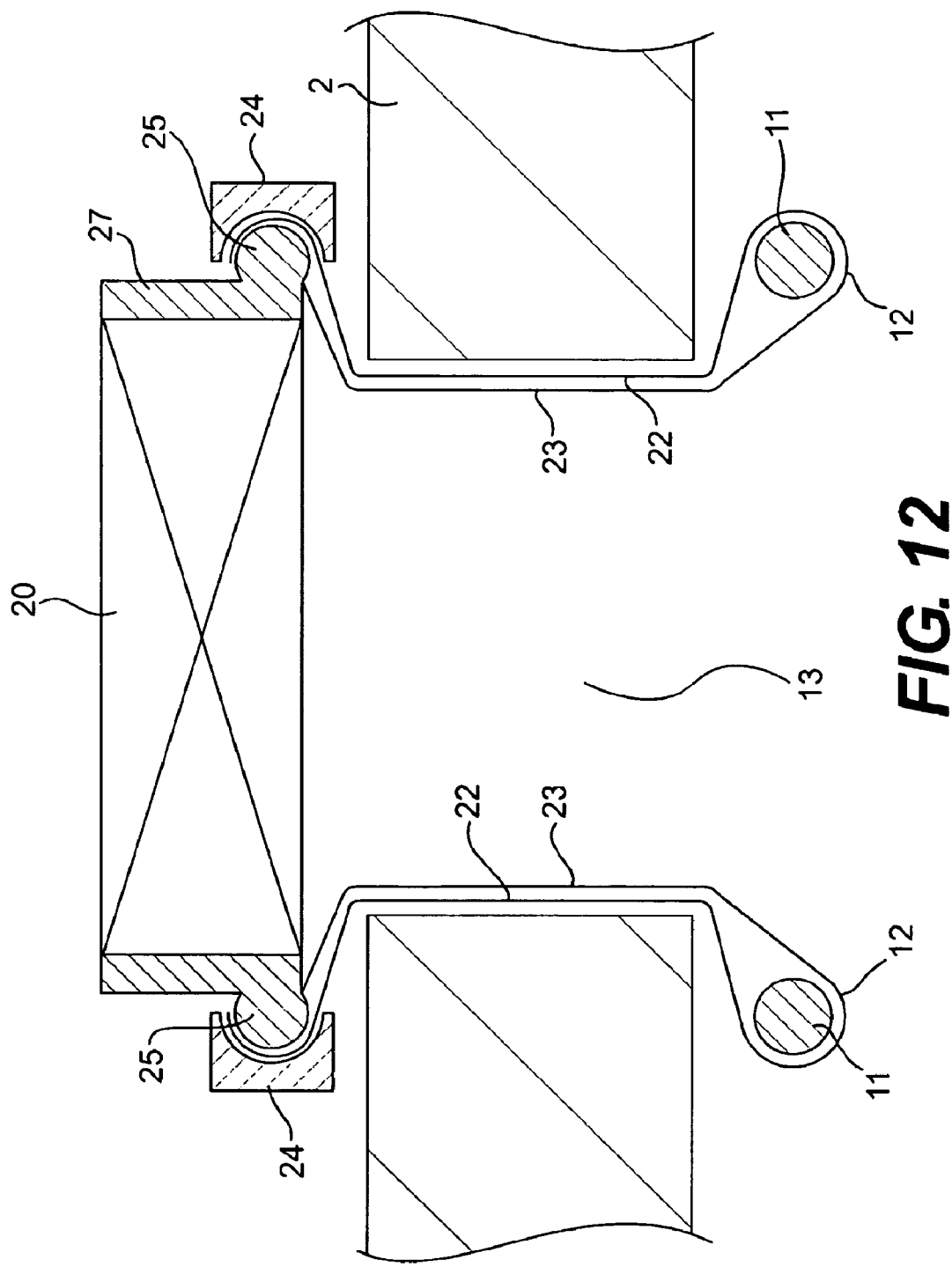
FIG. 12 is a cross sectional, side view of an instrument access device of the invention; in use.

The sleeve 12 may be a single layer sleeve or may have two layers at least in the section which lines the wound opening 13. One such arrangement is illustrated in FIG. 12 in which the sleeve 12 is wrapped around the distal ring 11 and has an outer layer 22 which lines the wound opening 13 and an inner layer 23. A clamp is in this case a proximal clamp comprising an outer proximal ring member 24 and an inner proximal ring member 25 between which the sleeve 12 extends. In this case the inner proximal clamp is mounted to or provided by part of a housing 27 for a valve 20. The sleeve 12 is mounted at one end to the ring member 25 or housing 27 and extends to form the inner layer 23, is wrapped around the distal ring 11 and extends to form the outer layer 22. The sleeve 12 is slidable on at least portion of the inner proximal clamp ring 25 and the sleeve 12 is slidable relative to the distal ring 11. On pulling of the sleeve 12 upwardly the wound opening 13 is retracted. Because of the sleeve pathway a free end of the sleeve 12 is external of the valve 20 and can be readily removed, if desired. In this case the proximal ring member 25 is formed integrally with the housing 27.

Figure 13:
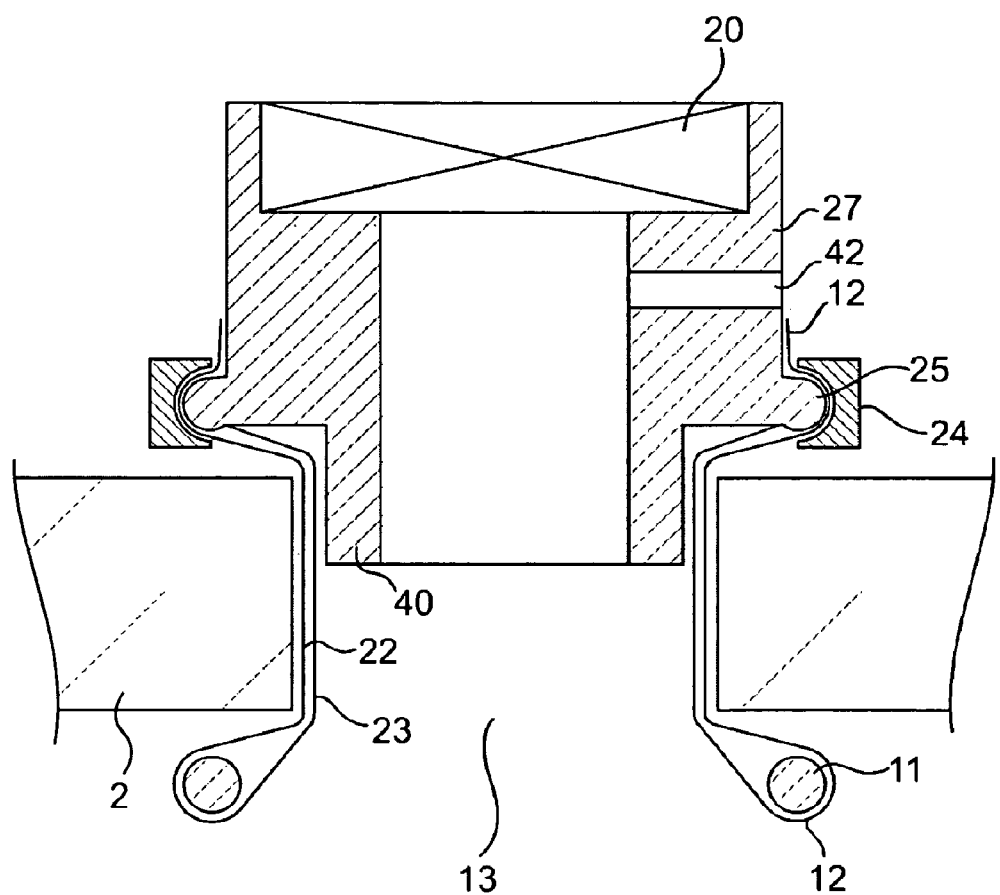
FIG. 13 is a cross sectional, side view of another instrument access device of the invention, in use.
Figure 16:
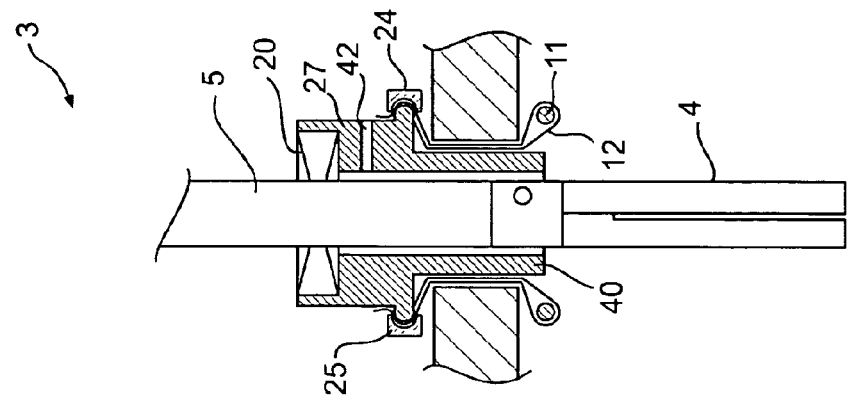
FIGS. 14 to 16 are cross sectional, side views of a further instrument access device of the invention, in use.
Figure 15:
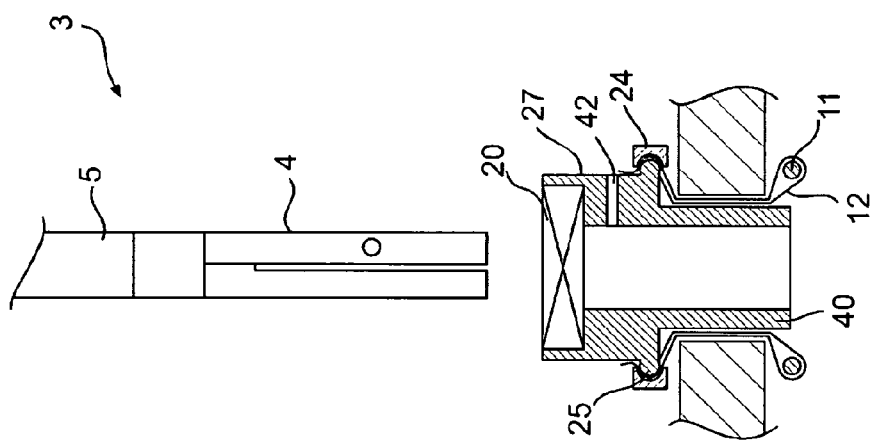
Figure 14:
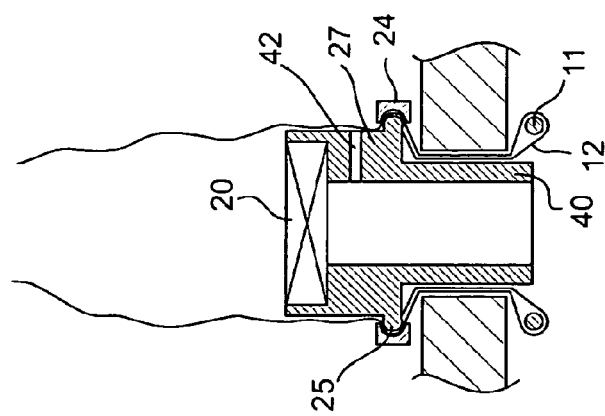
Figure 19:
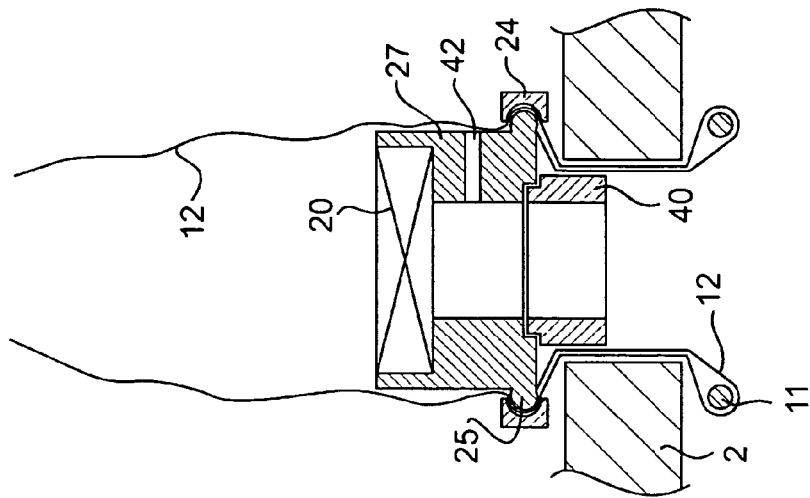
FIGS. 17 to 19 are cross sectional, side views of alternative instrument access devices of the invention, with different tubular members.
Figure 18:
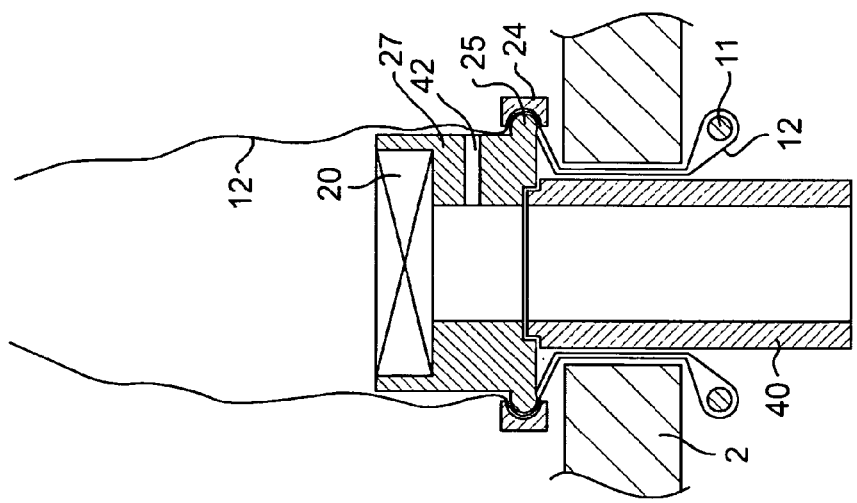
Figure 17:
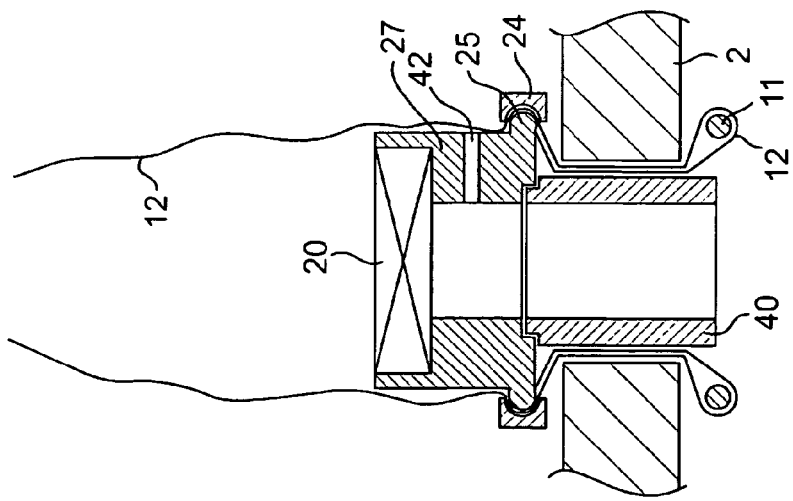
Figure 21:
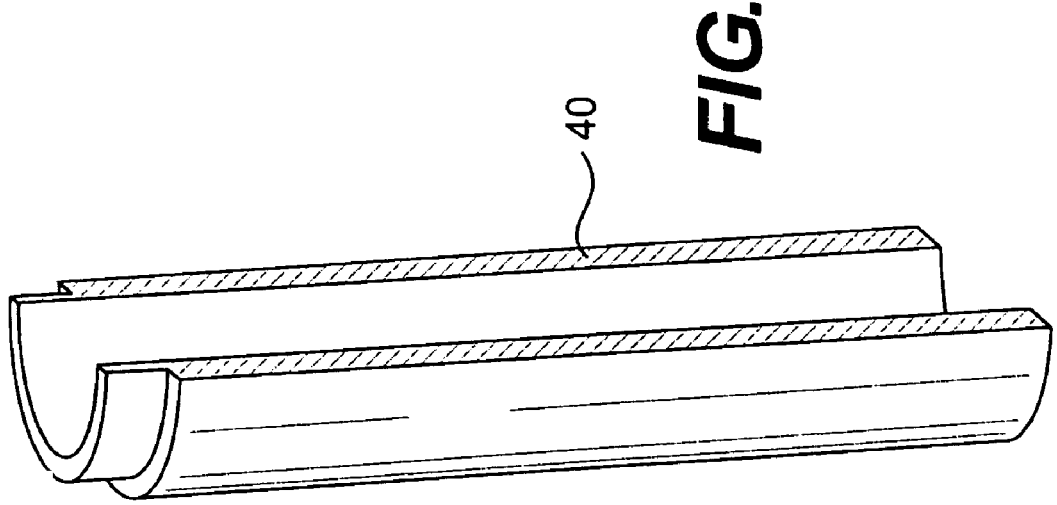
FIG. 21 is a cross sectional, perspective view of the tubular member of FIG. 20.
Figure 22:
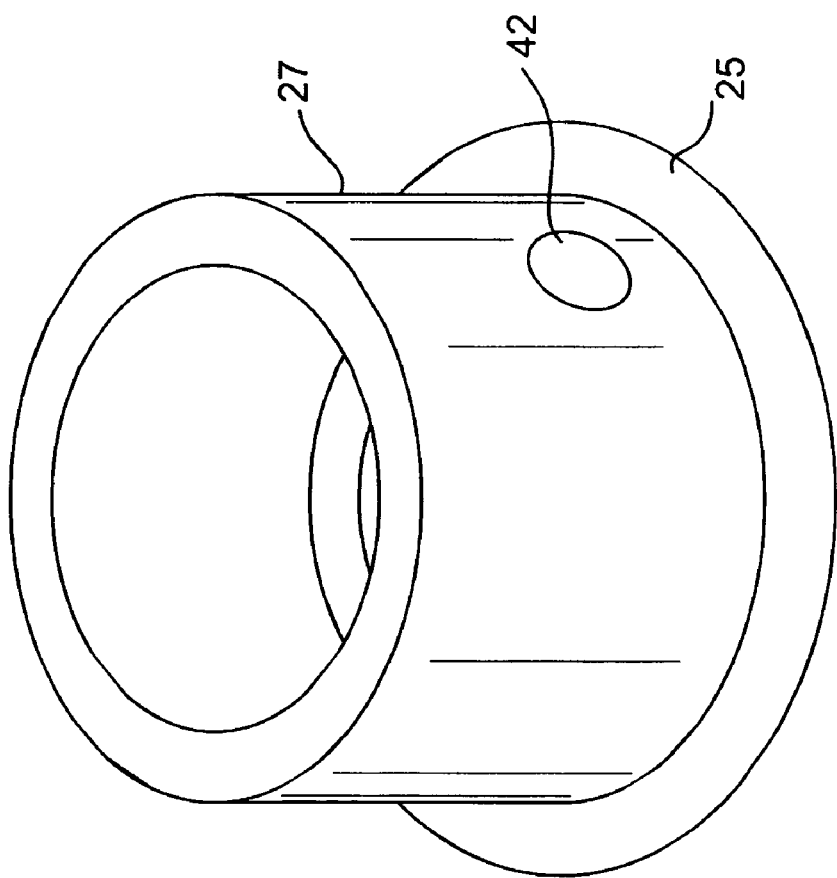
FIG. 22 is a perspective view of a housing part of the access device of the invention.
Figure 23:
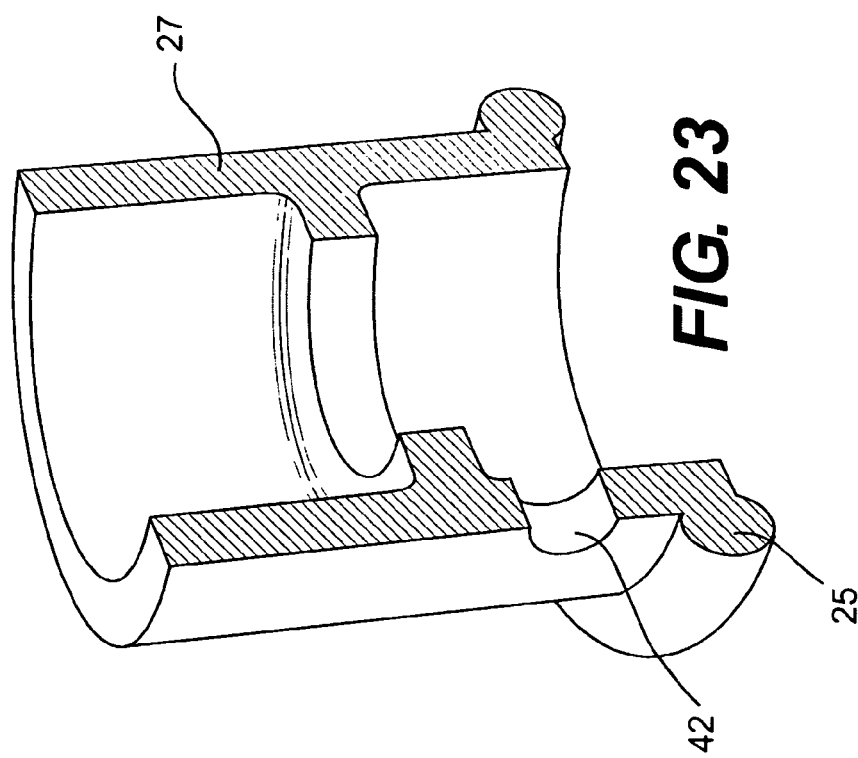
FIG. 23 is a cross sectional, perspective view of the housing part of FIG. 22.

Referring now to FIGS. 13 to 16 there is illustrated an instrument access device having a valve housing 27 and an instrument working channel defined by a tubular member or stub 40 which extends into the wound opening 13 from the valve housing 27. The tubular member 40 need not necessarily extend fully into the wound opening. In the arrangement of FIG. 13 it is shown extending only partially through the wound opening whilst in FIGS. 14 to 16 the tubular member 40 extends fully the thickness of the abdomen. The valve housing 27 in this case also has an insufflation port 42. In this case the tubular member 40 is formed integrally with the housing 27.

The tubular member 40 may be detachably mounted to the valve housing 27 as illustrated particularly in FIGS. 17 to 25. In this way the access device may be adapted for different situations such as different sized abdomens or depending on the degree of access required by the surgeon. The tubular members 40 may be of varying lengths, as illustrated. Any suitable mounting may be provided between the tubular member 40 and the valve housing 27 such as adhesive, an interference fit, a spigot and socket, screw threaded, or bayonet type fitting.

Figure 24:
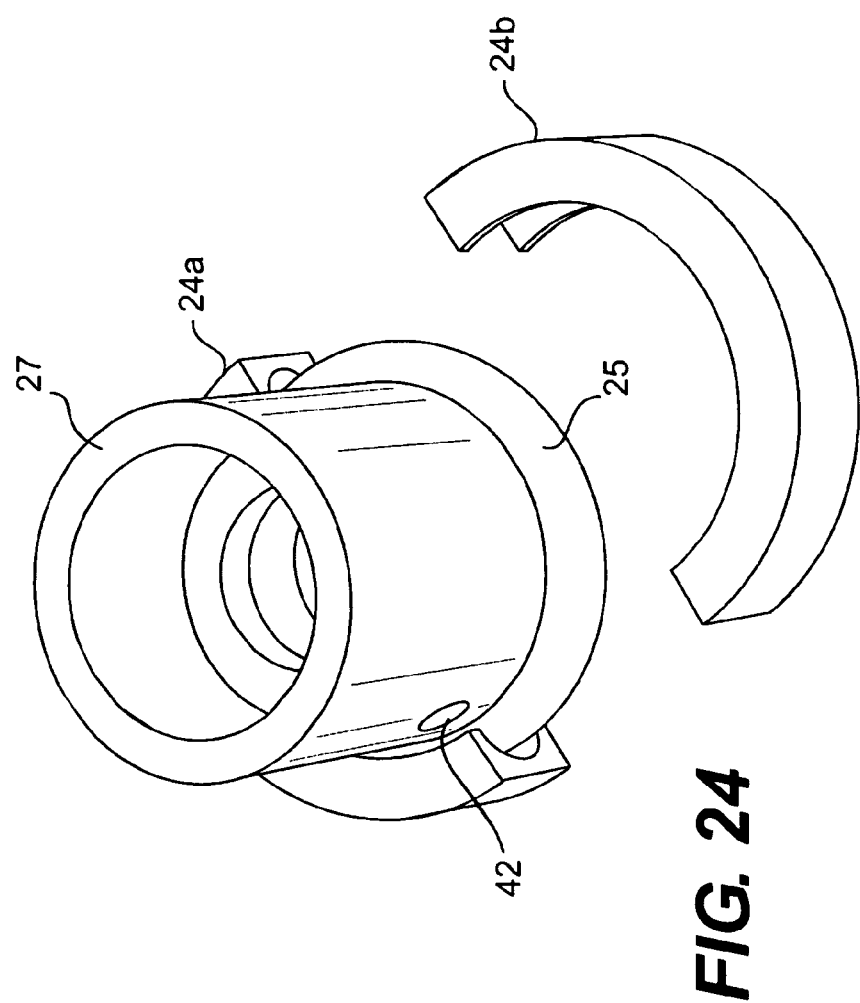

Referring to FIGS. 24 and 25 the outer proximal clamp ring member may be split into sections 24a, 24b for ease of assembly, disassembly. The ring sections 24a, 24b can be assembled and fixed using any suitable means such as adhesive or the like.

Referring to FIGS. 26 to 28 there is illustrated a further instrument access device according to the invention. In this case a seal in the form of a sheet 50 of film material is extended across the inner proximal ring 25 to maintain pneumoperitoneum. The tubular member 40 has a tapered distal end 55 for ease of breaking through the film 50 as illustrated in FIG. 27. The valve housing 27 in this case is configured at 56 to snap fit over an outer proximal ring 24 for assembly of the valve housing 27 to the retractor base. The access device is illustrated in use in FIG. 28.

Referring to FIGS. 29 and 30 the access device in this case has a gripper or handle provided by an anchor eye 57 and a lifting wire 58. On pulling of the lifting wire 58 upwardly as indicated by the arrow in FIG. 30 the device can be easily tilted providing easier access to more areas of the abdomen. The force on the lifting wire 58 can be varied to increase or decrease the angle alpha to provide further desired access.

Figure 31:
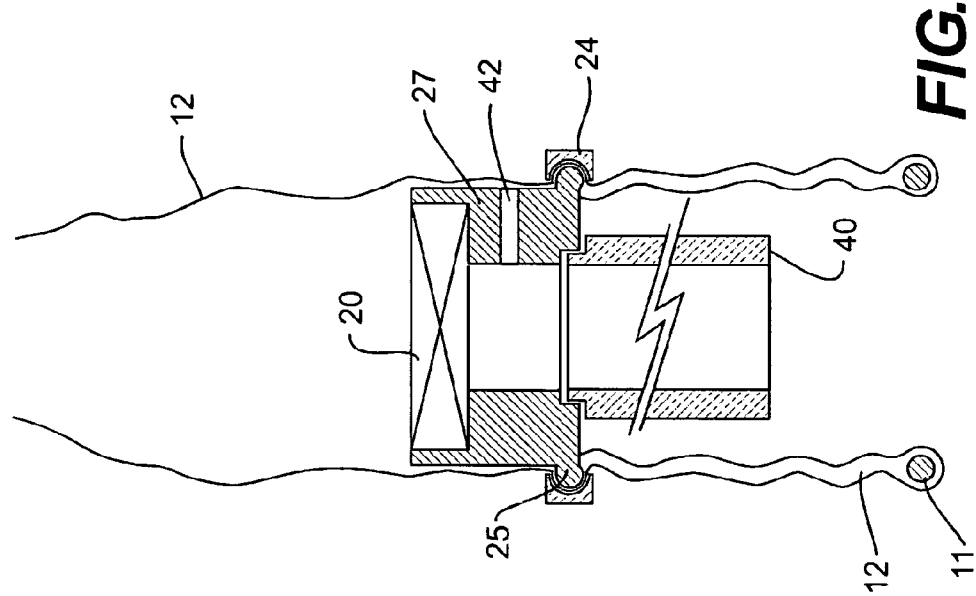
FIGS. 31 and 32 are cross sectional, side views of another instrument access device of the invention.
Figure 32:
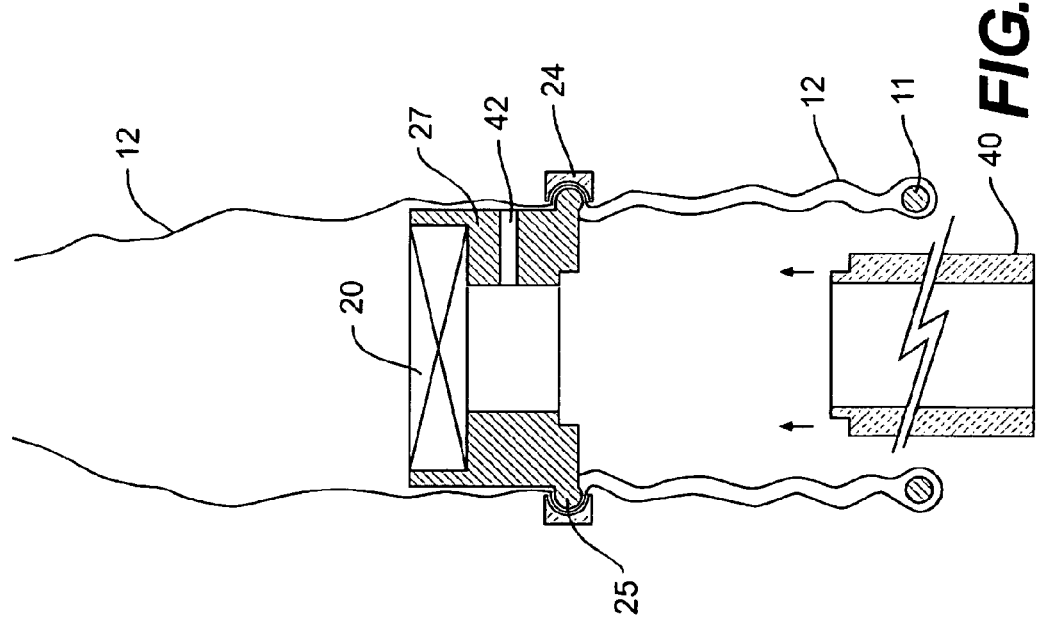
Figure 34:
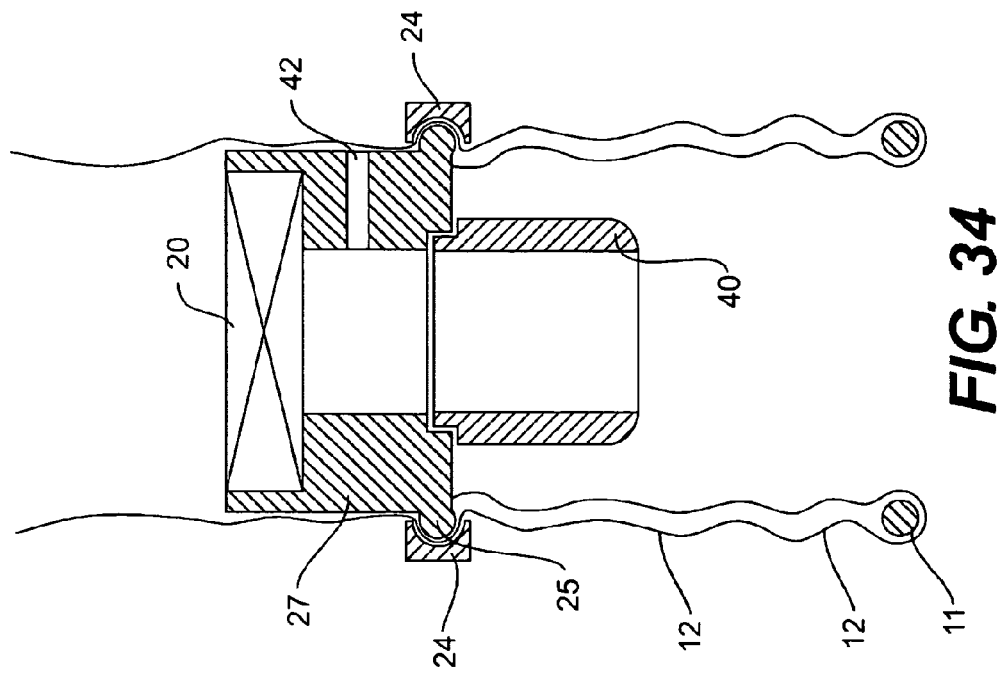
Figure 33:
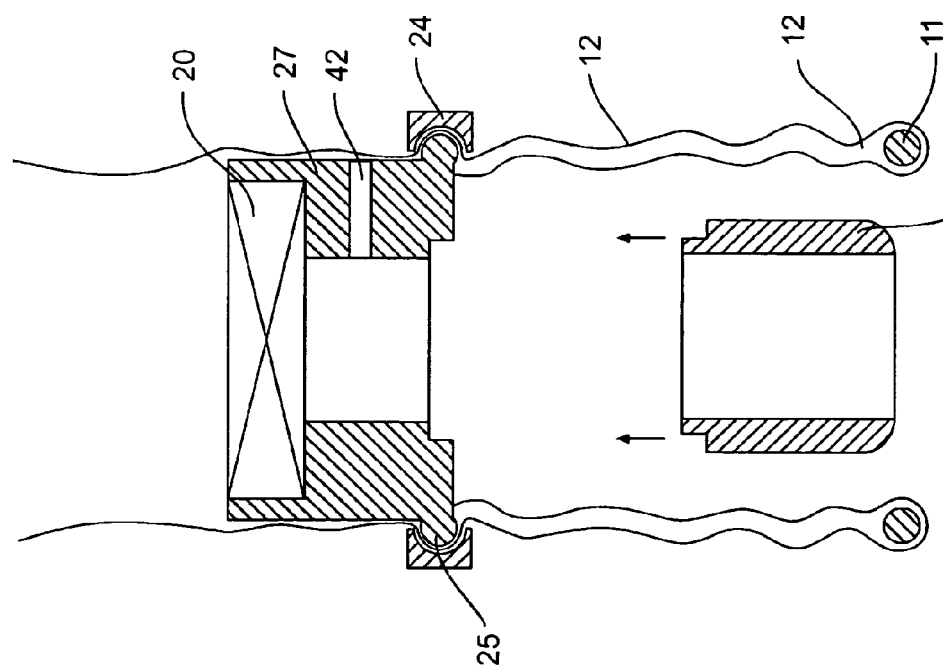

Referring to FIGS. 31 and 32 there is illustrated another instrument access device which is similar to those described above and like parts are assigned the same reference numerals. In this case the tubular member 40 is detachable and a suitable tubular member 40 is attached to the valve housing 27 prior to deployment in a patient.

Referring to FIGS. 33 to 37 there is illustrated the method of using a device such as the device of FIGS. 31 and 32. The surgeon first selects the detachable tubular member 40 of desired length, for example based on the abdominal wall thickness. The tubular member 40 is attached (FIG. 34) so that the device is ready for deployment. The distal ring 11 is deployed in the abdomen as described above. The sleeve 12 is pulled upwardly in the direction of the arrow A whilst pushing down on the proximal ring 24 in the direction of the arrow B. Retraction of the incision 1 commences and the tubular member 40 begins to enter the margin of the incision 1 (FIG. 36). As the pulling and pushing action is continued the tubular member 40 is fully deployed creating an instrument working channel in the wound opening 13 (FIG. 37). The device is extremely low profile, easy to deploy, and creates an excellent working channel which provides maximum flexibility in instrument manipulation.

Figure 39:
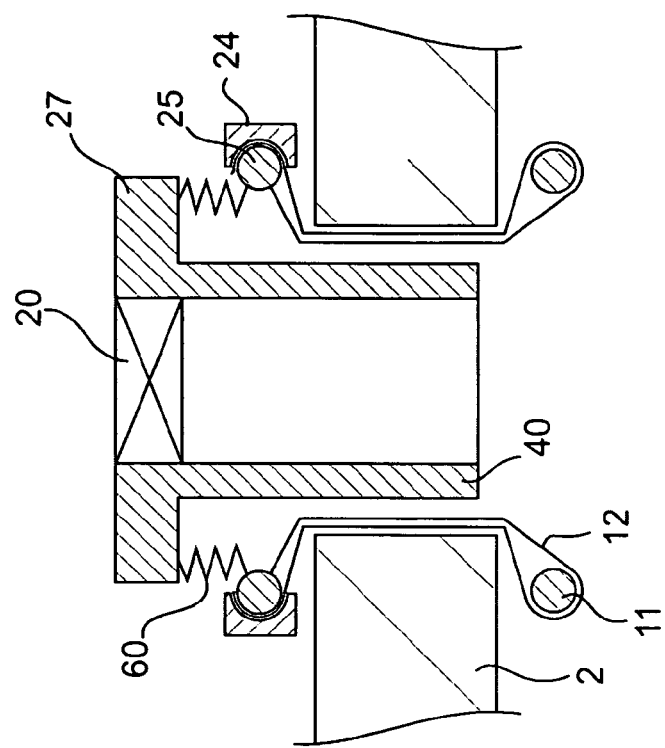
FIGS. 38 and 39 are cross sectional, side views of a still further instrument access device of the invention.
Figure 38:
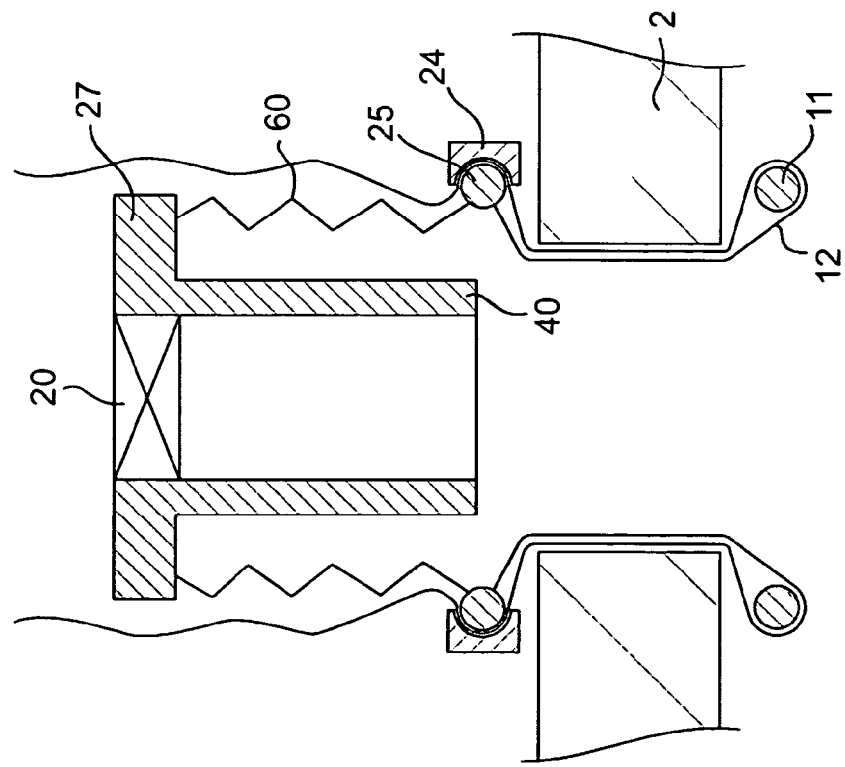

Referring to FIGS. 38 and 39 there is illustrated another instrument access device which is similar to those described above and like parts are assigned the same reference numerals. In this case the valve housing 27 is connected to the inner proximal ring 25 by a suitable connection such as a flexible sleeve or corrugated tube 60. In use, the tubular member 40 is flexible relative to the proximal anchor which may be beneficial in reducing drag/friction.

Figure 40:
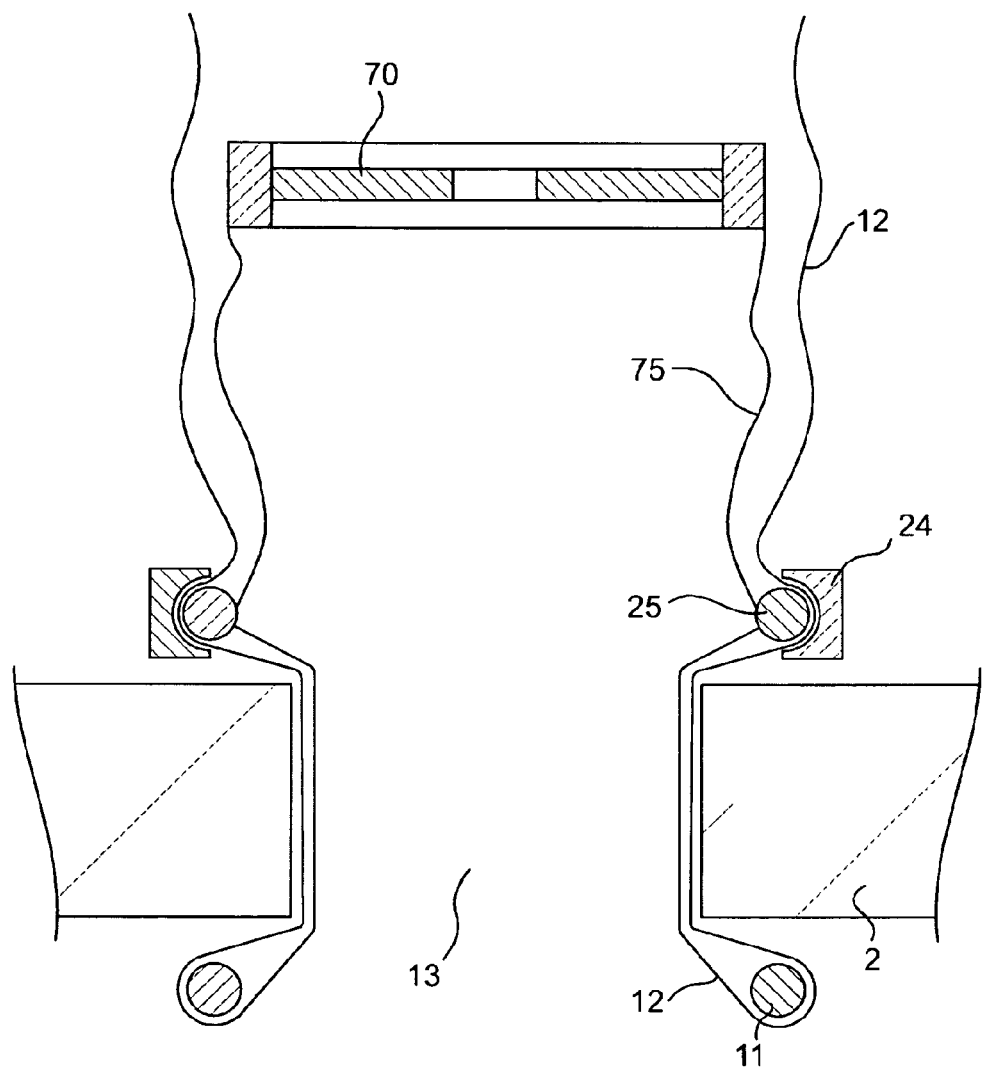

Another access device of the invention is illustrated in FIG. 40. In this case, the free end of the sleeve 12 is external of a valve such as a lipseal valve 70 which is connected to the inner proximal ring 25 by means of a flexible connecting sleeve 75.

Figure 43:
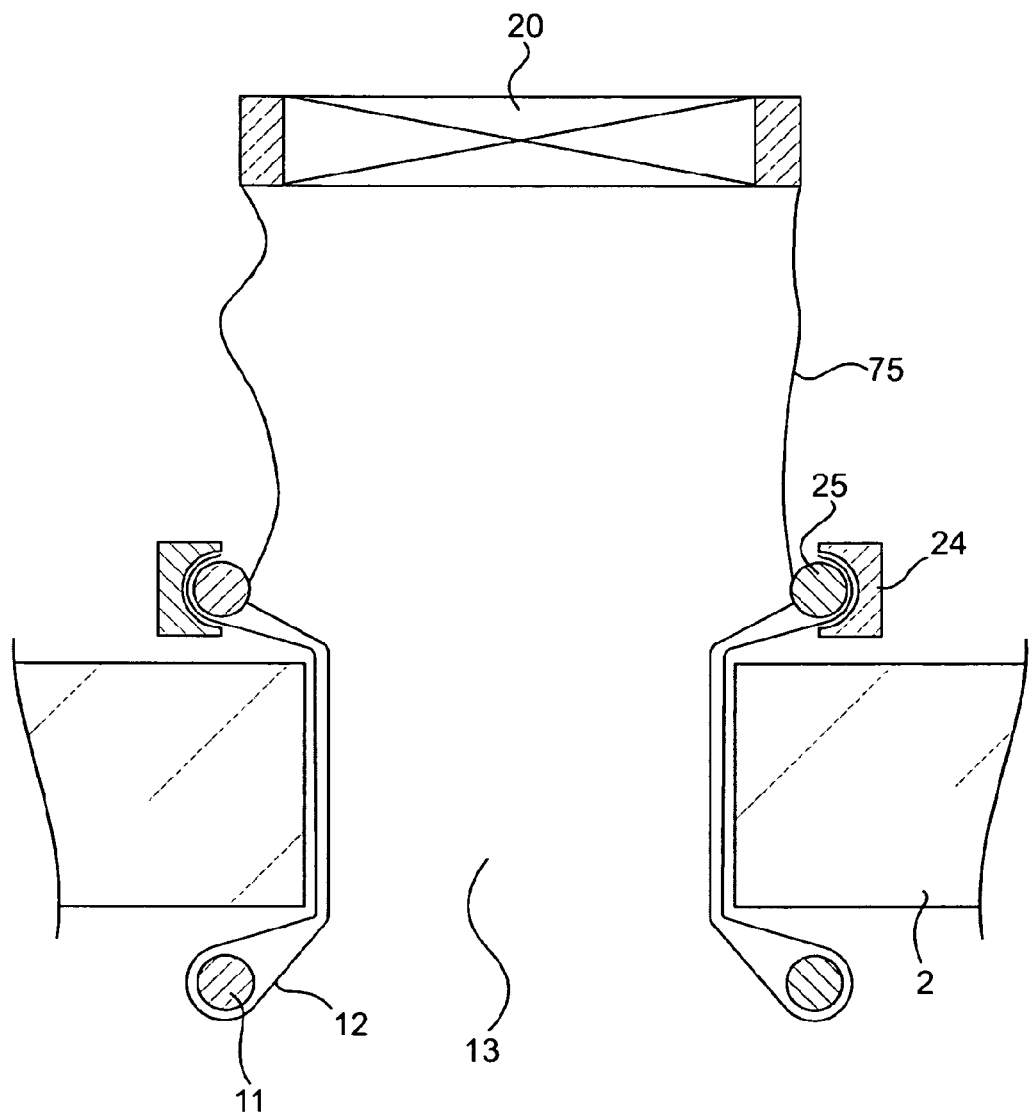
FIG. 43 is a cross sectional, side view of a further instrument access device of the invention.

The retractor is easily deployed as the free end of the sleeve 12 which is pulled on for deployment is readily accessible. The operation of this device is illustrated in FIGS. 41 and 42. It will be noted that in view of the flexible connection 75 tilting of the instrument does not cause a leak path. This arrangement may be used with any suitable valve(s) and/or seal(s) 20, as illustrated in FIG. 43.

Figure 44:
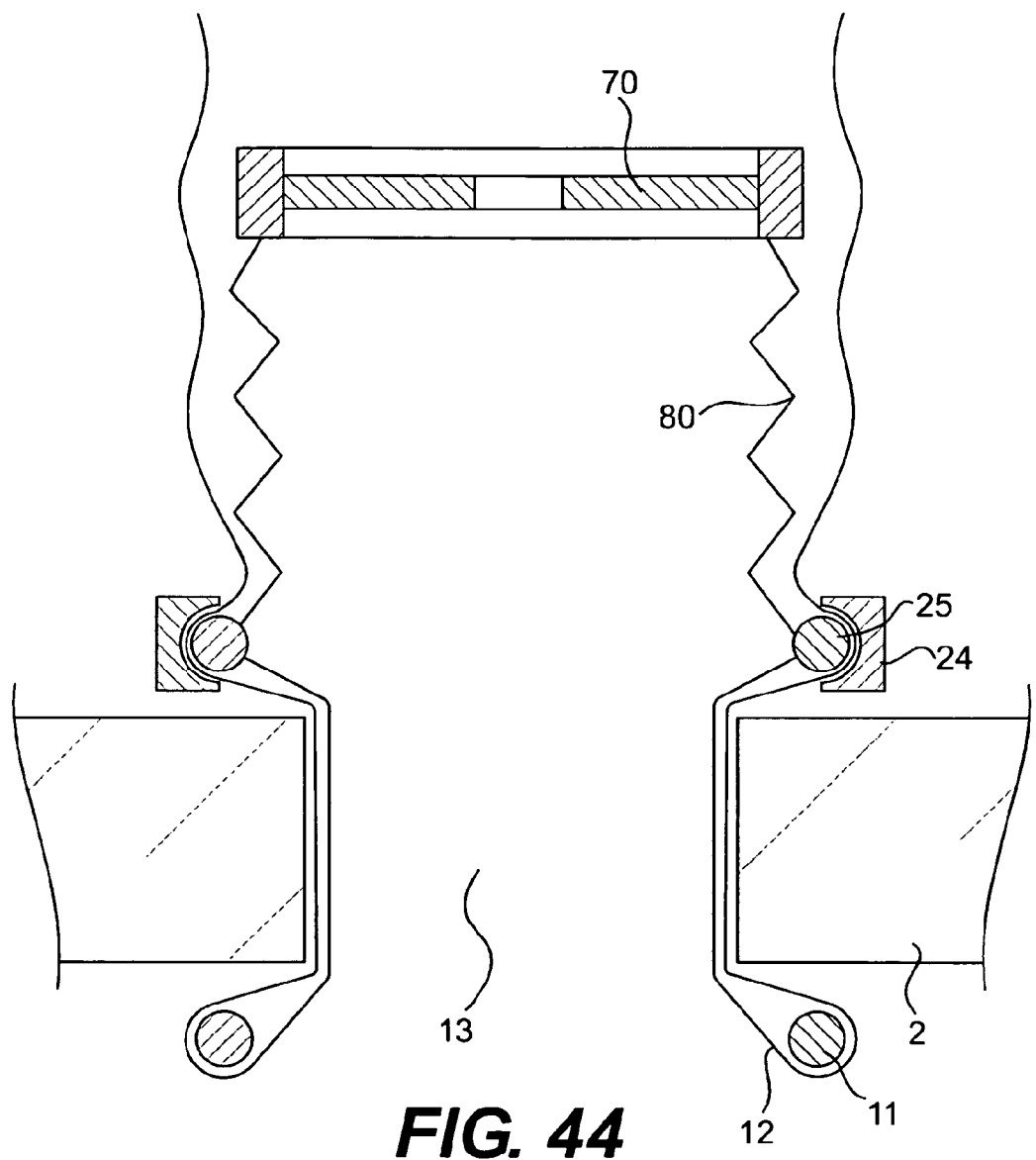
FIGS. 44 to 46 are cross sectional, side views of another instrument access device of the invention.
Figure 45:
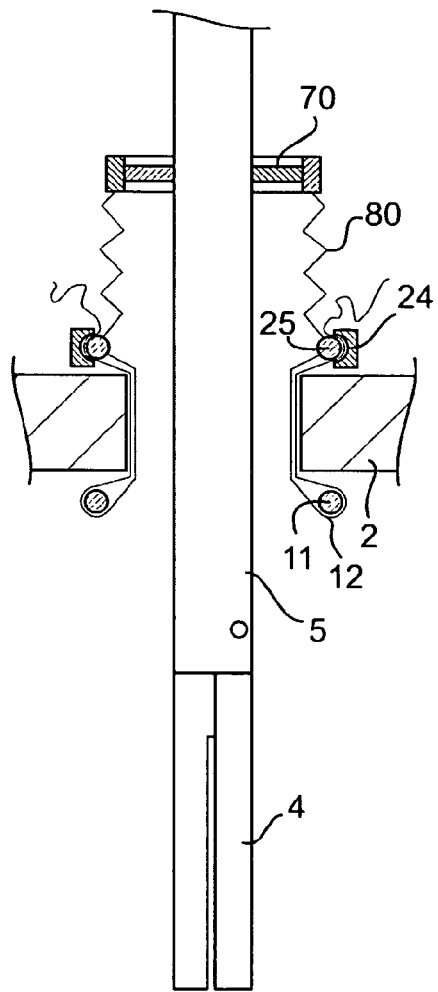
Figure 46:
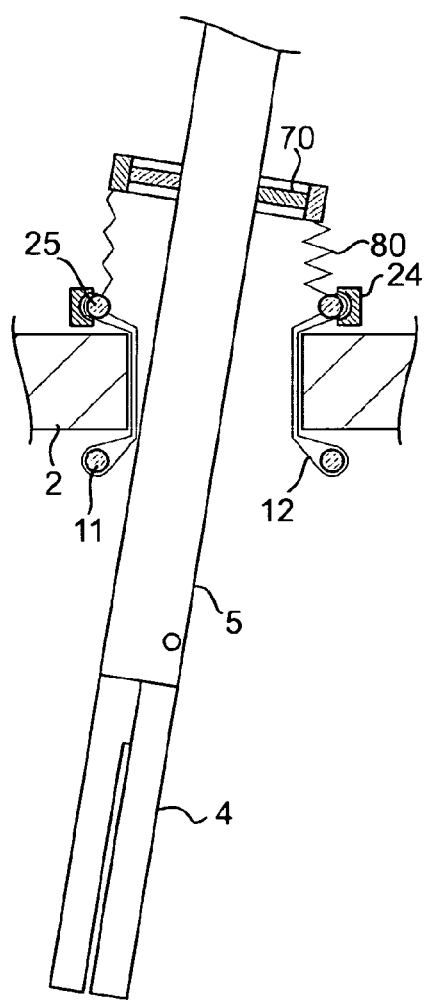

Another access device similar to that of FIGS. 40 to 42 is illustrated in FIGS. 44 to 46. In this case the flexible connection is provided by a corrugated tube 80.

Figure 48:
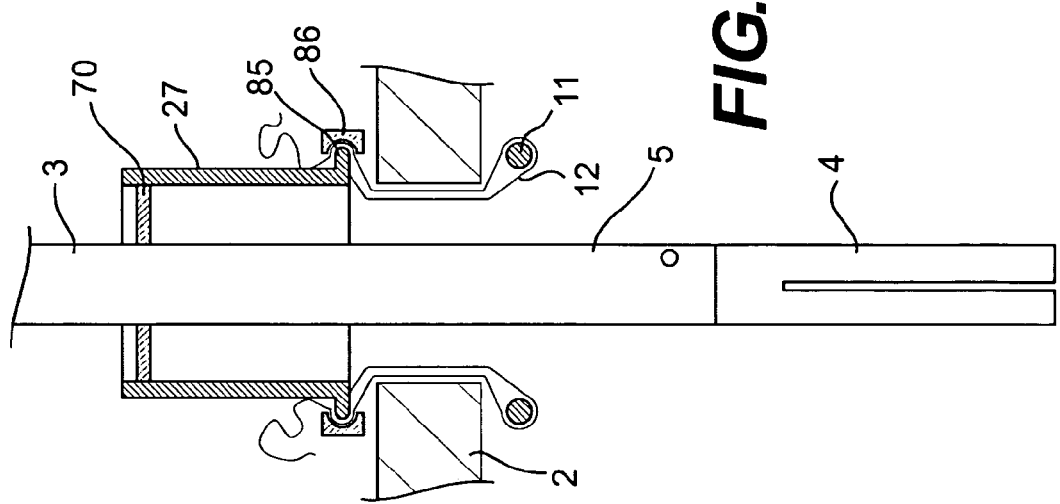
FIGS. 47 to 49 are cross sectional, side views of a further instrument access device of the invention.
Figure 47:
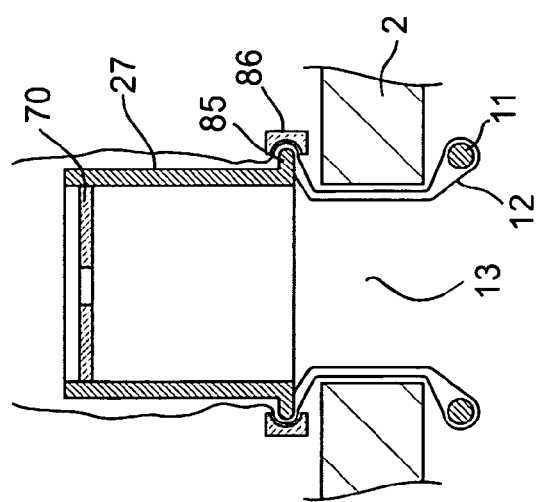
Figure 49:
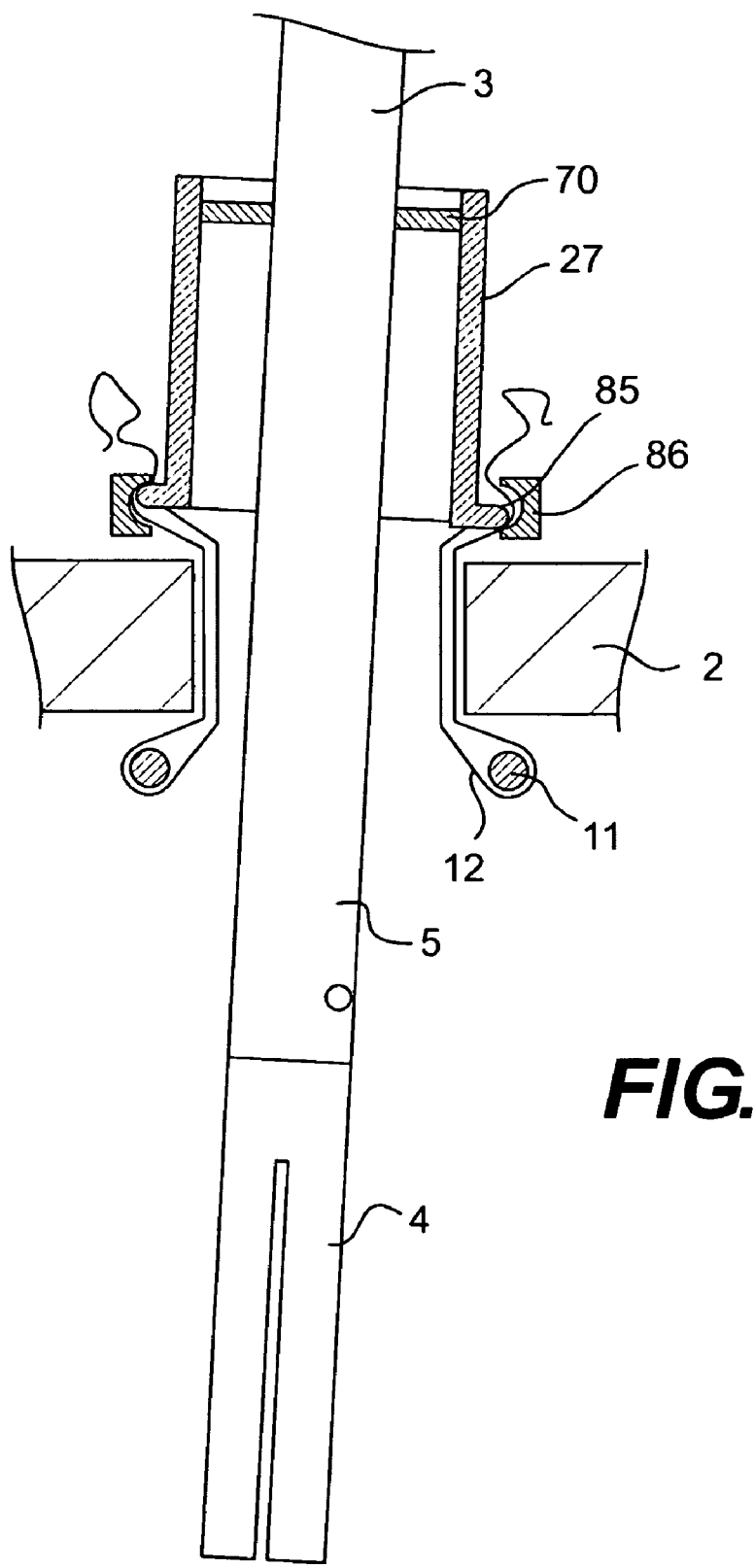
Figure 52:
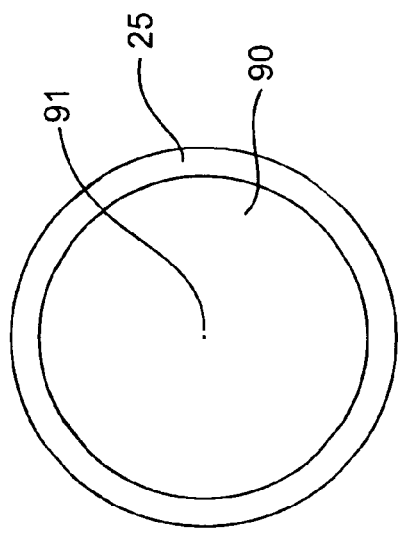
FIGS. 50 to 55 are views of another instrument access device of the invention.
Figure 51:
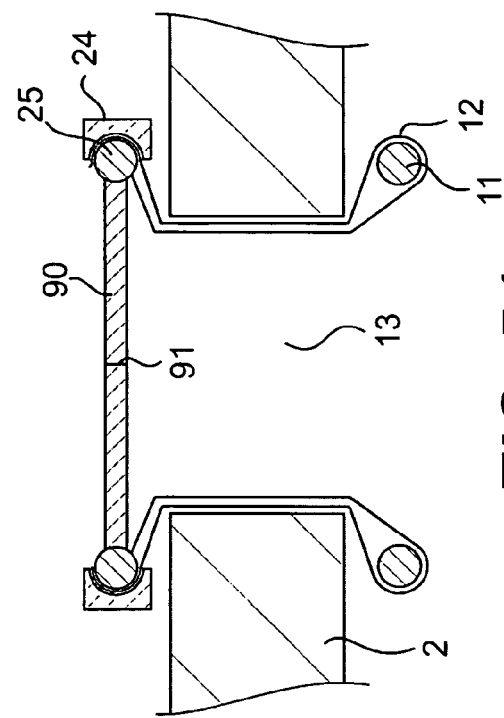
Figure 50:
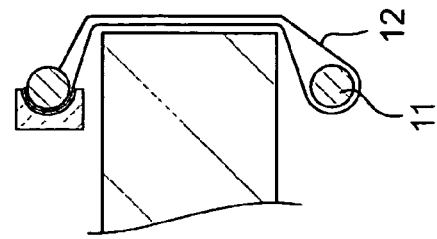
Figure 55:
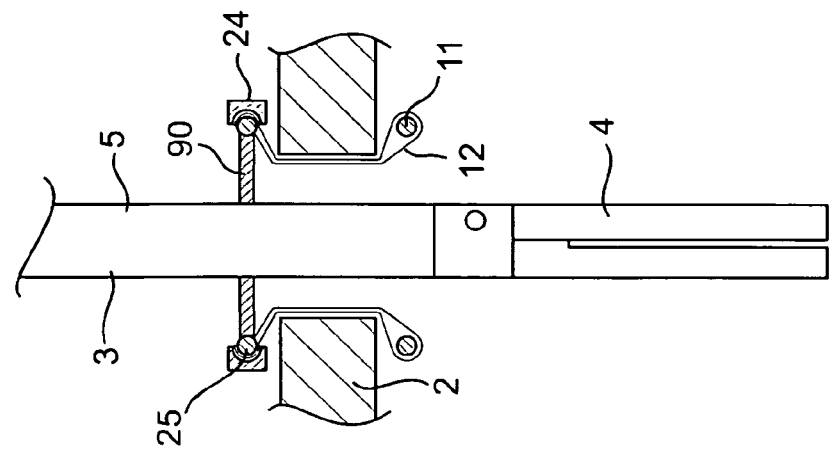
Figure 54:
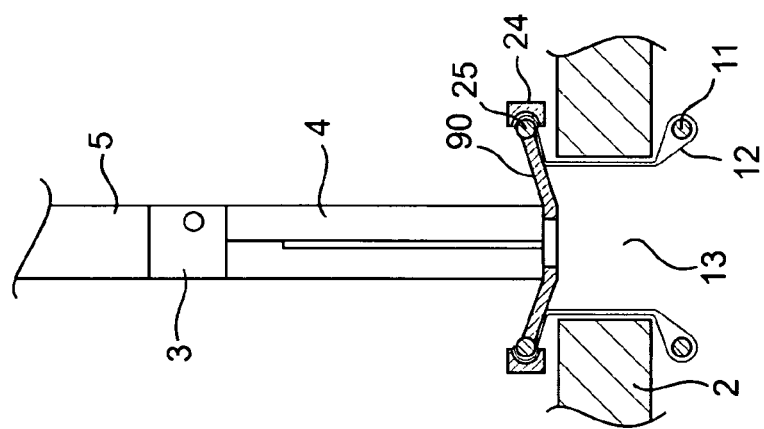
Figure 53:
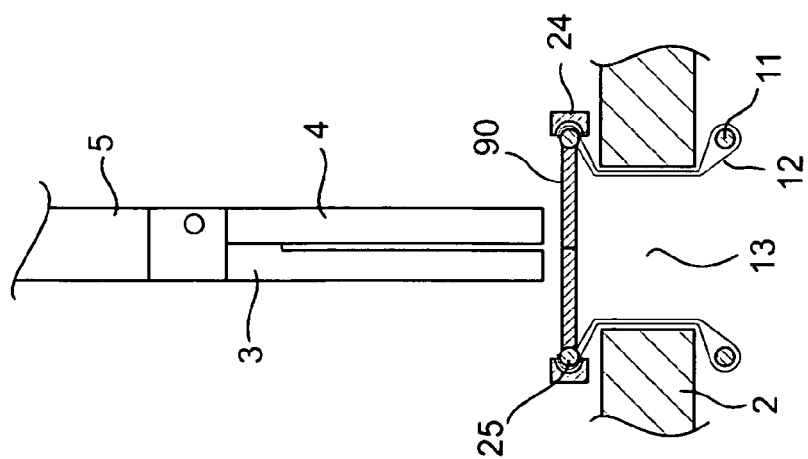

A further access device of the invention is illustrated in FIGS. 47 to 49. It will be noted that in this case a proximal inner ring 85 is undersized with respect to the receiver of an outer proximal ring 86. As illustrated in FIG. 49 when the instrument 3 is tilted off its vertical axis, the valve housing 27 can move due to this clearance without compromising the seal between the lipseal 70 and the instrument 3. Thus, off-axis movement is accommodated without compromising the seal to the instrument 3.

Referring to FIGS. 50 to 55 a self locking retractor of the type described above has a valve/seal provided by a body of gelatinous elastomeric material 90 which in this case is simply illustrated as extending across the inner proximal ring 25. The gelatinous elastomeric body 90 may have a pin hole 91 for ease of insertion of an instrument 3. The gel 90 deforms as the instrument 3 is inserted. If there is a pre-made pinhole 91, this facilitates entry. If there is no pinhole, the leading edge of the instrument 3 will eventually pierce the material. In use the gel 90 seals around the instrument shaft 5. Upon withdrawal of the instrument 3, the hole 91 in the gel 90 self-seals closed.

Figure 56:
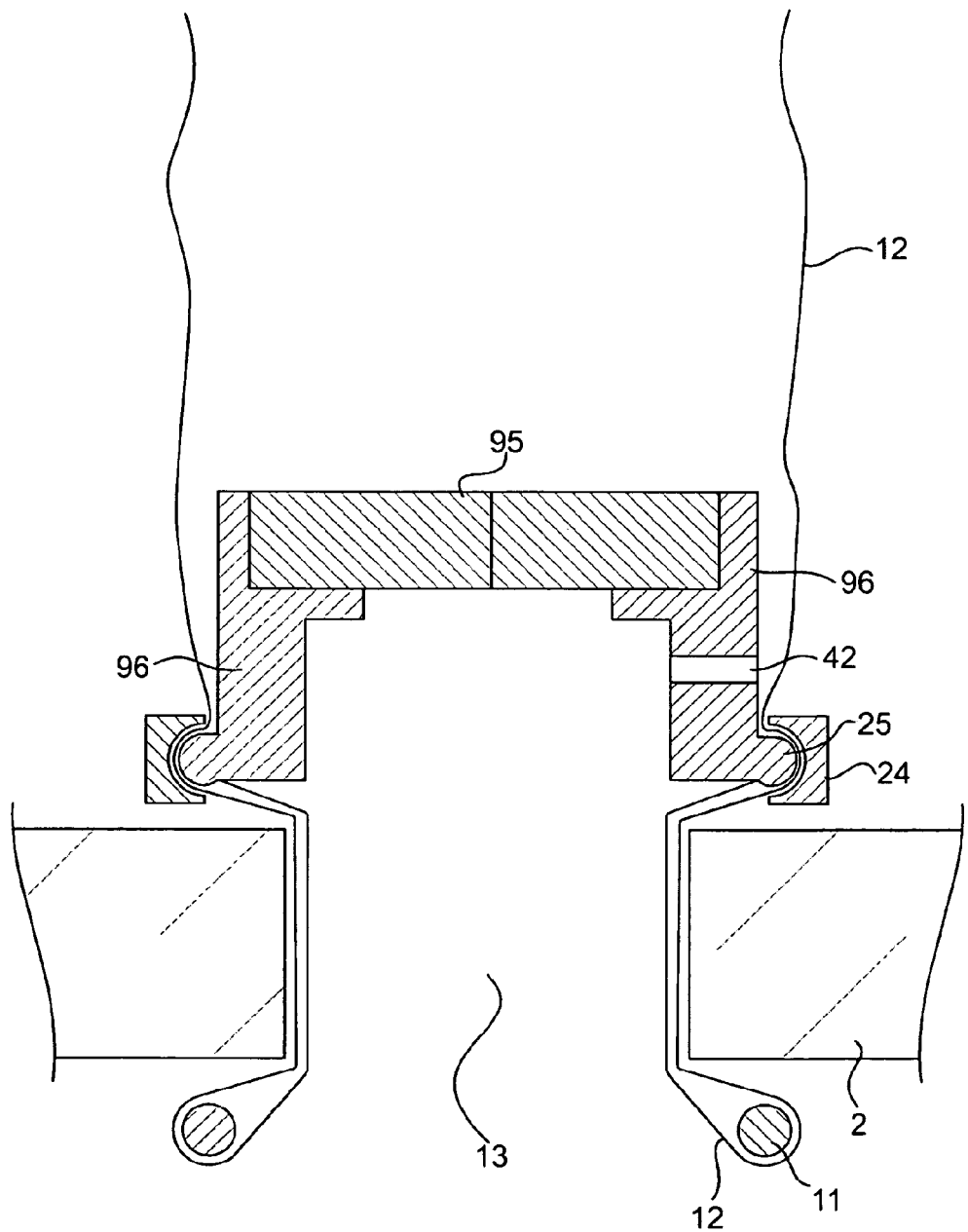
Figure 58A:
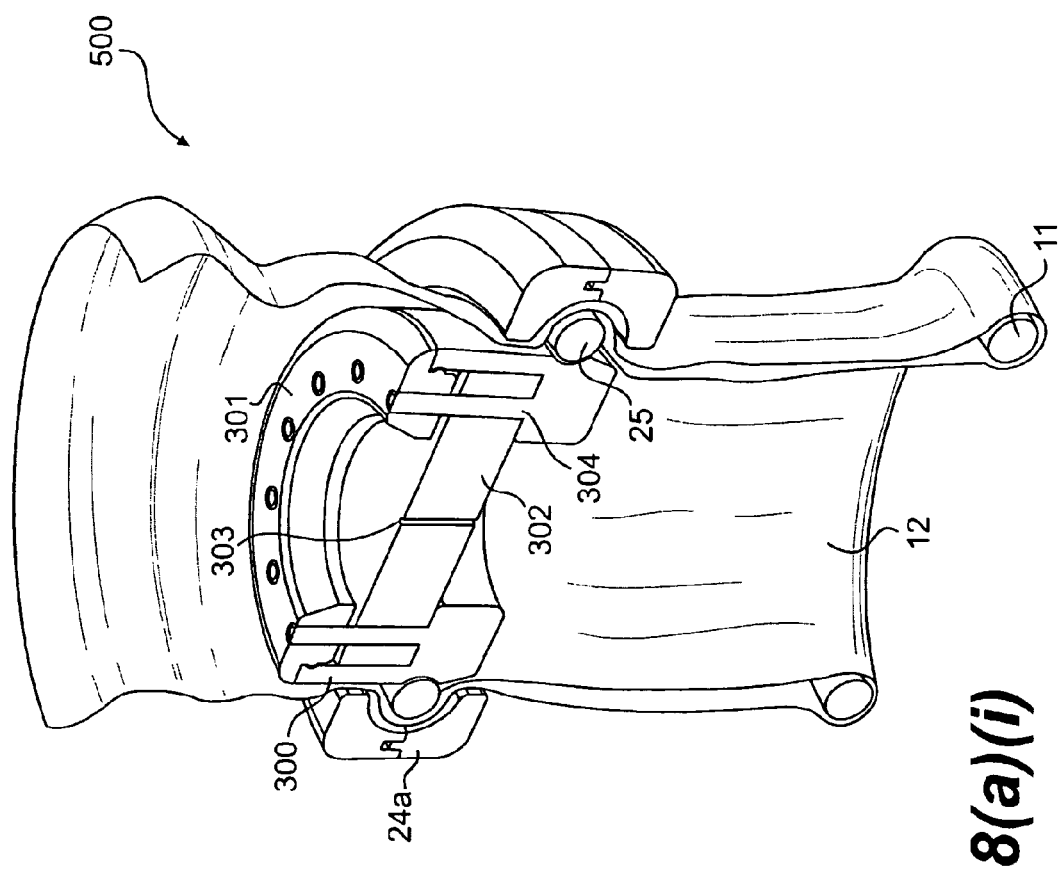
FIG. 58(a)(i) is a cut-away, perspective view of another instrument access device according to the invention.
Figure 58B:
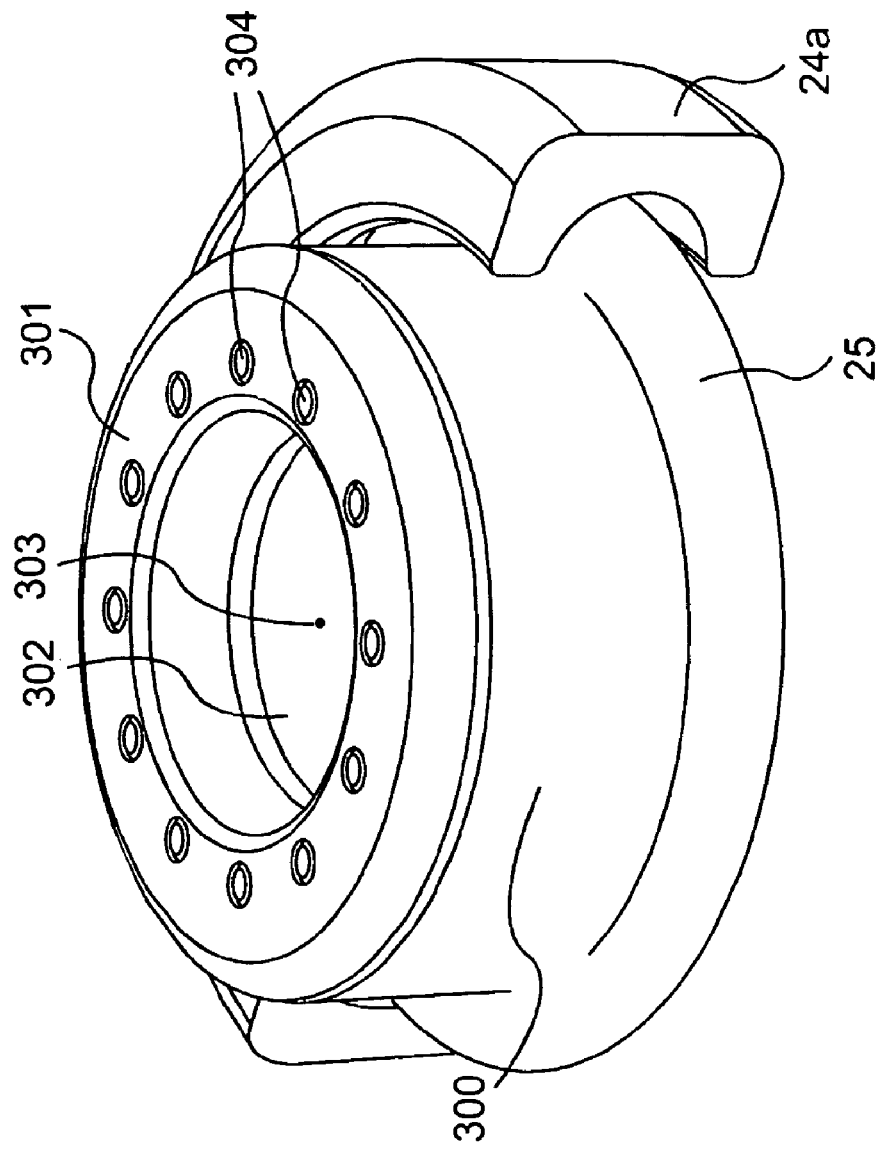
FIG. 58(b) is an assembled, perspective view of the part of the instrument access device of FIG. 58(a)(ii)
Figure 58C:
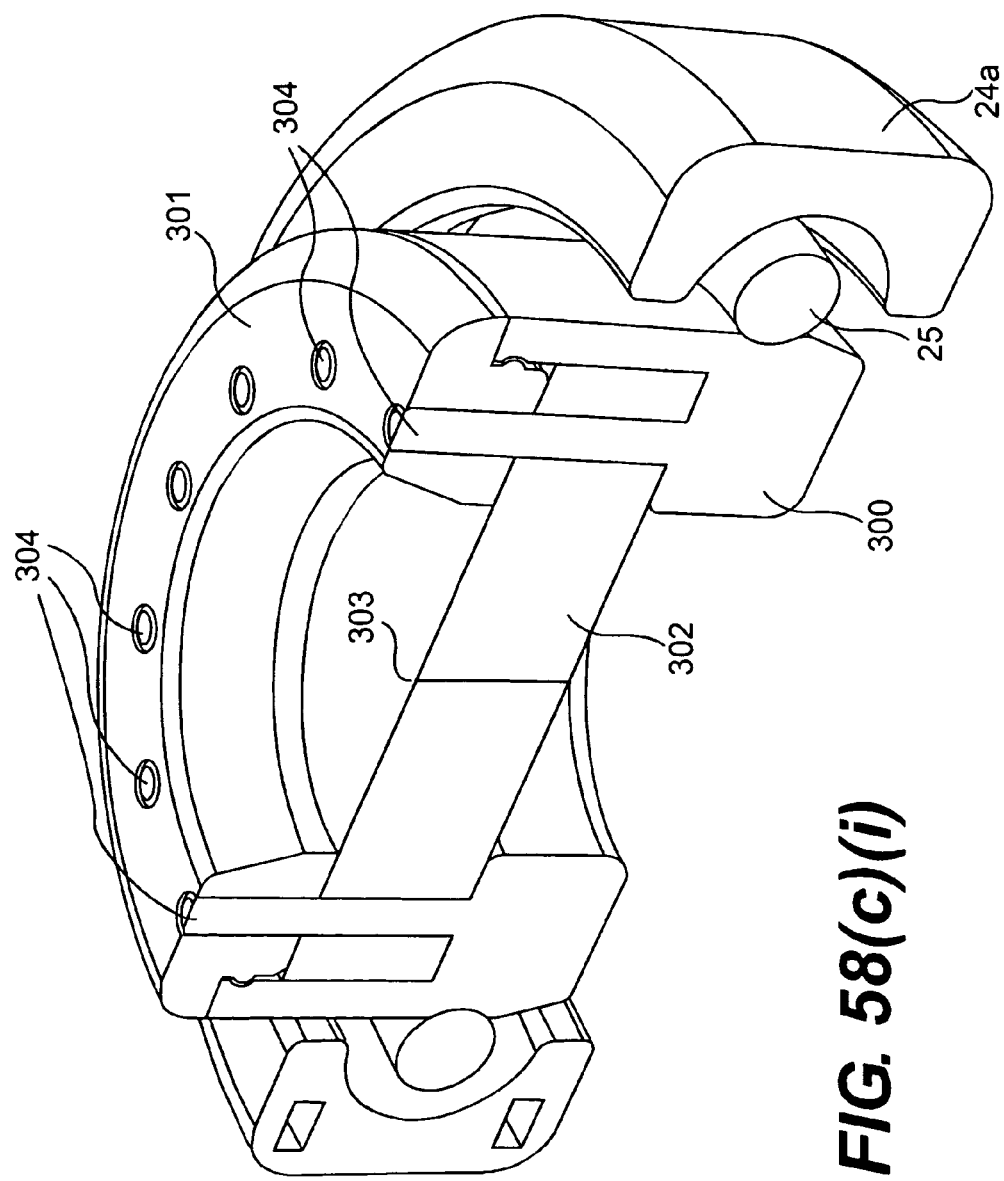
FIG. 58(c)(i) is a cut-away, perspective view of the part of the instrument access device of FIG. 58 (a)(ii)
Figure 58D:
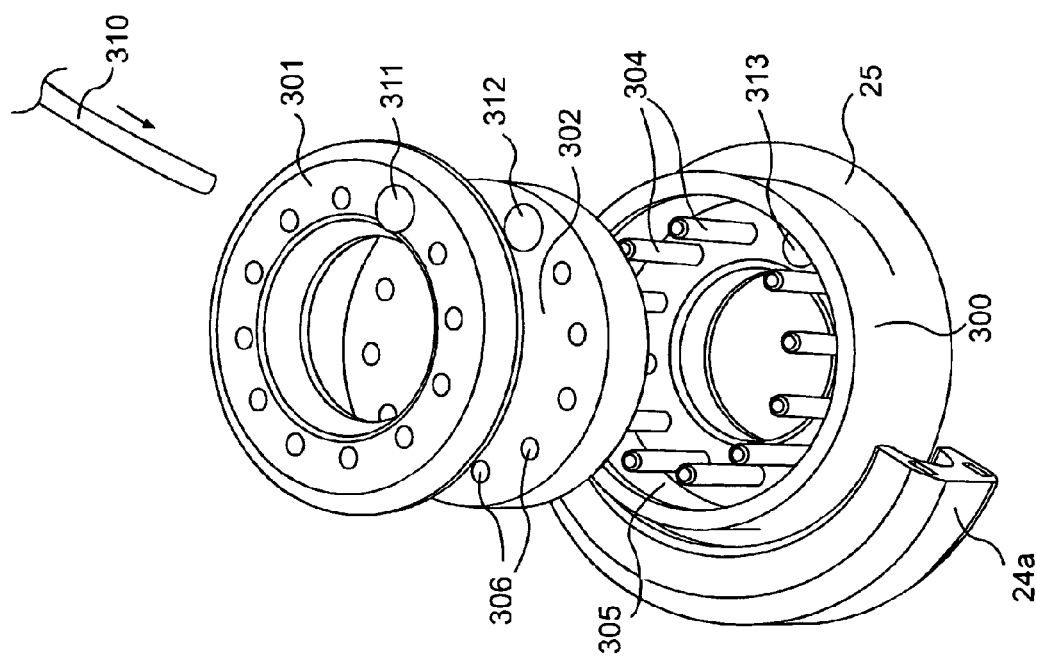
FIGS. 58(d) and 58(e) are views similar to FIGS. 58(a)(ii) and 58(c)(i) of part of another instrument access device according to the invention.
Figure 58E:
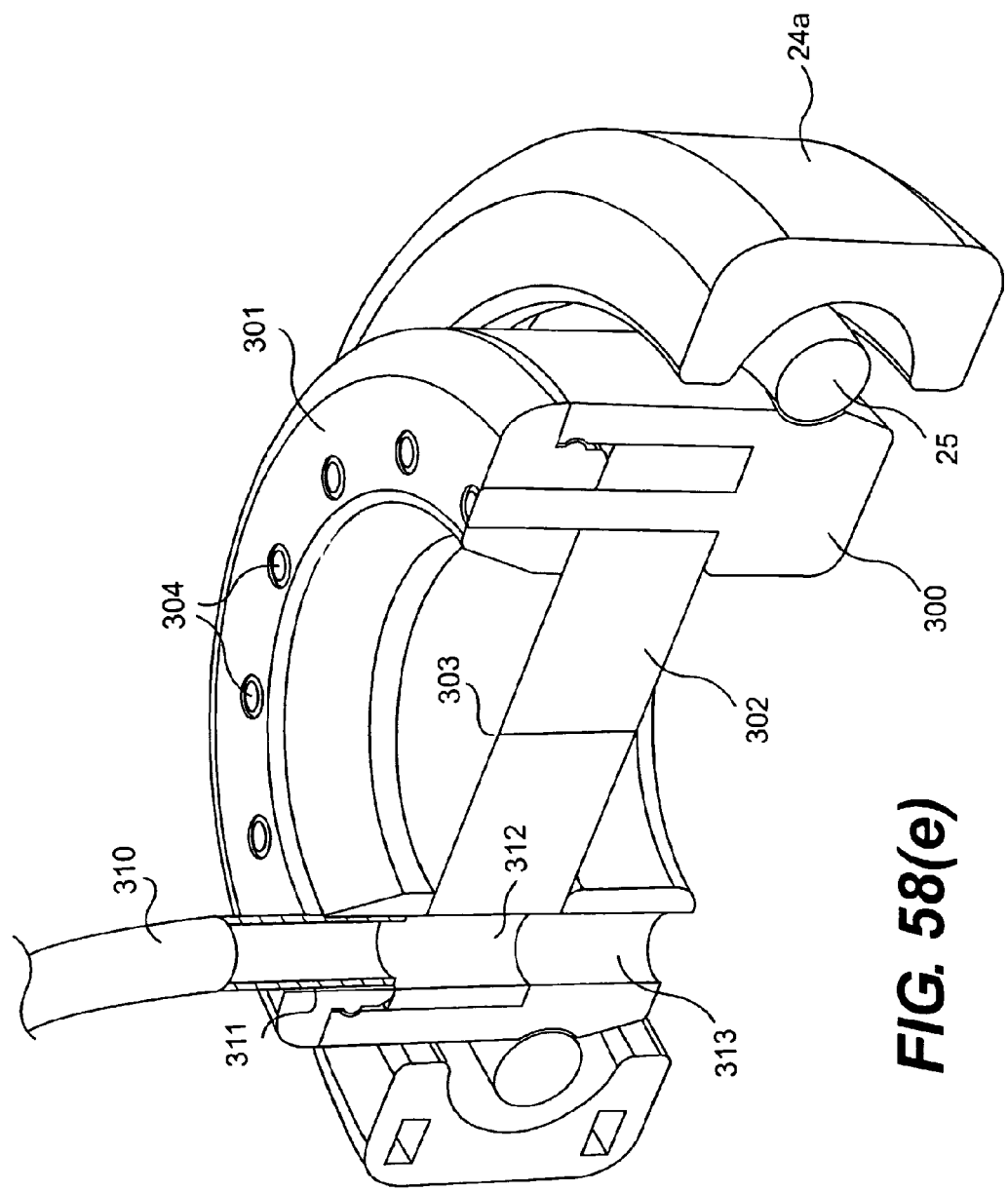
Figure 58G:
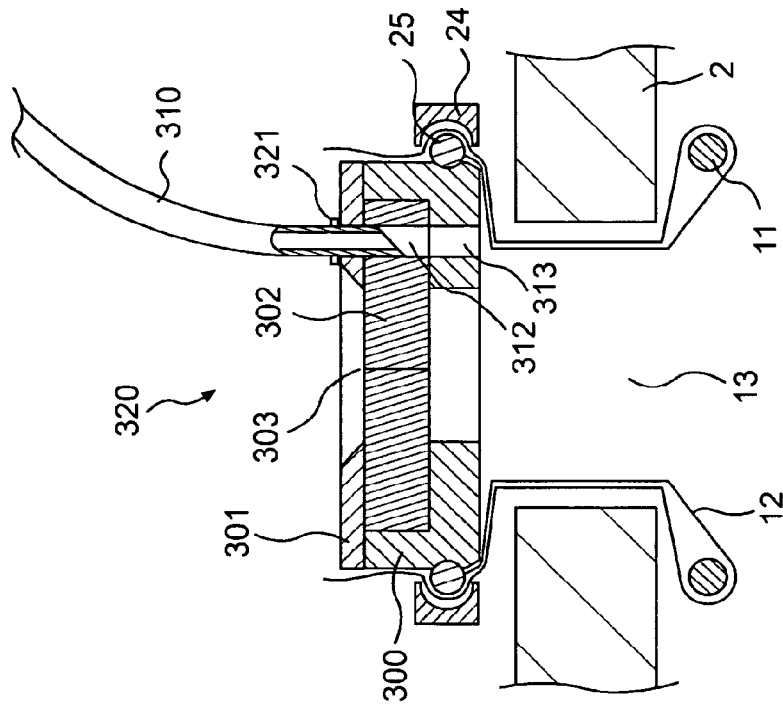
FIGS. 58(f) and 58(g) are partially cross-sectional, side views of another instrument access device according to the invention, in use.
Figure 58F:
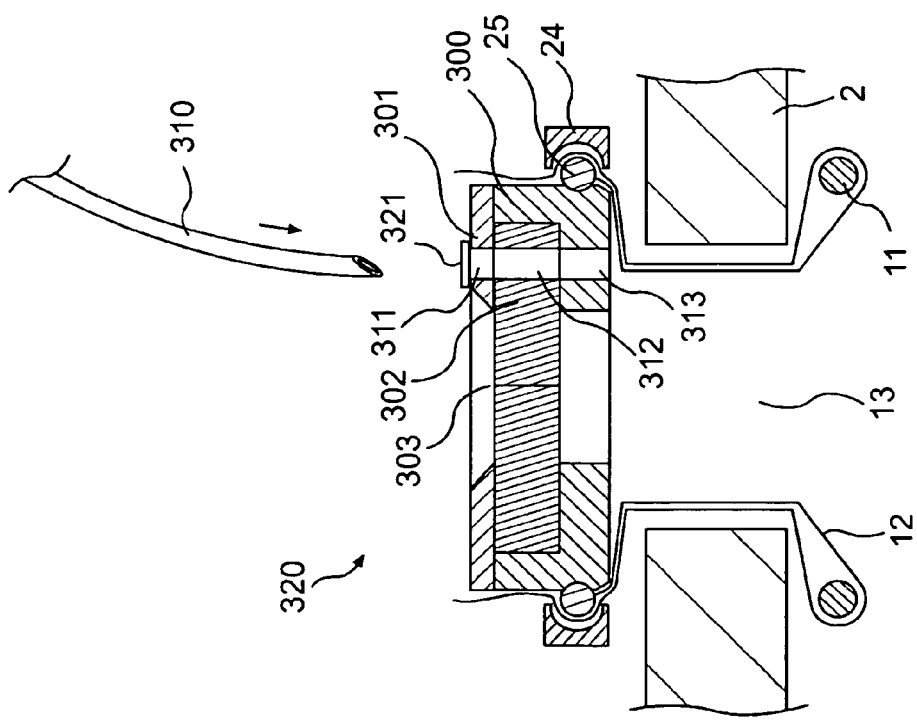

FIGS. 56 to 58 illustrate the use of a gelatinous elastomeric seal/valve 95 as described above with reference to FIGS. 50 to 55 with a valve housing 96 of the type described above.

Referring to FIGS. 58(*a*)(*i*) to 58(*c*)(*iii*) there is illustrated another instrument access device 500 according to the invention, which is similar to the instrument access device of FIGS. 56 to 58, and similar elements in FIGS. 58(*a*)(*i*) to 58(*c*)(*iii*) are assigned the same reference numerals.

In this case the seal/valve housing of the device 500 comprises a housing body 300 and a housing cap 301.

The housing body 300 comprises a reception space 305 for receiving the gelatinous elastomeric seal 302 with the pinhole opening 303 extending therethrough. As illustrated in FIG. 58(*a*)(*ii*), the reception space 305 has an open proximal end which acts as an inlet through which the seal 302 may be located in the reception space 305. The housing body 300 comprises a plurality of upstanding male pins 304 which may be co-operatively associated with corresponding female openings 306 in the seal 302 to control location of the seal 302 in the reception space 305.

In this case the seal 302 is formed separately to the housing body 300. For example, the seal 302 may be formed by casting.

The housing body 300 is mounted to the proximal ring member 25 in a snap-fit arrangement (FIG. 58(*c*)(*i*)). When mounted to the proximal ring member 25, the distal end of the housing body 300 extends distally of the proximal ring member 25 and the housing body 300 is located radially inwardly of the proximal ring member 25.

The housing cap 301 is mounted to the housing body 300 in a snap-fit arrangement to partially close the proximal end inlet of the reception space 305. In this manner the housing cap 301 retains the seal 302 in position in the reception space 305. The housing cap 301 is substantially annular in shape with a central opening to facilitate access to the seal 302 in the reception space 305.

The housing body 300 may be mounted to the proximal ring member 25 before or after retraction of a wound opening.

In use, a wound opening 13 is made in the abdominal wall 2 and the distal O-ring 11 is inserted through the wound opening 13 into the wound interior. The seal housing and the proximal ring members 24, 25 are located externally of the wound opening 13 (FIG. 58(*c*)(*ii*)). The seal housing may be mounted to the inner proximal ring member 25 before or after insertion of the distal O-ring 11 through the wound opening 13.

To retract laterally the sides of the wound opening 13, the outer proximal ring member 24 is pushed distally, which causes the inner proximal ring member 25 and the seal housing to move distally, while the free, proximal end of the sleeve 12 is pulled proximally (FIG. 58(*c*)(*iii*)). An instrument may then be inserted through the pinhole opening 303 of the seal 302 to access the wound interior in a sealed manner.

The excess proximal portion of the sleeve 12 may be removed, for example by cutting away, after retraction of the wound opening 13, as illustrated in FIG. 58(*c*)(*iii*).

Alternatively the excess proximal portion of the sleeve 12 may be sealed to the outer proximal ring member 24 or to the housing body 300, for example using a clamp, to enhance the sealing effect of the instrument access device 500.

As noted previously, the instrument access device 500 is particularly suitable for retracting relatively small wound openings, for example wound openings having a diameter of less than 40 mm, such as between 3 mm and 35 mm, typically between 5 mm and 12 mm. The instrument access device 500 is thus suitable to facilitate access of relatively small laparoscopic instruments, for example instruments having a diameter of less than 40 mm, such as between 3 mm and 35 mm, typically between 5 mm and 12 mm.

Because of the relatively small size of the instrument access device 500, the wound opening 13 may be retracted by moving the sleeve 12 relative to the proximal ring members 24, 25 in a single actuation step. In particular the entire circumference of the sleeve 12 may be gripped by a single hand of a user, and opposite sides of the outer proximal ring member 24 may be gripped by the other hand of the user. The sleeve 12 may then be pulled proximally while the outer proximal ring member 24 is pushed distally to retract the wound opening 13 in a single actuation step.

It will be appreciated that more than one opening may be provided extending through the seal 302. For example, two pinhole openings may be provided, spaced-apart from one another, extending through the seal 302. In this case access may be gained to the wound interior with more than one instrument by extending an instrument through each opening in the seal 302.

FIGS. 58(*d*) and 58(*e*) illustrate a seal/valve housing of another instrument access device according to the invention, which is similar to the seal/valve housing of FIGS. 58(*a*)(*i*) to 58(*c*), and similar elements in FIGS. 58(*d*) and 58(*e*) are assigned the same reference numerals.

In this case, the housing body 300 has an insufflation lumen 313 extending therethrough, the seal 302 has an insufflation lumen 312 extending therethrough, and the housing cap 301 has an insufflation lumen 311 extending therethrough. As illustrated in FIG. 58(*e*), the three insufflation lumena 313, 312, 311 are in alignment, and the longitudinal axis of each insufflation lumen 313, 312, 311 is parallel to the longitudinal axis of the instrument access device. An insufflation tube 310 may be inserted into the insufflation lumen 311 of the housing cap 301 to insufflate a wound interior (FIG. 58(*e*)).

In FIGS. 58(*f*) and 58(*g*) there is illustrated another instrument access device 320 according to the invention comprising a seal/valve housing, which is similar to the seal/valve housing of FIGS. 58(*d*) and 58(*e*), and similar elements in FIGS. 58(*f*) and 58(*g*) are assigned the same reference numerals.

In this case the instrument access device 320 comprises a temporary insufflation seal 321 fixed to the housing cap 301 at the proximal end of the housing cap insufflation lumen 311. The seal 321 seals the insufflation lumena 311, 312, 313 to prevent discharge of gas from the insufflated wound interior. The seal 321 may be pierced by a pointed distal end of the insufflation tube 310, for example if it is required to further insufflate the wound interior.

Once the access device 320 has been fired, and the excess sleeve 12 removed, the insufflation tube 310 can be connected by piercing the temporary seal 321 which maintains pneumoperitoneum.

The distal ring 11 of the device 320 is configured to be sufficiently flexible for ease of insertion of the distal ring 11 through the wound opening 13 prior to retraction. The distal ring 11 is also configured to be sufficiently rigid to anchor the device 320 in position in the wound opening 13 during retraction of the wound opening 13. The sleeve 12 has sufficient strength to facilitate transmission of the retraction force required to retract the wound opening 13.

It will be appreciated that the distal ring may be provided in any suitable configuration for ease of insertion through the wound opening 13 prior to retraction. For example at least part of the distal ring 11 may be provided in the form of a shape-memory material, such as Nitinol.

Referring to FIGS. 58(*h*) and 58(*i*) there is illustrated a further instrument access device 330 according to the invention, which is similar to the instrument access device 320 of FIGS. 58(*f*) and 58(*g*), and similar elements in FIGS. 58(*h*) and 58(*i*) are assigned the same reference numerals.

In this case the instrument access device 330 comprises an intermediate connector 331 to connect the insufflation tube 310 in communication with the insufflation lumena 311, 312, 313. As illustrated the intermediate connector 331 is substantially "L"-shaped. In this manner the insufflation tube 310 may be connected in communication with the insufflation lumena 311, 312, 313 with the longitudinal axis A-A of the insufflation tube 310 at the distal end of the insufflation tube 310 substantially perpendicular to the longitudinal axes B-B of the insufflation lumena 311, 312, 313.

The access device 330 has an alternative insufflation connection means in the form of a tube 331 with an angle and a valve connector. The valve connector may be closed when not connected to the insufflation supply 310 (FIG. 58(*h*)).

Figure 60:
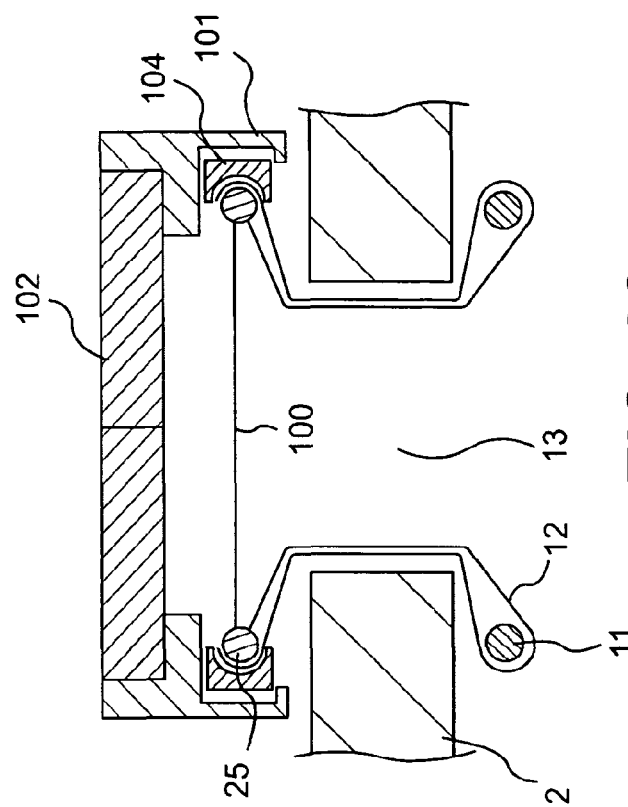
FIGS. 59 to 61 are cross sectional, side views of another instrument access device of the invention.
Figure 59:
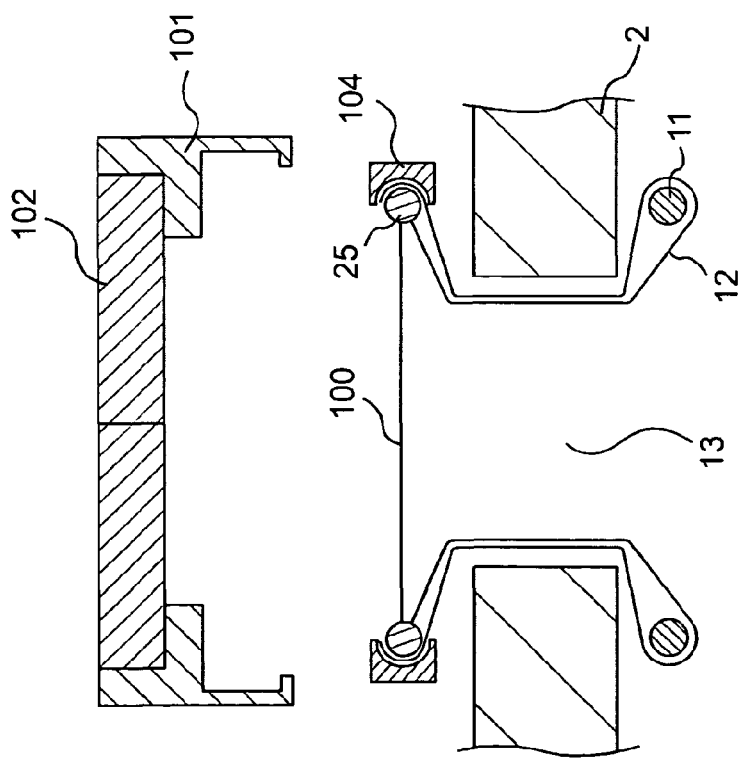
Figure 61:
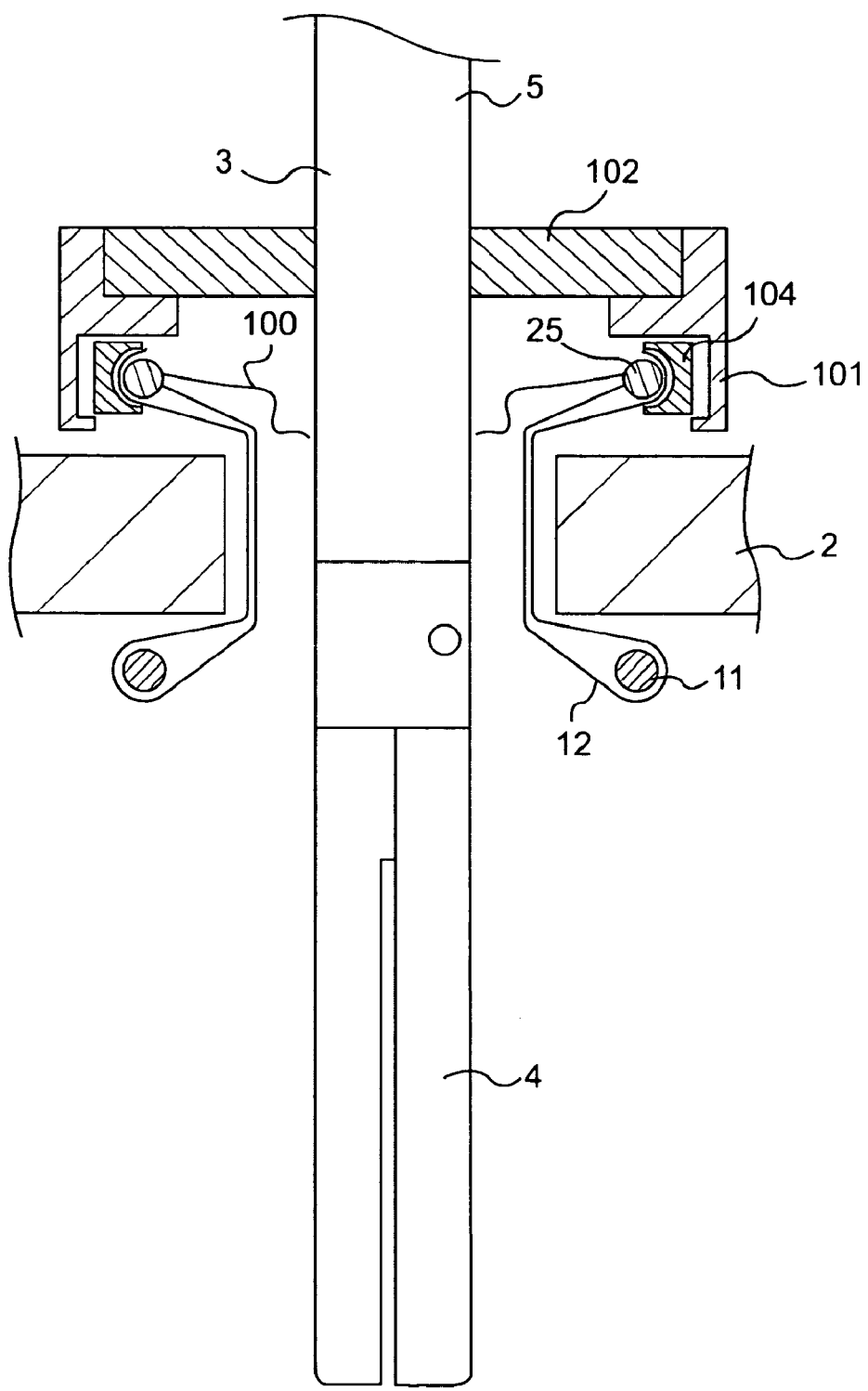

FIGS. 59 to 61 illustrate a still further instrument access device of the invention which in this case has a sheet of film material 100 extending across the inner proximal ring 25. A valve housing 101 is mounted to an outer proximal ring 104, for example by snap fitting and a gelatinous elastomeric seal 102 seals to an instrument 3 which in use pierces through the gel 102 and through the proximal film 104.

Figure 62:
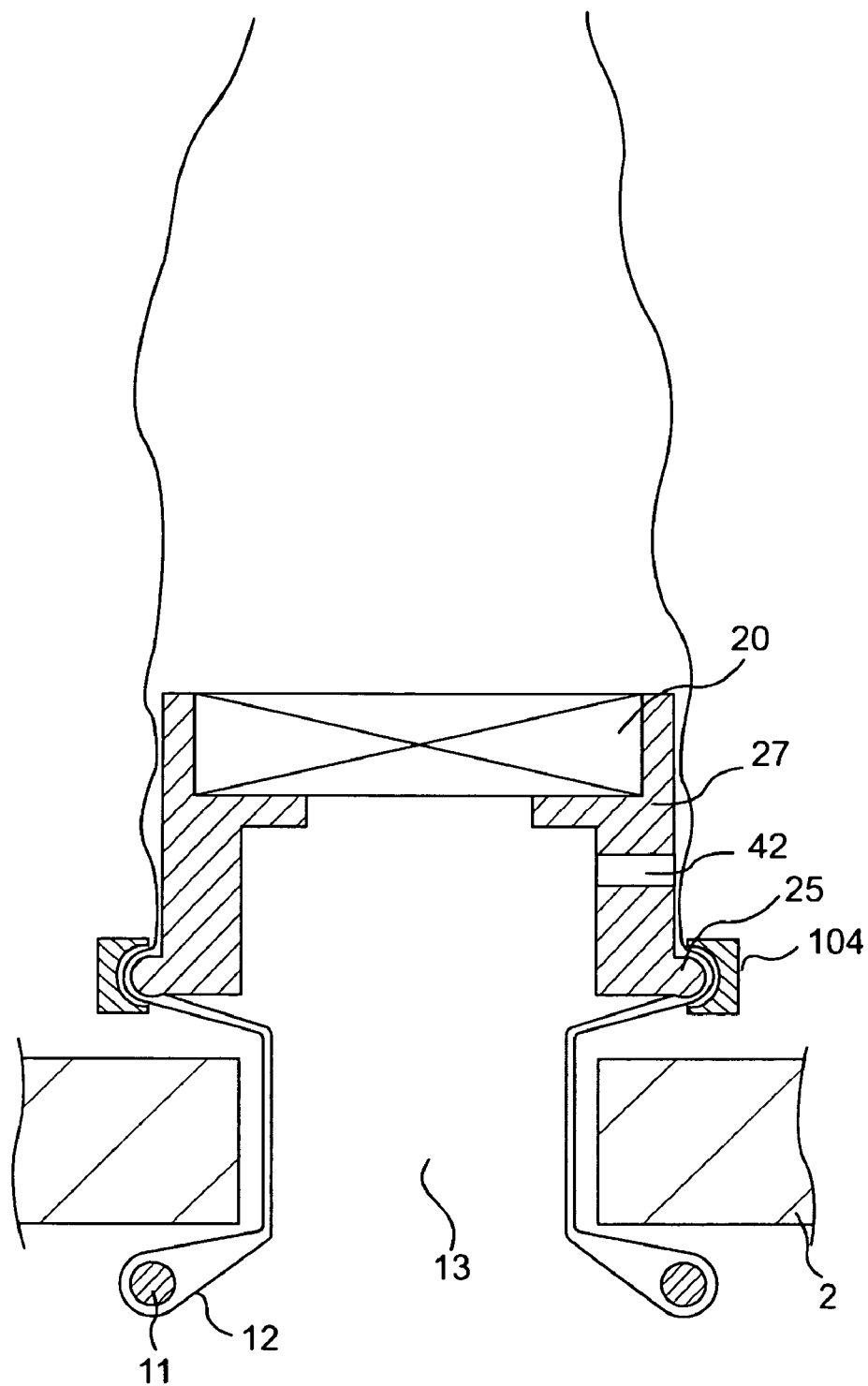
FIGS. 62 to 64 are cross sectional, side views of a further instrument access device of the invention.
Figure 63:
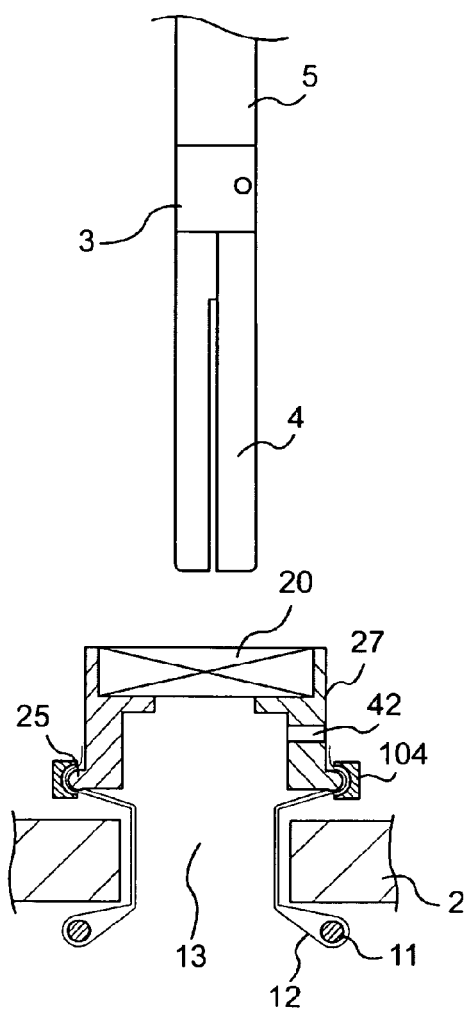
Figure 64:
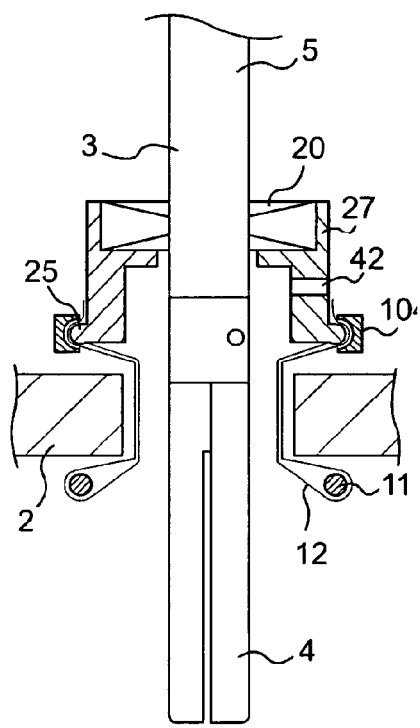
Figure 65:
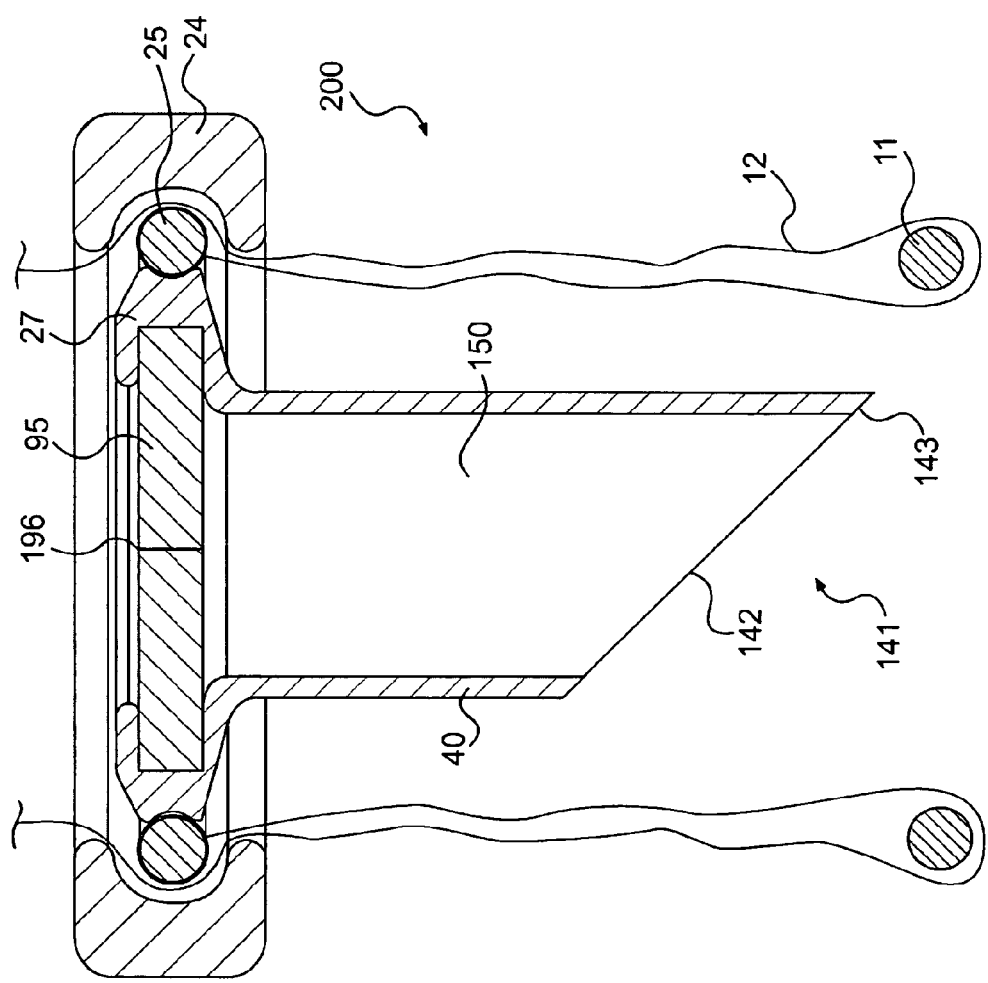
FIG. 65 is a cross sectional, side view of another instrument access device according to the invention.
Figure 66:
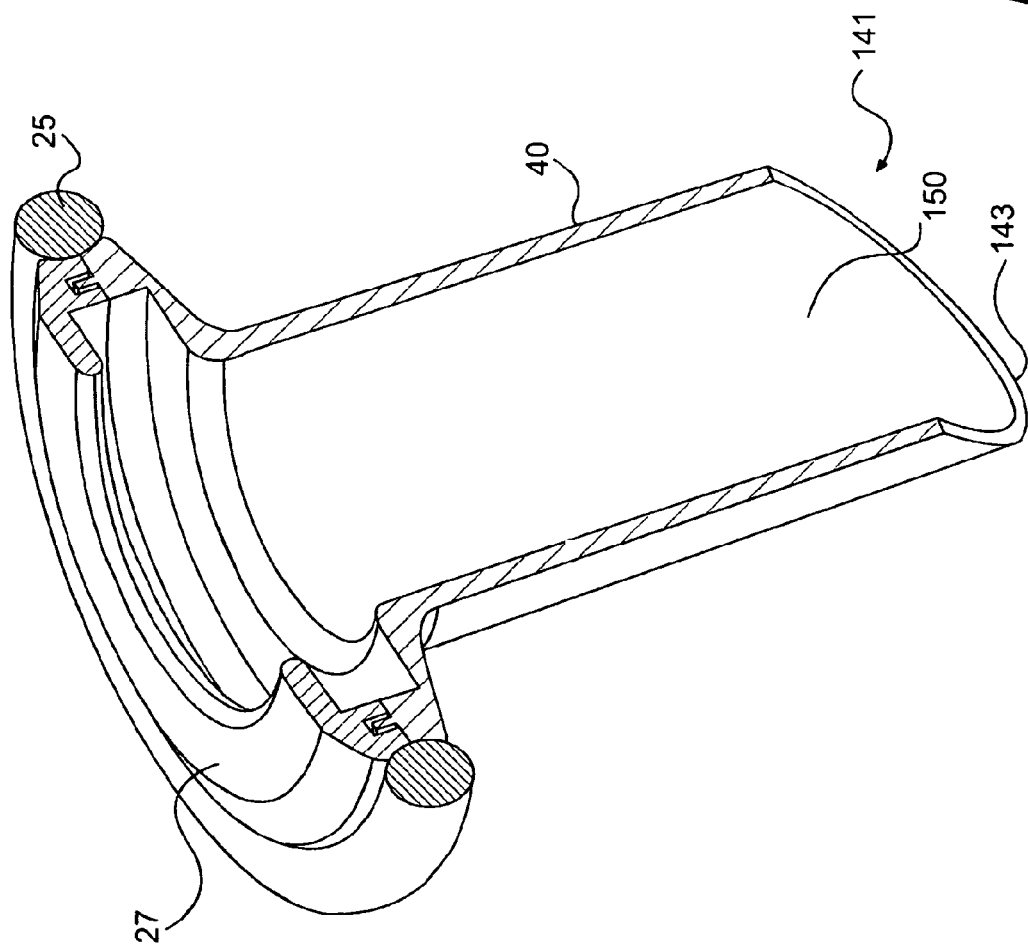
FIG. 66 is a cut-away, perspective view of a part of the device of FIG. 65.
Figure 67:
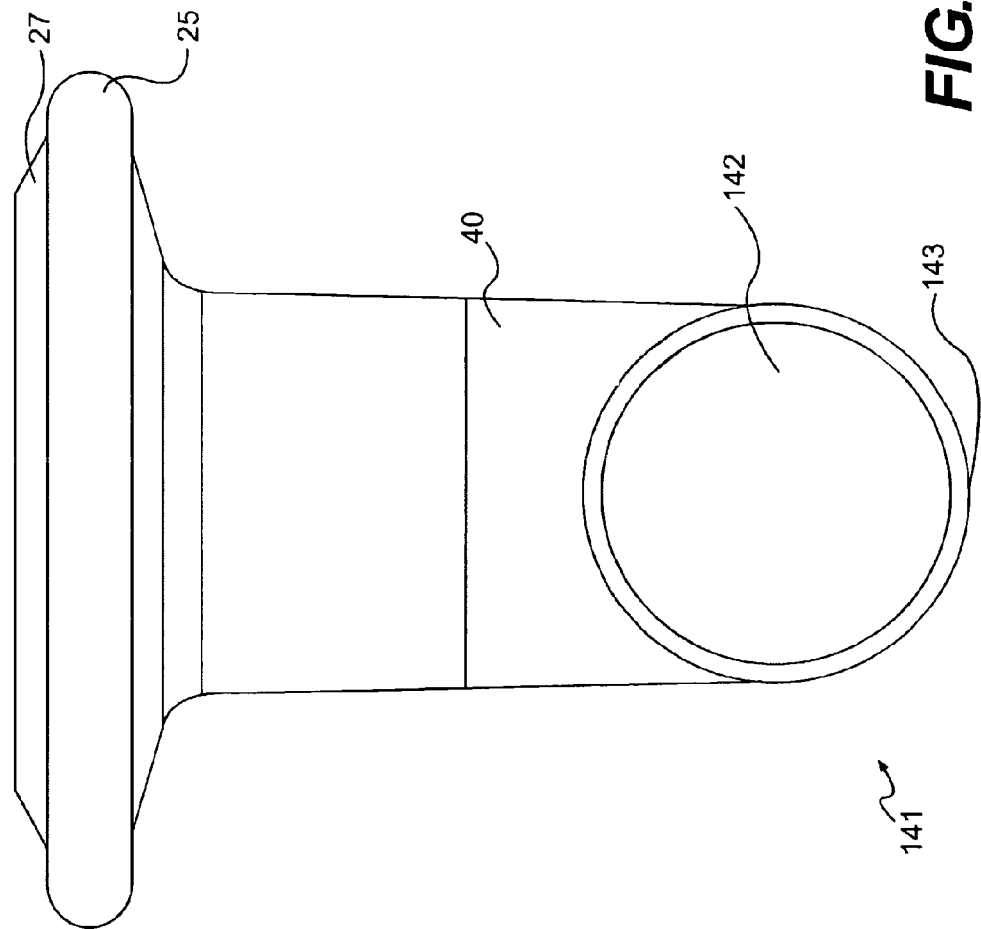
FIG. 67 is an end view of the part of FIG. 66.

Referring to FIGS. 62 to 64 there is illustrated another instrument access device with valve(s) 20. Again, as in some previous embodiments the sleeve 13 is pulled upwardly on deployment, leaving the valve 20 free of sleeve material.

Referring to FIGS. 65 to 70 there is illustrated another instrument access device 200 according to the invention, which is similar to the devices of FIGS. 13 to 16 and FIGS. 56 to 58, and similar elements in FIGS. 65 to 70 are assigned the same reference numerals.

In this case the sleeve 12 is fixedly attached at one end to the inner proximal ring 25, extends distally in a first layer to the distal ring 11, is looped around the distal ring 11, extends proximally in a second layer to the proximal rings 25, 24, and passes proximally between the inner proximal ring 25 and the outer proximal ring 24.

The tubular member 40 is integrally formed with the housing 27, and the housing 27 is mounted to the inner proximal ring 25.

The seal/valve 95 is provided in the form of a gelatinous elastomeric material which is mounted to the housing 27. The seal/valve 95 has a pinhole opening 196 extending therethrough through which an instrument 3 may be extended. The opening 196 is biased towards a closed configuration.

A lumen 150 extends through the tubular member 40 through which an instrument 3 may be extended. The tubular member 40 has a distal opening 142 at a distal end 141 of the tubular member 40.

The tubular member 40 has a skived distal end 141, in this case. In particular the plane of the distal opening 142 is inclined relative to the longitudinal axis of the tubular member 40, for example inclined at an angle of 45°. This configuration results in a low-profile, tapered leading end for the tubular member 40 which tapers to a point 143.

The benefit of having the truncated/skived tubular member is that the point 143 on the leading edge of the truncated member 40 more easily finds the narrow, unretracted hole of the incision 1. As it advances downwards, the taper 141 gradually spreads the incision 1 open.

The distal end 141 of the tubular member 40 is truncated, e.g. at an angle of 45°. This yields a narrow leading edge 143 on the tubular member 40 which more easily locates the incision 1, through which the distal ring 11 and the sleeve 12 have already been passed. Furthermore the taper will aid the retraction of the incision 1 as it advances downwards.

The length of the tubular member 40 relative to the abdominal wall thickness may vary.

Figure 69:
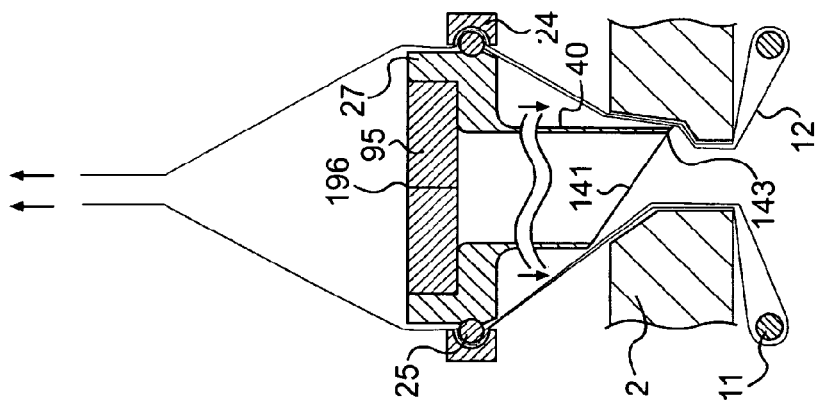
Figure 68:
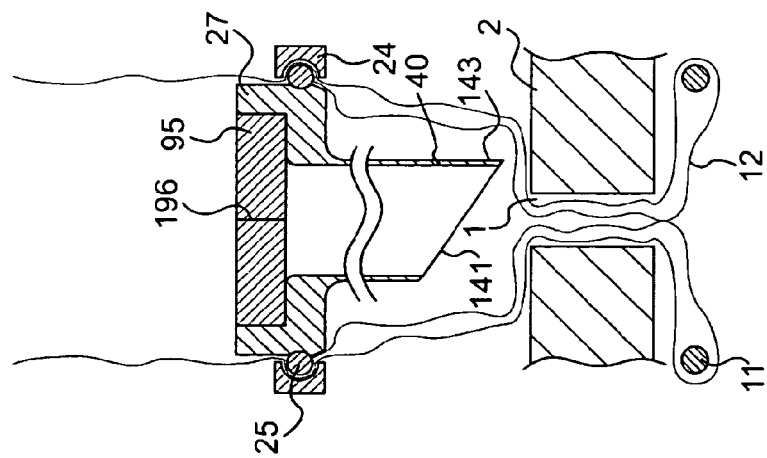
Figure 70B:
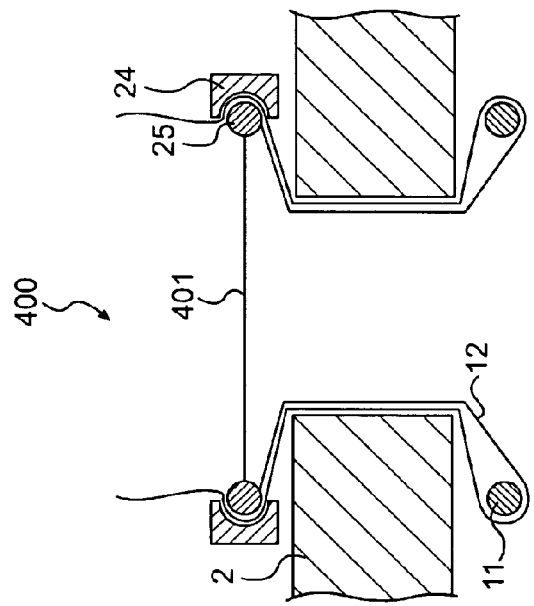
Figure 70A:
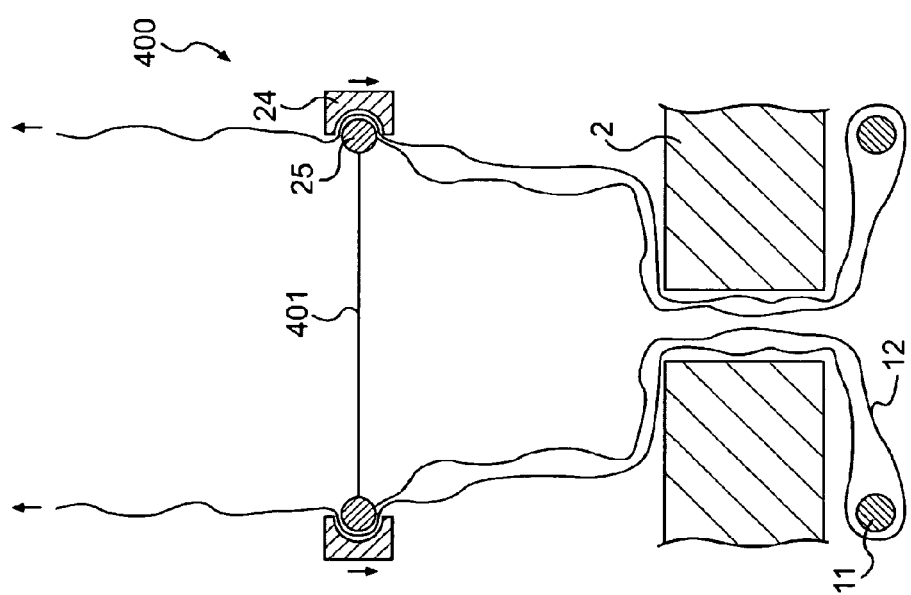
Figure 70F:
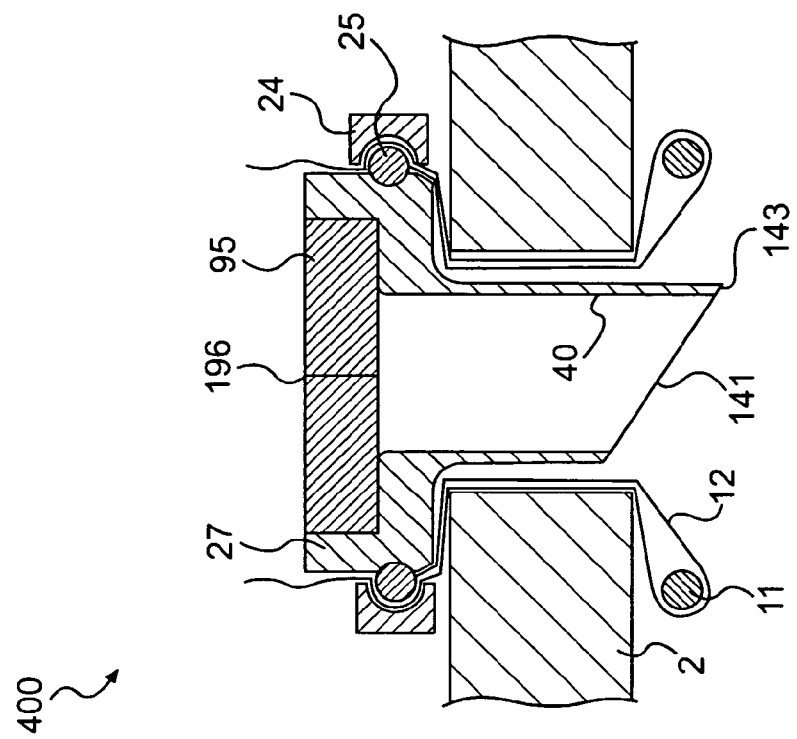
Figure 70E:
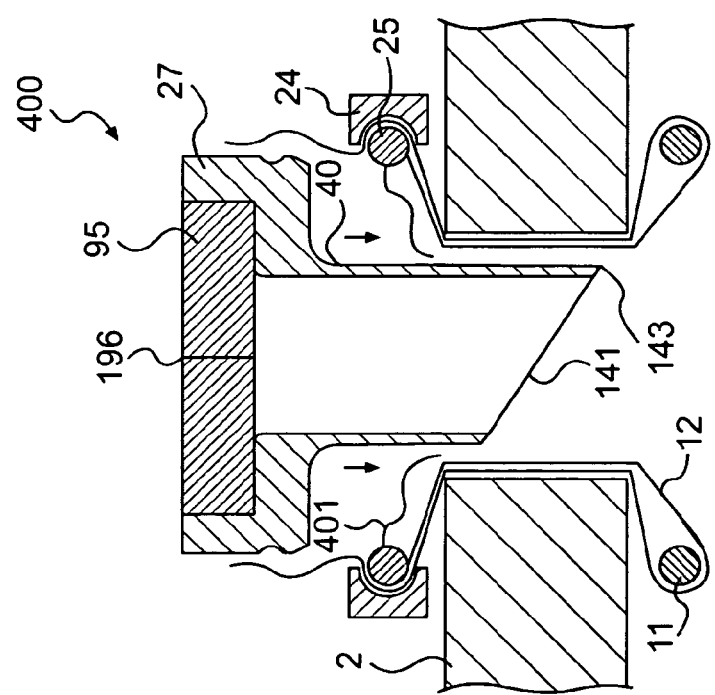
Figure 70I:
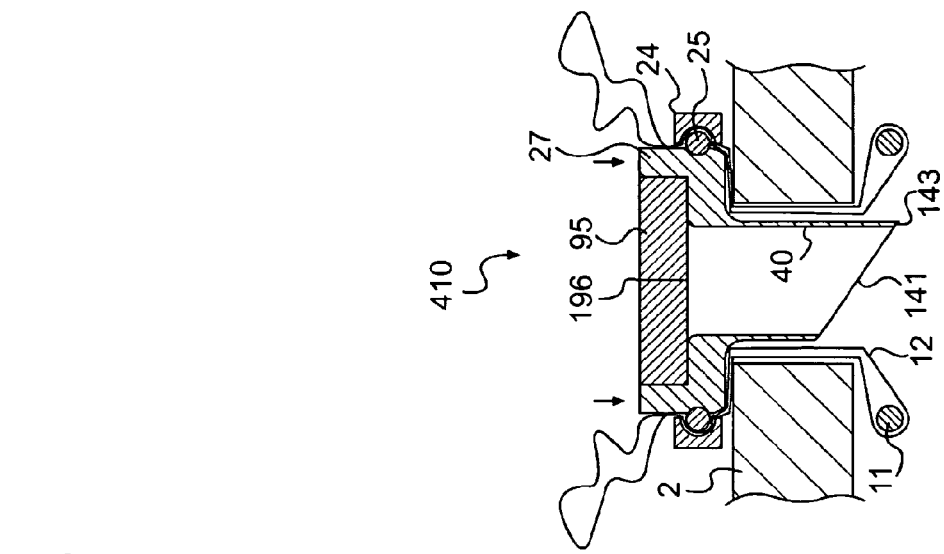
FIGS. 70(g) to 70(i) are cross-sectional, side views of another instrument access device according to the invention, in use.
Figure 70H:
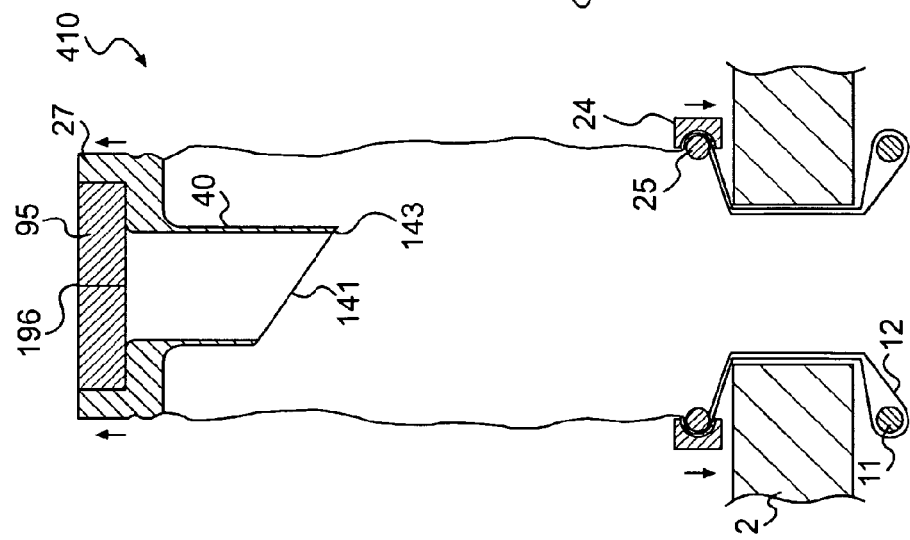
Figure 70G:
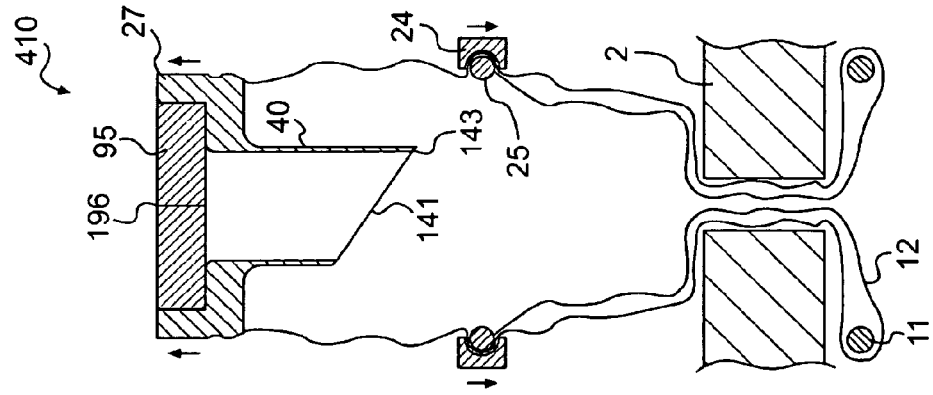

Upon pulling of the sleeve 12 proximally and pushing of the tubular member 40 distally, the incision 1 is retracted by a combined action of the skived distal end 141 of the tubular member 40 forcing the sides of the incision 1 apart and of the sleeve 12 pulling the sides of the incision 1 laterally, as illustrated in FIG. 69. The skived distal end 141 of the tubular member 40 assists in guiding the point 143 of the tubular member 40 to the unretracted incision 1, for subsequent advancement of the tubular member 40 through the incision 1.

After insertion of the tubular member 40 into the incision 1, the point 143 of the tubular member 40 is located within the wound interior distally of the incision 1. However it will be appreciated that the length of the tubular member 40 may be adjusted to suit the particular anatomy of a patient and/or to suit the preferences of a surgeon. In certain cases after insertion of the tubular member 40 into the incision 1, the distal end of the tubular member 40 may be located within the incision 1 proximally of the wound interior.

Figure 70:
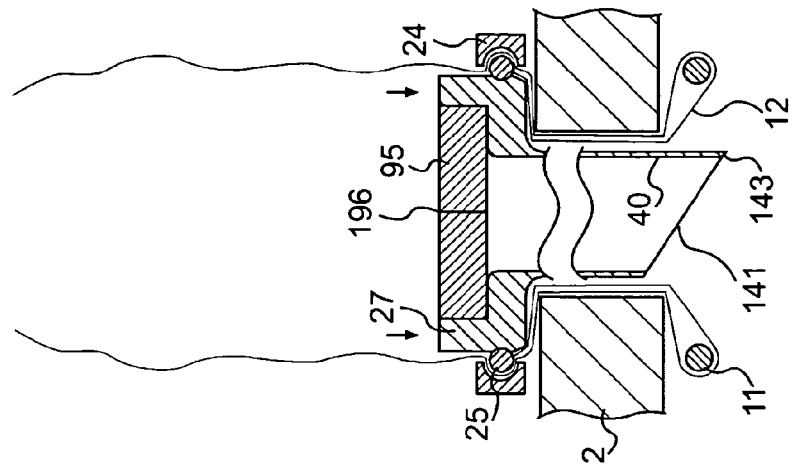
FIGS. 68 to 70 are cross-sectional, side views of the device of FIG. 65, in use.

FIGS. 70(*a*) to 70(*f*) illustrate another instrument access device 400 according to the invention, which is similar to the instrument access device 200 of FIGS. 65 to 70, and similar elements in FIGS. 70(*a*) to 70(*f*) are assigned the same reference numerals.

In this case the inner proximal ring 25 has a seal 401 extending across the inner proximal ring 25. The seal 401 prevents gas leakage from the insufflated wound interior when the wound opening has been retracted (FIG. 70(*b*)).

The housing 27 is mountable to and demountable from the inner proximal ring 25 in a snap-fit arrangement (FIGS. 70(*e*) and 70(*f*)). Upon mounting of the housing 27 to the inner proximal ring 25 after the wound opening has been retracted, the pointed tip 143 of the tubular member 40 pierces the seal 401 (FIGS. 70(*d*) and 70(*e*)).

Mounting of the housing 27 to the inner proximal ring 25 proceeds in a manner similar to that described previously with reference to FIGS. 26 to 28.

FIGS. 70(*a*) to 70(*f*) illustrate a modular instrument access device 400. The gel valve 95 has been separated from the retractor base 25. It may be easier to introduce a cannulated gel housing 27 into an incision this way, rather than trying to do it at the same time as the retracting phase. FIG. 70(*a*) illustrates the disc of film 401 mounted in the proximal 'O' ring 25 to maintain pneumoperitoneum. When pneumoperitoneum has been established, the film 401 prevents pressure loss. FIG. 70(*d*) illustrates the leading tip 143 of the truncated cannula 40 beginning to pierce the disc of film 401. In FIG. 70(*e*) the disc of film 401 has been pierced. FIG. 70(*f*) illustrates the snap-fit connection between the gel housing 27 and the proximal 'O' ring 25 of the retractor 400.

Referring to FIGS. 70(*g*) to 70(*i*) there is illustrated another instrument access device 410 according to the invention, which is similar to the instrument access device 400 of FIGS. 70(*a*) to 70(*f*), and similar elements in FIGS. 70(*g*) to 70(*i*) are assigned the same reference numerals.

In this case, the sleeve 12 extends distally from the inner proximal ring 25 to the distal ring 11, loops around the distal ring 11, extends proximally from the distal ring 11 to the proximal rings 24, 25, extends between the inner proximal ring 25 and the outer proximal ring 24, and extends proximally to the housing 27 to which the sleeve 12 is fixedly attached. Before the housing 27 is mounted to the inner proximal ring 25, any gas leakage from the wound interior through the retracted wound opening is contained within the sleeve 12, and thus pneumoperitoneum is maintained (FIG. 70(*h*)). No seal is provided, in this case, extending across the inner proximal ring 25.

FIGS. 70(*g*) to 70(*i*) illustrate another modular instrument access device, the gel housing 27 with the cannula 40 is fixed to the proximal end of the sleeve 12. A snap fit connection is used to secure the gel housing 27 to the proximal 'O' ring 25 of the retractor 410.

In FIGS. 71 to 73 there is illustrated another instrument access device 340 according to the invention, which is similar to the instrument access device 200 of FIGS. 65 to 70, and similar elements in FIGS. 71 to 73 are assigned the same reference numerals.

In this case no tubular member is provided extending distally from the housing 27.

The outer proximal ring 341 is releasably mounted to the inner proximal ring 25, in this case. In particular the outer proximal ring 341 has a curved engagement surface which extends in cross-section for a quarter-revolution, as illustrated in FIGS. 71 and 72. The curved engagement surface rests upon the proximal side of the inner proximal ring 25, with the sleeve 25 extending between the inner proximal ring 25 and the outer proximal ring 341, to mount the outer proximal ring 341 to the inner proximal ring 25. This arrangement enables the outer proximal ring 341 to be removed after retraction of the wound opening (FIG. 73).

In use, the distal ring 11 is inserted through the wound opening into the wound interior, and the inner proximal ring 25 is located externally of the wound opening with the sleeve 12 extending from the distal ring 11 to the inner proximal ring 25 in the double-layer arrangement. The outer proximal ring 341 is then mounted to the inner proximal ring 25 with the sleeve 12 extending therebetween (FIG. 71).

The sleeve 12 is then pulled proximally while pushing the outer proximal ring 341 distally. The outer proximal ring 341 engages the inner proximal ring 25 and thus the housing 27, the inner proximal ring 25 and the outer proximal ring 341 all move distally to retract laterally the sides of the wound opening (FIG. 72).

After retraction of the wound opening, the outer proximal ring 341 may be removed while the distal ring 11, the inner proximal ring 25 and the sleeve 12 remain in position retracting the wound opening (FIG. 73).

The outer proximal ring 341 acts as a guide to guide movement of the inner proximal ring 25 relate to the sleeve 12. In this case, the outer proximal ring 341 does not act as a locking mechanism to lock the sleeve 12 with the wound retracted.

FIGS. 71 to 73 show how only half an outer proximal ring 341 is needed to provide support when firing the instrument access device 340. The device 340 functions to retract the wound opening without the outer proximal ring 341 (FIG. 73).

The access ports of the invention can be used in a number of ways. In one method the retractor is used as described above, the distal inner ring 11 being inserted into an incision 1, the outer ring being slid to controllably radially expand the incision 1. The retractor may then be locked in position. If necessary, the outer ring can be moved further downwardly to create a larger incision.

In some arrangements an instrument may be bent manually outside the body and the bent instrument is delivered through the access port to readily access the operative site.

In a further embodiment an instrument is inserted into the access port and the surgeon uses the abdominal wall itself to bend the instrument and then insert the bent section further into the abdomen.

It will be appreciated that the instrument access device of the invention may have a valve or seal in the form of a gelatinous elastomeric material, or in any other suitable form, for example a lip seal.

The access ports of the invention have at least some of the following advantages:

Controlled Radial Expansion
1. Greater access using smaller incision
2. Can vary incision size as need be (e.g. specimen removal during lap coli.)

Greater Sealing Capabilities
1. No gas leakage from the wound margins
2. Cannot be inadvertently pulled out of the incision
3. Will seal any incision and never require secondary sealing method (suture, Hassan port, etc.)

Eliminate Intra-Abdominal Profile
1. Gives back more working space in the abdomen (critical in pelvic surgery)
2. Perineal access for operations such as Radical Prostatectomy.

Protection of Wound from Infection and Cancer Seeding
1. Tight seal with no "chimney stack" effect
2. Upon removal all areas of potential contamination are isolated from the incision Reduced Extra-Abdominal Profile
1. Will increase the effective working length of an instrument
2. Greater working area outside the abdomen Increase the Freedom of Movement of Conventional Laparoscopic Instruments The instrument access device of the invention enables a surgeon to gain access to a wound interior using an instrument while minimising the incision size at the wound interior to minimise the possibility of post-operative herniation.

The retractor of the invention may be inserted through the abdominal wall as described below. An initial thin incision may be made in the abdominal wall and an inner distal ring of the retractor may be attached to an insertion tool. The ring is flexible and can be stretched or bent for ease of insertion through the incision.

In some cases the ring may be inserted through the incision using a blunted or round-nosed obturator tool.

Alternatively the ring may be inserted using an obturator/trocar tool with a leading cutting blade. In this case the tool itself makes an incision in the abdominal wall, allowing the distal ring of the retractor to be delivered and deployed.

Further means and methods suitable for introducing the instrument access device of the invention into a wound opening, and suitable for withdrawing the instrument access device of the invention from a wound opening are described in International patent application published under Nos. WO 2004/026153, WO 2004/030547, WO 2004/054456, and WO 2005/009257, the relevant contents of which are incorporated herein by reference.

The invention is not limited to the embodiments hereinbefore described, with reference to the accompanying drawings, which may be varied in construction and detail.

The invention claimed is:

1. A method of operating an instrument access device, including a retractor assembly, a retractor seal for positioning at a proximal portion of the retractor assembly, and an instrument valve assembly, the method comprising:
retracting a wound opening with the retractor assembly, wherein retracting the wound opening includes:
inserting a distal member of the retractor assembly through the wound opening,
positioning a retracting sleeve of the retractor assembly within the wound opening, and
positioning a proximal member of the retractor assembly external to the wound opening;
penetrating the retractor seal with the instrument valve assembly, wherein the retractor seal is unperforated prior to penetration of the retractor seal with the instrument valve assembly; and
sealing the retractor assembly for insufflation, wherein the sealing of the retractor assembly is provided, at least in part, by the instrument valve assembly.

2. The method of claim 1, wherein the instrument valve assembly includes a tapered distal portion for penetrating the retractor seal.

3. The method of claim 1, wherein penetrating the retractor seal includes penetrating while the retractor seal is supported by the proximal member along an exterior side of the wound opening.

4. A method of operating an instrument access device, including a retractor assembly, a retractor seal for positioning at a proximal portion of the retractor assembly, and an instrument valve assembly, the method comprising:
retracting a wound opening with the retractor assembly, wherein retracting the wound opening includes:
inserting a distal member of the retractor assembly through the wound opening,
positioning a retracting sleeve of the retractor assembly within the wound opening, and
positioning a proximal member of the retractor assembly external to the wound opening;
piercing the retractor seal with the instrument valve assembly, wherein piercing the retractor seal includes making an opening through the retractor seal with the instrument valve assembly; and
sealing a proximal end of the retractor assembly for insufflation, wherein the sealing of the proximal end of the retractor assembly is provided, at least in part, by the instrument valve assembly.

5. The method of claim 4, wherein piercing the retractor seal includes forcing a tapered distal end of the instrument valve assembly through the retractor seal.

6. The method of claim 4, further including positioning the retractor seal along an external side of the wound opening.

7. The method of claim 4, further including insufflating a wound interior with gas, and preventing leakage of the gas through the wound opening from the insufflated wound interior by coupling the retractor seal and the instrument valve assembly.

8. The method of claim 4, wherein sealing the retractor assembly includes forming a seal about an outer circumference of the proximal member.

9. The method of claim 4, further including inserting an instrument through the instrument valve assembly.

10. The method of claim 4, wherein sealing the retractor assembly includes forming a seal about an outer periphery of the instrument valve assembly.

11. The method of claim 1, wherein sealing the retractor assembly includes forming a seal about an outer periphery of the proximal member by clamping one or more sealing surfaces about the outer periphery of the proximal member.

12. The method of claim 1, wherein after penetrating the retractor seal, the instrument valve assembly is coupled to the retractor seal.

13. The method of claim 1, wherein sealing the retractor assembly includes forming a seal about an outer periphery of the instrument valve assembly.

14. A method of operating an instrument access device, including a retractor assembly, a retractor seal for positioning at a proximal portion of the retractor assembly, and an instrument valve assembly, the method comprising:
retracting a wound opening with the retractor assembly, wherein retracting the wound opening includes:
inserting a distal member of the retractor assembly through the wound opening,
positioning a retracting sleeve of the retractor assembly within the wound opening, and
positioning a proximal member of the retractor assembly external to the wound opening;
penetrating the retractor seal with the instrument valve assembly; and
sealing the retractor assembly, wherein sealing includes bringing an annular recess of the instrument valve assembly into engagement with the retractor seal, and wherein the annular recess is formed by a portion of an exterior surface of the instrument valve assembly, the portion of the exterior surface having a fixed shape.

15. The method of claim 14, wherein penetrating the retractor seal includes inserting a distal end of the instrument valve assembly through the retractor seal, with an enlarged proximal end of the instrument valve assembly housing an instrument valve.

16. The method of claim 14, wherein penetrating includes forming an opening through the retractor seal.

17. The method of claim 14, wherein penetrating includes forcing a tapered distal end of the instrument valve assembly through the retractor seal.

18. The method of claim 14, wherein sealing the retractor assembly includes forming a seal about an outer surface of the proximal member.

19. The method of claim 14, wherein sealing the retractor assembly includes forming a seal about the annular recess of the instrument valve assembly.

20. The method of claim 1, wherein penetrating the retractor seal with the instrument valve assembly includes creating a perforation in the retractor seal with the instrument valve assembly.

* * * * *